United States Patent
Kufe

(10) Patent No.: US 8,129,345 B2
(45) Date of Patent: *Mar. 6, 2012

(54) MUC1-IκB KINASE COMPLEXES AND THEIR ACTIVITIES

(75) Inventor: Donald W. Kufe, Wellesley, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 577 days.

This patent is subject to a terminal disclaimer.

(21) Appl. No.: 11/781,148

(22) Filed: Jul. 20, 2007

(65) Prior Publication Data

US 2008/0241125 A1 Oct. 2, 2008

Related U.S. Application Data

(60) Provisional application No. 60/832,369, filed on Jul. 20, 2006.

(51) Int. Cl.
*A61K 38/04* (2006.01)
*A61K 38/17* (2006.01)

(52) U.S. Cl. ............. 514/19.3; 514/19.2; 514/19.4; 514/19.5; 514/19.6; 514/21.3; 514/21.6; 424/184.1; 424/185.1; 424/192.1; 424/193.1

(58) Field of Classification Search ............. 514/19.2, 514/19.3, 19.4, 19.5, 19.6, 21.3, 21.6; 424/184.1, 424/185.1, 192.1, 193.1
See application file for complete search history.

(56) References Cited

U.S. PATENT DOCUMENTS

| | | | |
|---|---|---|---|
| 4,522,811 A | 6/1985 | Eppstein et al. | 514/2 |
| 5,506,343 A | 4/1996 | Kufe | 424/130.1 |
| 5,565,334 A | 10/1996 | Kufe et al. | 435/69.1 |
| 5,597,457 A | 1/1997 | Craig et al. | 204/165 |
| 5,790,421 A | 8/1998 | Osslund | 703/2 |
| 5,827,516 A | 10/1998 | Urban et al. | 424/93.21 |
| 5,874,415 A | 2/1999 | Kufe et al. | 514/44 |
| 6,093,573 A | 7/2000 | Beamer et al. | 436/86 |
| 6,696,498 B2 | 2/2004 | Santoro | 514/690 |
| 7,345,078 B2 | 3/2008 | Tepe et al. | 514/401 |
| 7,767,642 B2 * | 8/2010 | Schroeder | 424/1.69 |
| 2002/0041868 A1 | 4/2002 | Nicolette et al. | 424/93.21 |
| 2002/0110841 A1 | 8/2002 | Kufe | 435/7.23 |
| 2004/0018181 A1 | 1/2004 | Kufe et al. | 514/44 |
| 2004/0166543 A1 | 8/2004 | Kufe et al. | 435/7.23 |
| 2005/0042209 A1 | 2/2005 | Kufe et al. | 424/93.21 |
| 2005/0053606 A1 | 3/2005 | Kufe et al. | 424/155.1 |
| 2007/0105767 A1 | 5/2007 | Kharbanda et al. | 514/8 |
| 2007/0202134 A1 | 8/2007 | Kufe | 53/24.5 |
| 2008/0090770 A1 | 4/2008 | Belmares et al. | 514/18 |
| 2008/0107661 A1 | 5/2008 | Kufe | 424/133.1 |

FOREIGN PATENT DOCUMENTS

WO WO 02/068668 9/2002

OTHER PUBLICATIONS

Kaufman, H.L., et al. Lancet Oncol. 6: 62-63, 2005.*
Verma, Nature, 1997, vol. 389, pp. 239-242.*
Favaro, E., et al., PubMed Abstract of Current Opinion Mol. Ther., 9(5): 477-482, 2007; Abstract Only.*
Rubyani, G.M., Molecular Aspects of Medicine, 22: 113-142, 2001.*
Ahmad, R, et al., Nature Cell Biology, 9(12): 1419-1427 and pp. 1-10 of supplementary information, 2007.*
International Search Report and Written Opinion, issued in International Application No. PCT/US07/74047, dated Sep. 5, 2008.
U.S. Appl. No. 07/149,831, filed Oct. 16, 1990, Kufe.
U.S. Appl. No. 10/293,391, filed Nov. 13, 2002, Kufe et al.
U.S. Appl. No. 11/816,402, filed Aug. 15, 2007, Kufe.
U.S. Appl. No. 11/915,291, filed Nov. 21, 2007, Kufe.
U.S. Appl. No. 12/024,715, filed Feb. 1, 2008, Kufe.
U.S. Appl. No. 12/024,962, filed Feb. 1, 2008, Kufe.
U.S. Appl. No. 12/031,316, filed Dec. 14, 2008, Kufe.
U.S. Appl. No. 12/064,425, filed Feb. 21, 2008, Kufe.
Ashburner et al., "The p65 (RelA) subunit of NF-kappaB interacts with the histone deacetylase (HDAC) corepressors HDAC1 and HDAC2 to negatively regulate gene expression," *Mol. Cell Biol.*, 21:7065-7077, 2001.
Beatty et al., "Cutting edge: transgenic expression of human MUC1 in IL-10-/- mice accelerates inflammatory bowel disease and progression to colon cancer," *J. Immunol.*, 179:735-739, 2007.
Brody and Gold, "Aptamers as therapeutic and diagnostic agents," *Rev. Mol. Biotech.*, 74:5-13, 2000.
Broughton, "Molecular modeling," *Curr. Opin. Chem. Biol.*, 1, 392-398, 1997.
Cane et al., "Harnessing the biosynthetic code: combinations, permutations, and mutations," *Science*, 282:63-68, 1998.
Cristiano et al., "Molecular conjugates: a targeted gene delivery vector for molecular medicine," *J. Mol. Med.*, 73:479-486, 1995.
Delhase et al., "Positive and negative regulation of IkappaB kinase activity through IKKbeta subunit phosphorylation," 284:309-313, 1999.
Gendler et al., "A highly immunogenic region of a human polymorphic epithelial mucin expressed by carcinomas is made up of tandem repeats," *J. Biol. Chem.*, 263:12820-12823, 1988.
Hayden et al., "Signaling to NF-kappaB," *Genes Dev.*, 18:2195-2224, 2004.
Huang et al., "MUC1 cytoplasmic domain coactivates Wnt target gene transcription and confers transformation," *Cancer Biol. Ther.*, 2:702-706, 2003.

(Continued)

*Primary Examiner* — Alana Harris Dent
*Assistant Examiner* — Anne Holleran
(74) *Attorney, Agent, or Firm* — Fulbright & Jaworski

(57) ABSTRACT

The disclosure provides methods of identifying and making compounds and pharmaceutical compositions containing the compounds that inhibit the interaction between MUC1 and an IKK. The disclosure also provides in vivo and in vitro methods of inhibiting such an interaction. Also embraced by the disclosure are in vitro and in vivo methods of inhibiting the IKK/NF-κB pathway in cells expressing MUC1. The compounds, compositions, and methods of the disclosure are generally useful in the treatment of various cancers, inflammatory (e.g., autoimmune disorders), and transplant rejection.

10 Claims, 16 Drawing Sheets

OTHER PUBLICATIONS

Inohara et al., *J. Biol. Chem.*, "An induced proximity model for NF-kappa B activation in the Nod1/RICK and RIP signaling pathways," 275:27823-27831, 2000.

Karin et al., "NF-kappaB in cancer: from innocent bystander to major culprit," *Nat. Rev. Cancer*, 2:301-310, 2002.

Kharbanda et al., "Nuclear signaling induced by ionizing radiation involves colocalization of the activated p56/p53lyn tyrosine kinase with p34cdc2," *Cancer Res.*, 56:3617-3621, 1996.

Kufe et al., "Differential reactivity of a novel monoclonal antibody (DF3) with human malignant versus benign breast tumors," *Hybridoma*, 3:223-232, 1984.

Li et al., Human DF3/MUC1 carcinoma-associated protein functions as an oncogene *Oncogene*, 22:6107-6110, 2003.

Li et al., "Interaction of glycogen synthase kinase 3β with the DFC/MUC1 carcinoma-associated antigen and β-catenin," *Mol. Cell. Biol.*, 18:7216-7224, 1998.

Li et al., "The c-Src tyrosine kinase regulates signaling of the human DF3/MUC1 carcinoma-associated antigen with GSK3β and β-catenin," *J. Biol. Chem.*, 276:6061-6064, 2001.

Li et al., "The epidermal growth factor receptor regulates interaction of the human DF3/MUC1 carcinoma antigen with c-Src and beta-catenin," *J. Biol. Chem.*, 276:35239-42, 2001.

Makris et al., "The carboxyl-terminal region of IkappaB kinase gamma (IKKgamma) is required for full IKK activation," *Mol. Cell. Biol.*, 22:6573-6581, 2002.

May et al., "Selective inhibition of NF-kappaB activation by a peptide that blocks the interaction of NEMO with the IkappaB kinase complex," *Science*, 289:1550-1554, 2000.

McPherson, "Crystallization of proteins from polyethylene glycol," *J. Biol. Chem.*, 251:6300-6306, 1976.

Merlo et al., "Frequent alteration of the DF3 tumor-associated antigen gene in primary human breat carcinomas," *Cancer Res.*, 49:6966-6971, 1989.

Muthuswamy et al., "ErbB2, but not ErbB 1, reinitiates proliferation and induces luminal repopulation in epithelial acini," *Nat. Cell Biol.*, 3:785-792, 2001.

Myers, "Will combinatorial chemistry deliver real medicines?," *Curr. Opin. Biotechnol.*, 8:701-707, 1997.

Navarrete et al., "Basiliolides, a class of tetracyclic C19 dilactones from Thapsia garganica, release Ca(2+) from the endoplasmic reticulum and regulate the activity of the transcription factors nuclear factor of activated T cells, nuclear factor-kappaB, and activator protein 1 in T lymphocytes," *J. Pharmacol. Exp. Ther.*, 319(1):422-30, 2006.

Raina et al. "The MUC1 oncoprotein activates the anti-apoptotic phosphoinositide 3-kinase/Akt and Bcl-xL pathways in rat 3Y1 fibroblasts," *J. Biol. Chem,.* 279:20607-20612, 2004.

Raina et al., "MUC1 oncoprotein blocks nuclear targeting of c-Abl in the apoptotic response to the DNA damage," *EMBO J.*, 25(16):3774-83, 2006.

Ren et al., "Human MUC1 carcinoma-associated protein confers resistance to genotoxic anticancer agents," *Cancer Cell*, 5:163-175, 2004.

Rothwarf et al., "IKK-gamma is an essential regulatory subunit of the IkappaB kinase complex," *Nature*, 395:297-300, 1998.

Siddiqui et al., "Isolation and sequencing of a cDNA coding for the human DF3 breast carcinoma-associated antigen," *Proc. Natl. Acad. Sci. USA*, 85:2320-2323, 1988.

Soule et al., "Isolation and characterization of a spontaneously immortalized human breast epithelial cell line, MUC-10," *Cancer Res.*, 50:6075-6086, 1990.

Treon et al., "Epidermal soluble MUC1 levels and decreased anti-MUC1 antibody levels in patients with multiple myeloma," *Blood*, 96(9):3147-3153, 2000.

Vodanovic-Jankovic et al., "NF-kappaB as a target for the prevention of graft-versus-host disease: comparative efficacy of bortezomib and PS-1145," *Blood*, 107(2):827-34, 2006.

Wei et al., "Human MUC1 oncoprotein regulates p53-responsive gene transcription in the genotoxic stress response," *Cancer Cell*, 7:167-178, 2005.

Yamamoto et al., "IkappaB kinases: key regulators of the NF-kappaB pathway," *Trends Biochem. Sci.*, 29:72-79, 2004.

Yin et al., "MUC1 oncoprotein activates the FOXO3a transcription factor in a survival response to oxidative stress," *Biol. Chem.*, 279:45721-45727, 2004.

Zhang et al., "Nucleic acid aptamers in human viral disease," *Arch. Immunol. Ther. Exp.*, 52:307-315, 2004.

\* cited by examiner

MTPGTQSPFFLLLLLTVLTVVTGSGHASSTPGGEKETSATQRSSVPSSTEKNAIPAPTTTK
SCRETFLKCFCRFINKGVFWASPILSSVSDVPFPFSAQSGAGVPGWGIALLVLVCVLVAL
AIVYLIALAVCQCRRKNYGQLDIFPARDTYHPMSEYPTYHTHGRYVPPSSTDRSPYEKVS
AGNGGSSLSYTNPAVAATSANL

FIG. 14A

CQCRRKNYGQLDIFPARDTYHPMSEYPTYHTHGRYVPPSSTDRSPYEKVSAGNGGSSLS
YTNPAVAATSANL

FIG. 14B

MERPPGLRPGAGGPWEMRERLGTGGFGNVCLYQHRELDLKIAIKSCRLELSTKNRERW
CHEIQIMKKLNHANVVKACDVPEELNILIHDVPLLAMEYCSGGDLRKLLNKPENCCGLK
ESQILSLLSDIGSGIRYLHENKIIHRDLKPENIVLQDVGGKIIHKIIDLGYAKDVDQGSLCTS
FVGTLQYLAPELFENKPYTATVDYWSFGTMVFECIAGYRPFLHHLQPFTWHEKIKKKDP
KCIFACEEMSGEVRFSSHLPQPNSLCSLIVEPMENWLQLMLNWDPQQRGGPVDLTLKQP
RCFVLMDHILNLKIVHILNMTSAKIISFLLPPDESLHSLQSRIERETGINTGSQELLSETGISL
DPRKPASQCVLDGVRGCDSYMVYLFDKSKTVYEGPFASRSLSDCVNYIVQDSKIQLPIIQ
LRKVWAEAVHYVSGLKEDYSRLFQGQRAAMLSLLRYNANLTKMKNTLISASQQLKAK
LEFFHKSIQLDLERYSEQMTYGISSEKMLKAWKEMEEKAIHYAEVGVIGYLEDQIMSLH
AEIMELQKSPYGRRQGDLMESLEQRAIDLYKQLKHRPSDHSYSDSTEMVKIIVHTVQSQ
DRVLKELFGHLSKLLGCKQKIIDLLPKVEVALSNIKEADNTVMFMQGKRQKEIWHLLKI
ACTQSSARSLVGSSLEGAVTPQTSAWLPPTSAEHDHSLSCVVTPQDGETSAQMIEENLN
CLGHLSTIIHEANEEQGNSMMNLDWSWLTE

FIG. 15A

MSWSPSLTTQTCGAWEMKERLGTGGFGNVIRWHNQETGEQIAIKQCRQELSPRNRERW
CLEIQIMRRLTHPNVVAARDVPEGMXNLAPNDLPLLAMEYCQGGDLRKYLNQFENCCG
LREGAILTLLSDIASALRYLHENRIIHRDLKPENIVLQQGEQRLIHKIIDLGYAKELDQGSL
CTSFVGTLQYLAPELLEQQKYTVTVDYWSFGTLAFECITGFRPFLPNWQPVQWHSKVR
QKSEVDIVVSEDLNGTVKFSSSLPYPNNLNSVLAERLEKWLQLMLWHPRQRGTDPTY
GPNGCFKALDDILNLKLVHILNMVTGTIHTYPVTEDESLQSLKARIQQDTGIPEEDQELL
QEAGLALIPDKPATQCISDGKLNEGHTLDMDLVFLFDNSKITYETQISPRPQPESVSCILQ
EPKRNLAFFQLRKVWGQVWHSIQTLKEDCNRLQQGQRAAMMNLLRNNSCLSKMKNS
MASMSQQLKAKLDFFKTSIQIDLEKYSEQTEFGITSDKLLLAWREMEQAVELCGRENEV
KLLVERMMALQTDIVDLQRSPMGRKQGGTLDDLEEQARELYRRLREKPRDQRTEGDSQ
EMVRLLLQAIQSFEKKVRVIYTQLSKTVVCKQKALELLPKVEEVVSLMNEDEKTVVRLQ
EKRQKELWNLLKIACSKVRGPVSGSPDSMNASRLSQPGQLMSQPSTASNSLPEPAKKSE
ELVAEAHNLCTLLENAIQDTVREQDQSFTALDWSWLQTEEEEHSCLEQAS

FIG. 15B

MNRHLWKSQLCEMVQPSGGPAADQDVLGEESPLGKPAMLHLPSEQGAPETLQRCLEEN
QELRDAIRQSNQILRERCEELLHFQASQREEKEFLMCKFQEARKLVERLGLEKLDLKRQ
KEQALREVEHLKRCQQQMAEDKASVKAQVTSLLGELQESQSRLEAATKECQALEGRAR
AASEQARQLESEREALQQQHSVQVDQLRMQGQSVEAALRMERQAASEEKRKLAQLQV
AYHQLFQEYDNHIKSSVVGSERKRGMQLEDLKQQLQQAEEALVAKQEVIDKLKEEAEQ
HKIVMETVPVLKAQADIYKADFQAERQAREKLAEKKELLQEQLEQLQREYSKLKASCQ
ESARIEDMRKRHVEVSQAPLPPAPAYLSSPLALPSQRRSPPEEPPDFCCPKCQYQAPDMD
TLQIHVMECIE

FIG. 15C

MFQAAERPQEWAMEGPRDGLKKERLLDDRHDSGLDSMKDEEYEQMVKELQEIRLEPQ
EVPRGSEPWKQQLTEDGDSFLHLAIIHEEKALTMEVIRQVKGDLAFLNFQNNLQQTPLH
LAVITNQPEIAEALLGAGCDPELRDFRGNTPLHLACEQGCLASVGVLTQSCTTPHLHSIL
KATNYNGHTCLHLASIHGYLGIVELLVSLGADVNAQEPCNGRTALHLAVDLQNPDLVS
LLLKCGADVNRVTYQGYSPYQLTWGRPSTRIQQQLGQLTLENLQMLPESEDEESYDTES
EFTEFTEDELPYDDCVFGGQRLTL

FIG. 15D

SEQUENCE LISTING

<160> NUMBER OF SEQ ID NOS: 14

<210> SEQ ID NO 1
<211> LENGTH: 203
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Ile Pro Ala Pro Thr Thr Lys Ser Cys Arg
    50                  55                  60

Glu Thr Phe Leu Lys Cys Phe Cys Arg Phe Ile Asn Lys Gly Val Phe
65                  70                  75                  80

Trp Ala Ser Pro Ile Leu Ser Val Ser Asp Val Pro Phe Pro Phe
                85                  90                  95

Ser Ala Gln Ser Gly Ala Gly Val Pro Gly Trp Gly Ile Ala Leu Leu
            100                 105                 110

Val Leu Val Cys Val Leu Val Ala Leu Ala Ile Val Tyr Leu Ile Ala
        115                 120                 125

Leu Ala Val Cys Gln Cys Arg Arg Lys Asn Tyr Gly Gln Leu Asp Ile
    130                 135                 140

Phe Pro Ala Arg Asp Thr Tyr His Pro Met Ser Glu Tyr Pro Thr Tyr
145                 150                 155                 160

His Thr His Gly Arg Tyr Val Pro Pro Ser Ser Thr Asp Arg Ser Pro
                165                 170                 175

Tyr Glu Lys Val Ser Ala Gly Asn Gly Gly Ser Ser Leu Ser Tyr Thr
            180                 185                 190

Asn Pro Ala Val Ala Ala Thr Ser Ala Asn Leu
        195                 200

<210> SEQ ID NO 2
<211> LENGTH: 72
<212> TYPE: PRT
<213> ORGANISM: Homo sapiens

<400> SEQUENCE: 2

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Thr Ser Ala Asn Leu
65                  70

<210> SEQ ID NO 3
<211> LENGTH: 45
<212> TYPE: PRT
<213> ORGANISM: Homo sapiens

```
<400> SEQUENCE: 3

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro
        35                  40                  45

<210> SEQ ID NO 4
<211> LENGTH: 27
<212> TYPE: PRT
<213> ORGANISM: Homo sapiens

<400> SEQUENCE: 4

Tyr Glu Lys Val Ser Ala Gly Asn Gly Gly Ser Ser Leu Ser Tyr Thr
1               5                   10                  15

Asn Pro Ala Val Ala Ala Thr Ser Ala Asn Leu
            20                  25

<210> SEQ ID NO 5
<211> LENGTH: 745
<212> TYPE: PRT
<213> ORGANISM: Homo sapiens

<400> SEQUENCE: 5

Met Glu Arg Pro Pro Gly Leu Arg Pro Gly Ala Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
                245                 250                 255
```

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Ala Val Thr Pro Gln Thr Ser Ala Trp Leu Pro Pro Thr Ser Ala

```
                 675                 680                 685
Glu His Asp His Ser Leu Ser Cys Val Val Thr Pro Gln Asp Gly Glu
690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Gln Gly Asn Ser Met Met
                725                 730                 735

Asn Leu Asp Trp Ser Trp Leu Thr Glu
                740                 745

<210> SEQ ID NO 6
<211> LENGTH: 756
<212> TYPE: PRT
<213> ORGANISM: Homo sapiens
<220> FEATURE:
<221> NAME/KEY: VARIANT
<222> LOCATION: 84
<223> OTHER INFORMATION: Xaa = any amino acid

<400> SEQUENCE: 6

Met Ser Trp Ser Pro Ser Leu Thr Thr Gln Thr Cys Gly Ala Trp Glu
  1               5                  10                  15

Met Lys Glu Arg Leu Gly Thr Gly Gly Phe Gly Asn Val Ile Arg Trp
                 20                  25                  30

His Asn Gln Glu Thr Gly Glu Gln Ile Ala Ile Lys Gln Cys Arg Gln
             35                  40                  45

Glu Leu Ser Pro Arg Asn Arg Glu Arg Trp Cys Leu Glu Ile Gln Ile
         50                  55                  60

Met Arg Arg Leu Thr His Pro Asn Val Val Ala Ala Arg Asp Val Pro
 65                  70                  75                  80

Glu Gly Met Xaa Asn Leu Ala Pro Asn Asp Leu Pro Leu Leu Ala Met
                 85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285
```

```
Gly Thr Asp Pro Thr Tyr Gly Pro Asn Gly Cys Phe Lys Ala Leu Asp
290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415

Pro Lys Arg Asn Leu Ala Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510

Ala Trp Arg Glu Met Glu Gln Ala Val Glu Leu Cys Gly Arg Glu Asn
        515                 520                 525

Glu Val Lys Leu Leu Val Glu Arg Met Met Ala Leu Gln Thr Asp Ile
530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
        675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720
```

-continued

```
Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu His Ser Cys Leu
        740                 745                 750

Glu Gln Ala Ser
        755

<210> SEQ ID NO 7
<211> LENGTH: 458
<212> TYPE: PRT
<213> ORGANISM: Homo sapiens
<220> FEATURE:
<221> NAME/KEY: VARIANT
<222> LOCATION: 84
<223> OTHER INFORMATION: Xaa = any amino acid

<400> SEQUENCE: 7

Met Ser Trp Ser Pro Ser Leu Thr Thr Gln Thr Cys Gly Ala Trp Glu
  1               5                  10                  15

Met Lys Glu Arg Leu Gly Thr Gly Gly Phe Gly Asn Val Ile Arg Trp
             20                  25                  30

His Asn Gln Glu Thr Gly Glu Gln Ile Ala Ile Lys Gln Cys Arg Gln
         35                  40                  45

Glu Leu Ser Pro Arg Asn Arg Glu Arg Trp Cys Leu Glu Ile Gln Ile
     50                  55                  60

Met Arg Arg Leu Thr His Pro Asn Val Val Ala Ala Arg Asp Val Pro
 65                  70                  75                  80

Glu Gly Met Xaa Asn Leu Ala Pro Asn Asp Leu Pro Leu Leu Ala Met
                 85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
```

```
                305                 310                 315                 320
Thr Ile His Thr Tyr Pro Val Thr Glu Asp Glu Ser Leu Gln Ser Leu
                    325                 330                 335
Lys Ala Arg Ile Gln Gln Asp Thr Gly Ile Pro Glu Glu Asp Gln Glu
                340                 345                 350
Leu Leu Gln Glu Ala Gly Leu Ala Leu Ile Pro Asp Lys Pro Ala Thr
            355                 360                 365
Gln Cys Ile Ser Asp Gly Lys Leu Asn Glu Gly His Thr Leu Asp Met
        370                 375                 380
Asp Leu Val Phe Leu Phe Asp Asn Ser Lys Ile Thr Tyr Glu Thr Gln
385                 390                 395                 400
Ile Ser Pro Arg Pro Gln Pro Glu Ser Val Ser Cys Ile Leu Gln Glu
                405                 410                 415
Pro Lys Arg Asn Leu Ala Phe Phe Gln Leu Arg Lys Val Trp Gly Gln
                420                 425                 430
Val Trp His Ser Ile Gln Thr Leu Lys Glu Asp Cys Asn Arg Leu Gln
                435                 440                 445
Gln Gly Gln Arg Ala Ala Met Met Asn Leu
        450                 455

<210> SEQ ID NO 8
<211> LENGTH: 419
<212> TYPE: PRT
<213> ORGANISM: Homo sapiens

<400> SEQUENCE: 8

Met Asn Arg His Leu Trp Lys Ser Gln Leu Cys Glu Met Val Gln Pro
1               5                   10                  15
Ser Gly Gly Pro Ala Ala Asp Gln Asp Val Leu Gly Glu Glu Ser Pro
                20                  25                  30
Leu Gly Lys Pro Ala Met Leu His Leu Pro Ser Glu Gln Gly Ala Pro
            35                  40                  45
Glu Thr Leu Gln Arg Cys Leu Glu Glu Asn Gln Glu Leu Arg Asp Ala
        50                  55                  60
Ile Arg Gln Ser Asn Gln Ile Leu Arg Glu Arg Cys Glu Glu Leu Leu
65                  70                  75                  80
His Phe Gln Ala Ser Gln Arg Glu Glu Lys Glu Phe Leu Met Cys Lys
                85                  90                  95
Phe Gln Glu Ala Arg Lys Leu Val Glu Arg Leu Gly Leu Glu Lys Leu
                100                 105                 110
Asp Leu Lys Arg Gln Lys Glu Gln Ala Leu Arg Glu Val Glu His Leu
            115                 120                 125
Lys Arg Cys Gln Gln Gln Met Ala Glu Asp Lys Ala Ser Val Lys Ala
        130                 135                 140
Gln Val Thr Ser Leu Leu Gly Glu Leu Gln Glu Ser Gln Ser Arg Leu
145                 150                 155                 160
Glu Ala Ala Thr Lys Glu Cys Gln Ala Leu Glu Gly Arg Ala Arg Ala
                165                 170                 175
Ala Ser Glu Gln Ala Arg Gln Leu Glu Ser Glu Arg Glu Ala Leu Gln
                180                 185                 190
Gln Gln His Ser Val Gln Val Asp Gln Leu Arg Met Gln Gly Gln Ser
            195                 200                 205
Val Glu Ala Ala Leu Arg Met Glu Arg Gln Ala Ser Glu Glu Lys
        210                 215                 220
Arg Lys Leu Ala Gln Leu Gln Val Ala Tyr His Gln Leu Phe Gln Glu
```

```
                225                 230                 235                 240
Tyr Asp Asn His Ile Lys Ser Ser Val Val Gly Ser Glu Arg Lys Arg
                    245                 250                 255
Gly Met Gln Leu Glu Asp Leu Lys Gln Gln Leu Gln Gln Ala Glu Glu
                260                 265                 270
Ala Leu Val Ala Lys Gln Glu Val Ile Asp Lys Leu Lys Glu Glu Ala
                275                 280                 285
Glu Gln His Lys Ile Val Met Glu Thr Val Pro Val Leu Lys Ala Gln
                290                 295                 300
Ala Asp Ile Tyr Lys Ala Asp Phe Gln Ala Glu Arg Gln Ala Arg Glu
305                 310                 315                 320
Lys Leu Ala Glu Lys Lys Glu Leu Leu Gln Glu Gln Leu Glu Gln Leu
                325                 330                 335
Gln Arg Glu Tyr Ser Lys Leu Lys Ala Ser Cys Gln Glu Ser Ala Arg
                340                 345                 350
Ile Glu Asp Met Arg Lys Arg His Val Glu Val Ser Gln Ala Pro Leu
                355                 360                 365
Pro Pro Ala Pro Ala Tyr Leu Ser Ser Pro Leu Ala Leu Pro Ser Gln
370                 375                 380
Arg Arg Ser Pro Pro Glu Glu Pro Pro Asp Phe Cys Cys Pro Lys Cys
385                 390                 395                 400
Gln Tyr Gln Ala Pro Asp Met Asp Thr Leu Gln Ile His Val Met Glu
                405                 410                 415
Cys Ile Glu

<210> SEQ ID NO 9
<211> LENGTH: 223
<212> TYPE: PRT
<213> ORGANISM: Homo sapiens

<400> SEQUENCE: 9

Val Gln Val Asp Gln Leu Arg Met Gln Gly Gln Ser Val Glu Ala Ala
1               5                   10                  15
Leu Arg Met Glu Arg Gln Ala Ala Ser Glu Glu Lys Arg Lys Leu Ala
                20                  25                  30
Gln Leu Gln Val Ala Tyr His Gln Leu Phe Gln Glu Tyr Asp Asn His
            35                  40                  45
Ile Lys Ser Ser Val Val Gly Ser Glu Arg Lys Arg Gly Met Gln Leu
        50                  55                  60
Glu Asp Leu Lys Gln Gln Leu Gln Gln Ala Glu Glu Ala Leu Val Ala
65                  70                  75                  80
Lys Gln Glu Val Ile Asp Lys Leu Lys Glu Glu Ala Glu Gln His Lys
                85                  90                  95
Ile Val Met Glu Thr Val Pro Val Leu Lys Ala Gln Ala Asp Ile Tyr
                100                 105                 110
Lys Ala Asp Phe Gln Ala Glu Arg Gln Ala Arg Glu Lys Leu Ala Glu
            115                 120                 125
Lys Lys Glu Leu Leu Gln Glu Gln Leu Gln Leu Arg Glu Tyr
        130                 135                 140
Ser Lys Leu Lys Ala Ser Cys Gln Glu Ser Ala Arg Ile Glu Asp Met
145                 150                 155                 160
Arg Lys Arg His Val Glu Val Ser Gln Ala Pro Leu Pro Pro Ala Pro
                165                 170                 175
Ala Tyr Leu Ser Ser Pro Leu Ala Leu Pro Ser Gln Arg Arg Ser Pro
                180                 185                 190
```

Pro Glu Glu Pro Pro Asp Phe Cys Cys Pro Lys Cys Gln Tyr Gln Ala
                195                 200                 205

Pro Asp Met Asp Thr Leu Gln Ile His Val Met Glu Cys Ile Glu
    210                 215                 220

<210> SEQ ID NO 10
<211> LENGTH: 317
<212> TYPE: PRT
<213> ORGANISM: Homo sapiens

<400> SEQUENCE: 10

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu Pro Gln Glu Val Pro Arg Gly Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu
305                 310                 315

<210> SEQ ID NO 11
<211> LENGTH: 21
<212> TYPE: DNA
<213> ORGANISM: Artificial Sequence

```
<220> FEATURE:
<223> OTHER INFORMATION: Primer

<400> SEQUENCE: 11
agtcctgcac caccccgcac c                                            21

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ctccggtcgc agactgcaat act                                          23

<210> SEQ ID NO 13
<211> LENGTH: 10
<212> TYPE: PRT
<213> ORGANISM: Homo sapiens

<400> SEQUENCE: 13

Ser Ala Gly Asn Gly Gly Ser Ser Leu Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Mutation of the Serine rich motif from  human
      MUC1 CD

<400> SEQUENCE: 14

Ala Ala Gly Asn Gly Gly Ala Ala Ala Ala
1               5                   10
```

MUC1-IκB KINASE COMPLEXES AND THEIR ACTIVITIES

CROSS-REFERENCE TO RELATED APPLICATIONS

This application claims priority to U.S. Provisional Application No. 60/832,369, filed on Jul. 20, 2006, the contents of which are hereby incorporated by reference.

STATEMENT REGARDING FEDERALLY SPONSORED RESEARCH OR DEVELOPMENT

The research described in this application was supported by a grant from the National Cancer Institute of the National Institutes of Health (CA97098) and a grant from the U.S. Army (BC022158). Thus, the government has certain rights in the invention.

TECHNICAL FIELD

This invention relates to regulation of cell signaling, cell growth, and more particularly to the regulation of cancer cell growth.

BACKGROUND

The NF-κB proteins (RelA/p65, RelB, c-Rel, NF-κB1/p50 and NF-κB2/p52) are ubiquitously expressed transcription factors. In the absence of stimulation, NF-κB proteins localize to the cytoplasm in complexes with IκBα and other members of the IκB family of inhibitor proteins (Hayden et al. (2004) Genes Dev. 18:2195-2224). Phosphorylation of IκBα by the IκB kinases (IKKs; IKKα, IKKβ and IKKγ/NEMO) induces ubiquitination and degradation of IκBα and thereby release of NF-κB for nuclear translocation. Activation of NF-κB target genes contributes to tumor development through regulation of inflammatory responses, cellular proliferation and survival (Karin et al. (2002) Nat. Rev. Cancer 2:301-310). In the pro-carcinogenic classical pathway of NF-κB activation, IKKβ in a complex with the regulatory IKKγ subunit functions as the dominant kinase for phosphorylation of IkB proteins (Yamamoto et al. (2003) Trends Biochem. Sci. 29:72-79). Importantly, persistent activation of NF-κB has been described in diverse human malignancies, although the basis for this response is not known (Karin et al. (2002) Nat. Rev. Cancer 2:301-310).

The MUC1 heterodimeric mucin-type glycoprotein is expressed on the apical borders of secretory epithelial cells (Kufe et al. (1984) Hybridoma 3:223-232). With transformation and loss of polarity, MUC1 is expressed at high levels over the entire cell membrane and in the cytoplasm (Kufe et al. (1984) Hybridoma 3:223-232). The MUC1 N-terminal ectodomain, which consists of variable numbers of 20 amino acid tandem repeats that are extensively modified by O-linked glycans, is tethered to the cell surface through a complex with the MUC1 C-terminal transmembrane subunit (MUC1-C) (Siddiqui et al. (1988) Proc. Natl. Acad. Sci. USA 85:2320-2323; Gendler et al. (1988) J. Biol. Chem. 263:12820-12823; and Merlo et al. (1989) Cancer Res. 49:6966-6971). MUC1-C integrates receptor tyrosine kinase signaling with the Wnt pathway (Li et al. (1998) Mol. Cell. Biol. 18:7216-7224; Li et al. (2001) J. Biol. Chem. 276:35239-35242; and Li et al. (2001) J. Biol. Chem. 276:6061-6064). MUC1-C is also targeted to mitochondria and to the nucleus, where it contributes to the regulation of β-catenin/Tcf- and p53-mediated gene transcription (Ren et al. (2004) Cancer Cell 5:163-175; Huang et al. (2003) Cancer Biol. Ther. 2:702-706; and Wei et al. (2005) Cancer Cell 7:167-178). Overexpression of MUC1 is sufficient to induce transformation and to attenuate apoptosis in the response of cells to oxidative and genotoxic stress (Ren et al. (2004) Cancer Cell 5:163-175; Huang et al. (2003) Cancer Biol. Ther. 2:702-706; Li et al. (2003) Oncogene 22:6107-6110; Raina et al. (2004) J. Biol. Chem. 279:20607-20612; and Yin et al. (2004) J. Biol. Chem. 279:45721-45727).

SUMMARY

This invention is based, at least in part, on the discovery that MUC1 interacts with the NF-κB pathway by way of an interaction between MUC1 and IKK polypeptides.

In one aspect, the disclosure features a method of identifying a compound that inhibits binding of MUC1 (mucin 1) to an IKK. The method includes the steps of: (i) providing a MUC1 test agent; (ii) providing an IKK test agent that binds to the MUC1 test agent; (iii) contacting the MUC1 test agent with the IKK test agent in the presence of a test compound; and (iv) determining whether the test compound inhibits binding of the MUC1 test agent to the IKK test agent. The method can be performed (i.e., carried out) in a cell or in a cell-free system. In embodiments where the method is carried out in a cell, the cell can be a prokaryotic cell (e.g., a bacterial cell) or a eukaryotic cell (e.g., a yeast cell, a nematode cell, an insect cell, a bird cell, a mammalian cell (e.g., a mouse cell, a rat cell, a guinea pig cell, a horse cell, a cow cell, a pig cell, a goat cell, a donkey cell, a monkey cell, or a human cell)). MUC1 test agents can include any agent containing a full-length, wild-type, mature MUC1 or the MUC1-cytoplasmic domain (MUC1-CD), or fragments (e.g., functional fragments) of the full-length, wild-type, MUC1 or MUC1-CD as described herein. Examples of such MUC1-CD fragments include, MUC1-CD(1-45) (SEQ ID NO:3) and MUC1-CD (46-72) (SEQ ID NO:4). The IKK test agent of the method can include any full-length, wild-type IKK (e.g., IKKα, IKKβ, and IKKγ) or a MUC1-binding fragment (i.e., a functional fragment) of the IKKs. Examples of suitable IKK fragments include IKKβ (1-458) (SEQ ID NO:7) and IKKγ (197-419) (SEQ ID NO:9).

In another aspect, the disclosure provides a method of generating a compound that inhibits the interaction between MUC1 and an IKK polypeptide. The method includes the steps of: (i) providing the three-dimensional structure of a molecule comprising: (a) the cytoplasmic domain of MUC1 or an IKK polypeptide-binding fragment thereof; or (b) a molecule comprising an IKK polypeptide or MUC1-binding fragment thereof; (ii) designing, based on the three dimensional structure, a compound comprising a region that inhibits the interaction between MUC1 and the IKK polypeptide; and (iii) producing the compound. The method can further include the step of determining whether the compound identified in the method inhibits the interaction between MUC1 and an IKK polypeptide. IKK-binding fragments of MUC1 can include, or be, any fragment containing the MUC1-cytoplasmic domain (MUC1-CD), or fragments (e.g., functional fragments) of the MUC1-CD as described herein. Examples of such MUC1-CD fragments include, MUC1-CD(1-45) (SEQ ID NO:3), MUC1-CD(46-72) (SEQ ID NO:4), and MUC1-CDSRM (SEQ ID NO:13). The IKK molecule of the method can include, or be, any full-length, wild-type, IKK (e.g., IKKα, IKKβ, and IKKγ). Examples of MUC1-binding fragments (i.e., a functional fragment) of an IKK useful for the method include IKK fragments, e.g., IKKβ (1-458) (SEQ ID NO:7) and IKKγ (197-419) (SEQ ID NO:9).

In yet another aspect, the disclosure features a process of manufacturing a compound. The process includes the steps of: performing the method of generating a compound (as described above in the preceding paragraph), and after determining that the compound inhibits the interaction between MUC1 and the IKK polypeptide, manufacturing the compound.

In another aspect, the disclosure features a compound identified by any of the methods described above or a pharmaceutical composition comprising the compound and a pharmaceutically acceptable carrier.

In another aspect, the disclosure provides an in vitro method of inhibiting the interaction between MUC1 and an IKK. The method involves: optionally identifying a cancer cell as expressing MUC1, and culturing the cell with a compound that inhibits the interaction between MUC1 and an IKK. The cell can be a mammalian cell (e.g., a mouse cell, a rat cell, a guinea pig cell, a horse cell, a cow cell, a pig cell, a goat cell, a donkey cell, a monkey cell, or a human cell (e.g., a cell from a human patient)). The cancer cell can be a cell from a cancer including, but not limited to: lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer. The IKK of the method can include, or be, any full-length, wild-type, IKK (e.g., IKKα, IKKβ, and IKKγ). In some embodiments, the compound can be one identified in any of the methods described above.

In yet another aspect, the disclosure features an in vitro method of inhibiting NF-κB. The method includes the steps of: optionally identifying a cell as expressing MUC1, and culturing the cell with a compound that inhibits NF-κB. Inhibition of NF-κB can be, for example, inhibition of the expression of NF-κB, inhibition of NF-κB trans-activation activity (i.e., the NF-κB transcription factor activity), or inhibition of the sub-cellular localization of NF-κB (e.g., inhibition of nuclear localization of NF-κB). A compound useful for the method includes any compound described herein (e.g., a compound identified using the above method) or any other compound with appropriate NF-κB inhibitory activity (i.e., an NF-κB inhibitor, see below). The cell can be any mammalian cell (e.g., a mouse cell, a rat cell, a guinea pig cell, a horse cell, a cow cell, a pig cell, a goat cell, a donkey cell, a monkey cell, or a human cell (e.g., a cell from a human patient)). The cell can also be a cancer cell (e.g., a cell from a cancer selected from the group including: lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer). The cell can also endogenously express MUC1 (i.e., the genome of the cell contains a nucleic acid sequence encoding a MUC1 polypeptide), or the cell can express an exogenous or recombinant MUC1 (e.g., a cell transfected with an expression vector encoding a MUC1 polypeptide). The expression of MUC1 by a cell can be expression of MUC1 mRNA or MUC1 protein by the cell.

In another aspect, the disclosure provides a method of inhibiting an IKK. The method includes: optionally identifying a cell as expressing MUC1, and culturing the cell with a compound that inhibits an IKK. The IKK of the method can be any full-length, wild-type, IKK (e.g., IKKα, IKKβ, and IKKγ). Inhibition of an IKK can be inhibition of IKK expression (e.g., inhibition of the expression of IKK mRNA or IKK protein), inhibition of the kinase activity of an IKK, or inhibition of the sub-cellular localization of an IKK. A compound useful for the method can be any compound described herein (e.g., a compound identified using the above method) or any other compound with appropriate IKK inhibitory activity (i.e., an IKK inhibitor, see below). The cell can be any mammalian cell (e.g., a mouse cell, a rat cell, a guinea pig cell, a horse cell, a cow cell, a pig cell, a goat cell, a donkey cell, a monkey cell, or a human cell (e.g., a cell from a human patient)). The cell can also be a cancer cell (e.g., a cell from a cancer selected from the group including: lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer). The cell can also endogenously express MUC1 (i.e., the genome of the cell contains a nucleic acid sequence encoding a MUC1 polypeptide), or the cell can express an exogenous or recombinant MUC1 (e.g., a cell transfected with an expression vector encoding a MUC1 polypeptide). The expression of MUC1 by cell can be expression of MUC1 mRNA or MUC1 protein by the cell.

In another aspect, the disclosure features an in vitro method of inhibiting the interaction between MUC1 and an IKK. The method includes the steps of: providing a MUC1 polypeptide, providing an IKK polypeptide, and contacting the MUC1 polypeptide and the IKK polypeptide in the presence of a compound that inhibits the interaction between the MUC1 polypeptide and the IKK polypeptide. MUC1 polypeptides can include any polypeptide containing the full-length MUC1 polypeptide or MUC1-cytoplasmic domain (MUC1-CD), or fragments (e.g., functional fragments) of MUC1 or the MUC1-CD as described herein. Examples of such MUC1-CD fragments include, MUC1-CD(1-45) (SEQ ID NO:3) and MUC1-CD(46-72) (SEQ ID NO:4). The IKK polypeptides of the method can include any full-length, wild-type IKK (e.g., IKKα, IKKβ, and IKKγ) polypeptide or a MUC1-binding fragment (i.e., a functional fragment) of the IKK polypeptide. Examples of suitable IKK polypeptide fragments include IKKβ (1-458) (SEQ ID NO:7) and IKKγ (197-419) (SEQ ID NO:9). A compound useful for the method can be any compound described herein (e.g., a compound identified using the above method) or any other compound with appropriate IKK inhibitory activity (i.e., an IKK inhibitor, see below). The compound can also contain, or be, a small molecule, an antibody, an antibody fragment, a peptide, or a peptidomimetic.

In another aspect, the disclosure provides a method of treating a subject having, suspected of having, or is at risk of developing, a cancer. The method includes the steps of: optionally identifying a subject as having, suspected of having, or at risk of developing, a cancer comprising one or more cancer cells expressing MUC1, and delivering to the subject a composition comprising a compound that inhibits the interaction between MUC1 and an IKK. Expression of MUC1 by a cancer cell can be the expression of MUC1 mRNA or MUC1 protein by the cancer cell. The IKK of the method can be any full-length, wild-type, IKK (e.g., IKKα, IKKβ, and IKKγ). The subject can be any mammalian subject (e.g., a mouse, a rat, a guinea pig, a horse, a cow, a pig, a goat, a donkey, a monkey, or a human (e.g., a human patient)). The one or more cancer cells can be one or more cells from a cancer selected from the group including: lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer. The subject can also be a subject having a chronically inflamed tissue or organ, or a subject producing an elevated level of one or more inflammatory cytokines (e.g., Tumor Necrosis Factor alpha (TNFα)). A compound useful for the method can be any compound described herein (e.g., a compound identified using the above method) or any other compound that inhibits the interaction between MUC1 and an IKK. A compound useful in the method can contain, or be, a small molecule, an antibody, an antibody fragment, a polypeptide, or a peptidomimetic. The compound can also contain, or be, one or more fragments or functional fragments of MUC1 or the MUC1-CD, or an IKK. MUC1 fragments can include the MUC1-cytoplasmic domain (MUC1-CD), or fragments (e.g., functional fragments) of the MUC1-CD (e.g., MUC1-CD(1-45) (SEQ ID NO:3), MUC1-CD(46-72) (SEQ ID NO:4), or MUC1-CD-SRM (SEQ ID NO:13)). The fragments of an IKK can include fragments such as IKKβ (1-458) (SEQ ID NO:7) and IKKγ (197-419) (SEQ ID NO:9). When the compound is a peptide, the method can further include the step of administering to the subject a nucleic acid comprising a nucleotide sequence encoding the polypeptide, the nucleotide sequence being operably-linked to a transcriptional regulatory sequence. The nucleic acid can be an isolated nucleic acid or a nucleic acid in a recombinant cell transfected with the nucleic acid and secreting the polypeptide. The recombinant cell can be a transfected cell, or the progeny of a cell, made by transfecting a cell derived from the subject. As used herein, a "cell derived from a subject" is a cell obtained directly from the subject or the progeny of a cell obtained from the subject.

In some embodiments, the method can further include delivering one or more additional anti-cancer therapies to the subject. The one or more additional cancer therapies can include one or more chemotherapeutic agents, one or more forms of ionizing radiation, or one or more forms of hormonal therapy. The one or more additional chemotherapeutic agents can be cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, trastuzumab (e.g., Herceptin®), and an analog of any of the aforementioned.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC), has been exposed to conditions, or is presently affected by conditions, that can result in cancer. Thus, a subject can also be one "at risk of developing a cancer" when the subject has been exposed to mutagenic or carcinogenic levels of certain compounds (e.g., carcinogenic compounds in cigarette smoke such as acrolein, 4-aminobiphenyl, aromatic amines, benzene, benz{a}anthracene, benzo{a}pyrene, formaldehyde, hydrazine, Polonium-210 (Radon), urethane, or vinyl chloride). The subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. In addition, a subject can be "at risk of developing a cancer" when the subject suffers from an inflammation (e.g., chronic inflammation) such as an inflammatory bowel disease (e.g., Crohn's disease or ulcerative colitis) or any other inflammatory condition described herein. From the above it will be clear that subjects "at risk of developing a cancer" are not all the subjects within a species of interest.

A subject "suspected of having a cancer" is one having one or more symptoms of a cancer. Symptoms of cancer are well-known to those of skill in the art and include, without limitation, breast lumps, nipple changes, breast cysts, breast pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like. Types of cancers can include, e.g., lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

In yet another aspect, the disclosure features a method of treating a subject having, suspected of having, or at risk of developing, an inflammatory disorder such as an autoimmune disease. The method includes the steps of: optionally identifying a subject as having, suspected of having, or at risk of developing, an inflammatory condition (e.g., an autoimmune disease), where the subject has a site of inflammation, and the site of inflammation comprises immune cells, one or more of which express MUC1, and delivering to the subject a compound that inhibits the binding of MUC1 to an IKK. Expression of MUC1 by an immune cell can be the expression of MUC1 mRNA or MUC1 protein by the immune cell. The IKK of the method can be any full-length, wild-type, IKK (e.g., IKKα, IKKβ, and IKKγ). The subject can be any mammalian subject (e.g., a mouse, a rat, a guinea pig, a horse, a cow, a pig, a goat, a donkey, a monkey, or a human (e.g., a human patient)). A compound useful for the method includes any compound described herein (e.g., a compound identified using the above method) or any other compound that inhibits the interaction between MUC1 and an IKK. A compound useful in the method can contain a small molecule, an antibody, an antibody fragment, a polypeptide, or a peptidomimetic. The compound can also contain, or be, one or more fragments or functional fragments of MUC1 or the MUC1-CD, or an IKK. MUC1 fragments can include the MUC1-cytoplasmic domain (MUC1-CD), or fragments (e.g., functional fragments) of the MUC1-CD (e.g., MUC1-CD(1-45) (SEQ ID NO:3), MUC1-CD(46-72) (SEQ ID NO:4), or MUC1-CDSRM (SEQ ID NO:13)). The fragments of an IKK can include fragments such as IKKβ (1-458) (SEQ ID NO:7) and IKKγ (197-419) (SEQ ID NO:9).

In some embodiments, when the compound is a peptide, the method can further include the step of administering to the subject a nucleic acid comprising a nucleotide sequence encoding the polypeptide, the nucleotide sequence being operably-linked to a transcriptional regulatory sequence. The nucleic acid can be an isolated nucleic acid or a nucleic acid in a recombinant cell transfected with the nucleic acid and secreting the polypeptide. The recombinant cell can be a transfected cell, or the progeny of a cell, made by transfecting a cell derived from the subject.

As used herein, a subject "at risk of developing an inflammatory condition" refers to a subject with a family history of one or more inflammatory conditions (i.e., a genetic predisposition to one or more inflammatory conditions) or one exposed to one or more inflammation-inducing conditions. For example, a subject can have been exposed to a viral or bacterial superantigen such as, but not limited to, Staphylococcal enterotoxins (SEs), a *Streptococcus pyogenes* exotoxin (SPE), a *Staphylococcus aureus* toxic shock-syndrome toxin (TSST-1), a Streptococcal mitogenic exotoxin (SME) and a Streptococcal superantigen (SSA). From the above it will be clear that subjects "at risk of developing an inflammatory condition" are not all the subjects within a species of interest.

A subject "suspected of having an inflammatory condition" is one who presents with one or more symptoms of an inflammatory condition. Symptoms of inflammatory conditions are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain. An "inflammatory condition," as used herein, refers to a process in which one or more substances (e.g., substances not naturally occurring in the subject), via the action of white blood cells (e.g., B cells, T cells, macrophages, monocytes, or dendritic cells) inappropriately trigger a pathological response, e.g., a pathological immune response. Accordingly, such cells involved in the inflammatory response are referred to as "inflammatory cells." The inappropriately triggered inflammatory response can be one where no foreign substance (e.g., an antigen, a virus, a bacterium, a fungus) is present in or on the subject. The inappropriately triggered response can be one where a self-component (e.g., a self-antigen) is targeted (e.g., an autoimmune disorder such as multiple sclerosis) by the inflammatory cells. The inappropriately triggered response can also be an response that is inappropriate in magnitude or duration, e.g., anaphylaxis. Thus, the inappropriately targeted response can be due to the presence of a microbial infection (e.g., viral, bacterial, or fungal). Types of inflammatory conditions (e.g., autoimmune diseases) can include, but are not limited to, osteoarthritis, rheumatoid arthritis (RA), spondyloarthropathies, POEMS syndrome, inflammatory bowel diseases (e.g., Crohn's disease or ulcerative colitis), multicentric Castleman's disease, systemic lupus erythematosus (SLE), Goodpasture's syndrome, multiple sclerosis (MS), polymyalgia rheumatica, muscular dystrophy (MD), insulin-dependent diabetes mellitus (IDDM), dermatomyositis, polymyositis, inflammatory neuropathies such as Guillain Barre syndrome, vasculitis such as Wegener's granulomatosus, polyarteritis nodosa, polymyalgia rheumatica, temporal arteritis, Sjogren's syndrome, Bechet's disease, Churg-Strauss syndrome, or Takayasu's arteritis. Also included in inflammatory conditions are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory conditions can also include, e.g., asthma.

In another aspect, the disclosure features a method of treating a subject having, suspected of having, or is at risk of developing a cancer, the method comprising: optionally identifying a subject as having, suspected of having, or at risk of developing, a cancer comprising one or more cancer cells expressing MUC1, and delivering to the subject an NF-κB inhibitor. Expression of MUC1 by a cancer cell can be the expression of MUC1 mRNA or MUC1 protein by the cancer cell. The subject can be any mammalian subject (e.g., a mouse, a rat, a guinea pig, a horse, a cow, a pig, a goat, a donkey, a monkey, or a human (e.g., a human patient)). The one or more cancer cells can be one or more cells from a cancer selected from the group including: lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer. Inhibition of NF-κB can include, for example, inhibition of the expression of NF-κB, inhibition of NF-κB trans-activation activity (i.e., the NF-κB transcription factor activity), or inhibition of the sub-cellular localization of NF-κB (e.g., inhibition of nuclear localization of NF-κB). A compound useful for the method can be any compound described herein (e.g., a compound identified using the above method) or any other compound with appropriate NF-κB inhibitory activity (i.e., an NF-κB inhibitor, see below).

In another aspect, the disclosure features a method of inhibiting IκBα phosphorylation. The method includes the steps of: optionally identifying a subject as having, or at risk of developing, a cancer comprising one or more cancer cells expressing MUC1, and delivering to the subject a compound that inhibits IκBα phosphorylation. Expression of MUC1 by a cancer cell can be the expression of MUC1 mRNA or MUC1 protein by the cancer cell. The subject can be any mammalian subject (e.g., a mouse, a rat, a guinea pig, a horse, a cow, a pig, a goat, a donkey, a monkey, or a human (e.g., a human patient)). The one or more cancer cells can be one or more cells from a cancer selected from the group including: lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer. A compound useful for the method includes any compound described herein (e.g., a compound identified using the above method) or any other compound that inhibits the phosphorylation of IκBα.

In yet another aspect, the disclosure features a method of inhibiting an IKK. The method includes the steps of: optionally identifying a subject as having, or at risk of developing, a cancer comprising one or more cells expressing MUC1, and delivering to the subject a compound that inhibits an IKK. Expression of MUC1 by a cancer cell can be the expression of MUC1 mRNA or MUC1 protein by the cancer cell. The IKK can be IKKα, IKKβ, or IKKγ. Inhibition of an IKK can be inhibition of IKK expression (e.g., inhibition of the expression of IKK mRNA or IKK protein), inhibition of the kinase activity of an IKK, or inhibition of the sub-cellular localization of an IKK. A compound useful for the method can be any compound described herein (e.g., a compound identified using the above method) or any other compound with appropriate IKK inhibitory activity (i.e., an IKK inhibitor, see above).

In another aspect, the disclosure provides an in vivo method of inhibiting a viral infection-induced transformation of a cell. The method involves: optionally identifying a subject as a subject with one or more cells infected with a virus capable of transforming the one or more cells, wherein the one or more infected cells express MUC1, and delivering to the subject a compound that inhibits the interaction between MUC1 and an IKK. Expression of MUC1 by a virally-infected cell can be the expression of MUC1 mRNA or MUC1 protein by the virally-infected cell. The subject can be any mammalian subject (e.g., a mouse, a rat, a guinea pig, a horse, a cow, a pig, a goat, a donkey, a monkey, or a human (e.g., a human patient)). The virus can be a Herpes virus (e.g., Epstein-Barr virus), Papilloma virus (Human Papillomavirus (HPV)-16 or HPV-18), Papovavirus, a retrovirus, or Hepatitis virus (e.g., Hepatitis B Virus (HBV)). A compound useful for the method includes any compound described herein (e.g., a compound identified using the above method) or any other compound that inhibits the interaction between MUC1 and an IKK. A compound useful in the method can contain, or be, a small molecule, an antibody, an antibody fragment, a polypeptide, or a peptidomimetic. The compound can also contain, or be, one or more fragments or functional fragments of MUC1 or the MUC1-CD, or an IKK. MUC1 fragments can include the MUC1-cytoplasmic domain (MUC1-CD), or fragments (e.g., functional fragments) of the MUC1-CD (e.g., MUC1-CD(1-45) (SEQ ID NO:3), MUC1-CD(46-72) (SEQ ID NO:4), or MUC1-CDSRM (SEQ ID NO:13)). The fragments of an IKK can include, or be, fragments such as IKKβ (1-458) (SEQ ID NO:7) and IKKγ (197-419) (SEQ ID NO:9). When the compound is a polypeptide, the method can further include the step of administering to the subject a nucleic acid comprising a nucleotide sequence encoding the polypeptide, the nucleotide sequence being operably-linked to a transcriptional regulatory sequence. The nucleic acid can be an isolated nucleic acid or a nucleic acid in a recombinant cell transfected with the nucleic acid and secreting the polypeptide. The recombinant cell is a transfected cell, or the progeny of a cell, made by transfecting a cell derived from the subject.

In yet another aspect, the disclosure features a method of treating a subject having, or at risk of developing, an allogeneic immune response. The method includes the steps of: optionally identifying a subject as having, or at risk of developing, an allogenic immune response, where the subject has a site of inflammation, and the site of inflammation comprises immune cells, one or more of which express MUC1, and delivering to the subject a compound that inhibits the binding of MUC1 to an IKK. Expression of MUC1 by a cell can be the expression of MUC1 mRNA or MUC1 protein by the cell. The IKK of the method can be any full-length, wild-type, IKK (e.g., IKKα, IKKβ, and IKKγ). The subject can be any mammalian subject (e.g., a mouse, a rat, a guinea pig, a horse, a cow, a pig, a goat, a donkey, a monkey, or a human (e.g., a human patient)). A compound useful for the method includes any compound described herein (e.g., a compound identified using the above method) or any other compound that inhibits the interaction between MUC1 and an IKK. The allogeneic response can be a response to a transplanted tissue or organ (i.e., transplant rejection). A compound useful in the method can contain, or be, a small molecule, an antibody, an antibody fragment, a polypeptide, or a peptidomimetic. The compound can also contain, or be, one or more fragments or functional fragments of MUC1 or the MUC1-CD, or an IKK. MUC1 fragments can include the MUC1-cytoplasmic domain (MUC1-CD), or fragments (e.g., functional fragments) of the MUC1-CD (e.g., MUC1-CD(1-45) (SEQ ID NO:3), MUC1-CD(46-72) (SEQ ID NO:4), or MUC1-CDSRM (SEQ ID NO:13)). The fragments of an IKK can include, or be, fragments such as IKKβ (1-458) (SEQ ID NO:7) and IKKγ (197-419) (SEQ ID NO:9).

In some embodiments, when the compound is a polypeptide, the method can further include the step of administering to the subject a nucleic acid comprising a nucleotide sequence encoding the polypeptide, the nucleotide sequence being operably-linked to a transcriptional regulatory sequence. The nucleic acid can be an isolated nucleic acid or a nucleic acid in a recombinant cell transfected with the nucleic acid and secreting the polypeptide. The recombinant cell is a transfected cell, or the progeny of a cell, made by transfecting a cell derived from the subject.

In yet another aspect, the disclosure features a method for reducing the risk of (reducing the likelihood of or preventing the development of a cancer in a mammal. The method includes the step of administering to a subject a compound that (i) inhibits an interaction between MUC1 and an IKK; (ii) inhibits an IKK; (iii) inhibits phosphorylation of IκB; and/or (iv) inhibits NF-κB. The subject can be one at risk of developing a cancer. For example, the subject can have, be at risk of developing, or be suspected of having, an inflammatory condition mediated by one or more immune cells expressing MUC1 such as any of the inflammatory conditions described herein. The subject can also be one having, suspected of having, or at risk of developing a viral infection such as any of those described herein.

"Polypeptide" and "protein" are used interchangeably and refer to any peptide-linked chain of amino acids, regardless of length or post-translational modification. The MUC1, IKK molecules and test agents used in any of the methods of the invention can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required as that: (i) such variants of MUC1 have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type, full-length, mature MUC1 or MUC1-CD (cytoplasmic domain) to bind to an IKK (e.g., IKKα, IKKβ, or IKKγ); and (ii) such variants of an IKK have at least 25% (e.g., at least: 30%; 40%; 50%; 60%; 70%; 75%; 80%; 85%; 90%; 95%; 97%; 98%; 99%; 99.5%, or 100% or even greater) of the ability of the relevant wild-type, full-length IKK to bind to wild-type, full-length, mature MUC1 or MUC1-CD.

A "polypeptide fragment," as used herein, refers to a segment of the polypeptide that is shorter than a full-length, immature polypeptide. A "functional fragment" of a polypeptide has at least 30% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the activity of the mature, polypeptide. Fragments of a polypeptide include terminal as well internal deletion variants of a polypeptide. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

As used herein, an "IKK test agent" or "IKK polypeptide" contains, or is, (a) a full-length, wild-type IKK, (b) a functional fragment of an IKK polypeptide, or (c) (a) or (b) with not more than 50 (see above) conservative substitutions. As above, an IKK can be IKKα, IKKβ, or IKKγ. "MUC1-binding fragments," as used herein, refer to any IKK fragments that substantially retain the ability to bind MUC1 (i.e., that have at least 30% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length, wild-type IKK to bind to the cytoplasmic domain of MUC1).

"IKK test agents" or "IKK polypeptides" include internal or terminal (C or N) irrelevant or heterologous amino acid sequences (e.g., sequences derived from other proteins or synthetic sequences not corresponding to any naturally occurring protein). The sequences can be, for example, an antigenic tag (e.g., FLAG, polyhistidine, hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). Heterologous sequences can be of varying length and in some cases can be a larger sequences than the IKK polypeptide. Generally, the heterologous sequences are about 1-50 (e.g., two, four, eight, ten, 15, 20, 25, 30, 35, 40, or 45) amino acids in length. IKK test agents, other than full-length, wild-type IKK molecules, have at least 30% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length, wild-type IKK to bind to the cytoplasmic domain of MUC1.

As used herein, a "MUC1 test agent" or "MUC1 polypeptide" contains, or is, (a) full-length, wild-type mature MUC1, (b) a functional fragment of MUC1, or (c) (a) or (b) but with not more than 50 (see above) conservative substitutions. "MUC1 test agents" or "MUC1 polypeptides" include internal or terminal (C or N) irrelevant amino acid sequences (e.g., sequences derived from other proteins or synthetic sequences not corresponding to any naturally occurring protein) as described above for IKK test agents and IKK polypeptides.

Depending on their intended use, the polypeptides, test agents, or fragments of the polypeptides or test agents can be of any species such as, e.g., nematode, insect, plant, bird, fish, reptile, or mammal (e.g., a mouse, rat, rabbit, hamster, gerbil, dog, cat, goat, pig, cow, horse, whale, monkey, or human). In some embodiments, fragments can include immunogenic and antigenic fragments of the polypeptides or test agents. An immunogenic fragment is one that has at least 25% (e.g., at least: 30%; 40%; 50%; 60%; 70%; 75%; 80%; 85%; 90%; 95%; 97%; 98%; 99%; 99.5%, or 100% or even more) of the ability of the relevant full-length, wild-type protein to stimulate an immune response (e.g., an antibody response or a cellular immune response) in an animal of interest. An antigenic fragment of a protein is one having at least 25% (e.g., at least: 30%; 40%; 50%; 60%; 70%; 75%; 80%; 85%; 90%; 95%; 97%; 98%; 99%; 99.5%, or 100% or even greater) of the ability of the relevant full-length, wild-type polypeptide or test agent to be recognized by an antibody specific for the protein or a T cell specific to the protein.

As used herein, "MUC1 cytoplasmic domain" or MUC1-CD" refers to a 72 amino acid portion of the full-length MUC1 (SEQ ID NO: 1) and is depicted in SEQ ID NO:2.

As used herein, "transformation" or "cellular transformation" refers to a change undergone by a mammalian cell, wherein the cell acquires one or more characteristics of a cancerous cell (e.g., anchorage-independent growth, uncontrolled growth, reversal of senescence, or metastatic potential). Cellular transformation can occur, e.g., as the result of an infection with a virus. Examples of viruses known to transform mammalian cells in culture or in vivo (e.g., in a mammalian subject) include those of Papillomavirus, Papovavirus, Herpes virus, and Adenovirus families. Cells can also be transformed through chronic inflammation, for example, cells involved in inflammatory conditions such as an inflammatory bowel disease (e.g., ulcerative colitis or Crohn's disease) or hepatitis (see, e.g., Beatty et al. (2007) J. Immunol. 179: 735-739).

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inhibiting survival of cancer cells, will be apparent from the following description, from the drawings and from the claims.

BRIEF DESCRIPTION OF THE DRAWINGS

FIG. 4C (bottom panel) is a photograph of an immunoblot and a photograph of a Coomassie blue-stained electrophoretic gel. GST- and the indicated GST-MUC1-CD fusion proteins bound to glutathione beads were incubated with purified IKKβ. The precipitates were immunoblotted with anti-IKKβ. Input of the GST and GST-MUC1-CD fusion proteins was assessed by Coomassie blue staining. The molecular weights of proteins (as indicated on the left of the photographs) are expressed as kilodaltons (kDa).

FIG. 14A is a depiction of an exemplary amino acid sequence for a human MUC1 polypeptide (SEQ ID NO:1).

FIG. 14B is a depiction of an exemplary amino acid sequence for a human MUC1 cytoplasmic domain (CD) polypeptide (SEQ ID NO:2).

FIG. 15A is a depiction of an exemplary amino acid sequence for a human IKKα polypeptide (SEQ ID NO:5).

FIG. 15B is a depiction of an exemplary amino acid sequence for a human IKKβ polypeptide (SEQ ID NO:6).

FIG. 15C is a depiction of an exemplary amino acid sequence for a human IKKγ polypeptide (SEQ ID NO:8).

FIG. 15D is a depiction of an exemplary amino acid sequence for a human IκBα polypeptide (SEQ ID NO: 10).

DETAILED DESCRIPTION

Methods of Screening for Inhibitory Compounds

Figure 1:
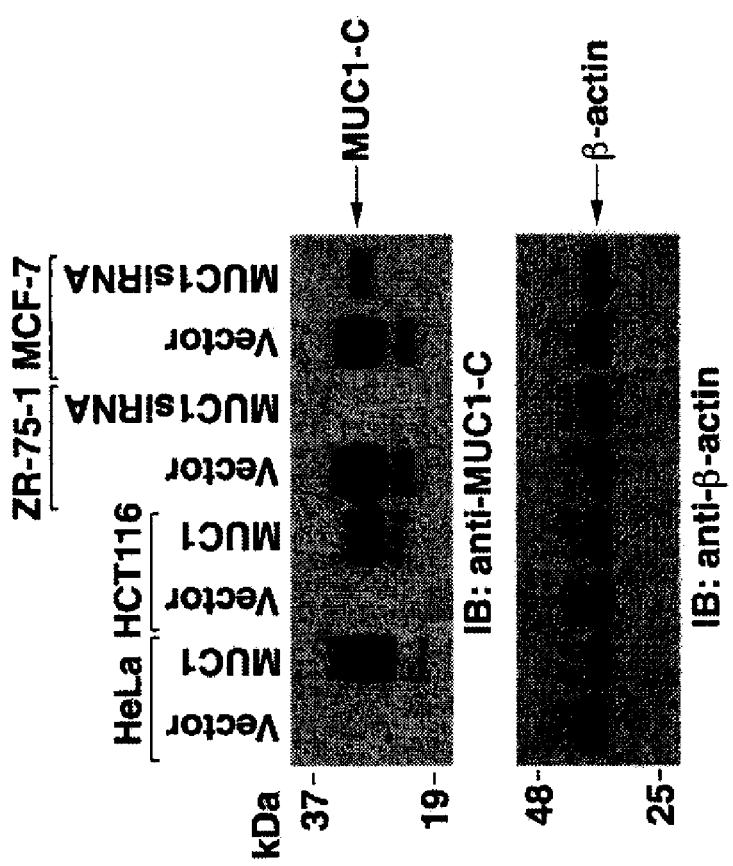
FIG. 1 is a pair of photographs of immunoblots showing the expression of exogenous and endogenous MUC1. Lysates from HeLa and HCT116 cells stably expressing an empty vector (Hela/Vector) or (HCT116/Vector) or exogenous MUC1 (HeLa/MUC1 or HCT116/MUC1) and from ZR-75-1 and MCF-7 cells silenced for MUC1 were immunoblotted (IB) with anti-MUC1-C and anti-β-actin antibodies. The molecular weights of proteins (as indicated on the left of the photographs) are expressed as kilodaltons (kDa).

The invention provides in vitro methods (e.g., "screening methods") for identifying compounds (e.g., small molecules or macromolecules) that inhibit binding of MUC1 to an IKK (i.e., IKKα, IKKβ, or IKKγ).

These methods can be performed using: (a) isolated MUC1 test agents and one or more isolated IKK test agents; or (b) cells expressing a MUC1 test agent and one or more IKK test agents.

MUC1 test agents can contain, or be, a MUC1-CD polypeptide or an IKK-binding fragment thereof. An exemplary amino acid sequence for a human MUC1 CD is as follows:

```
                                          (SEQ ID NO: 2)
CQCRRKNYGQLDIFPARDTYHPMSEYPTYHTHGRYVPPSSTDRSPYEKVS

AGNGGSSLSYTNPAVAATSANL.
```

IKK test agents can contain, or be, an IKKα, IKKβ, or IKKγ polypeptide or MUC1-binding fragments thereof. An exemplary amino acid sequence for a full length, wild-type, IKKα polypeptide is as follows:

```
                                          (SEQ ID NO: 5)
MERPPGLRPGAGGPWEMRERLGTGGFGNVCLYQHRELDLKIAIKSCRLEL

STKNRERWCHEIQIMKKLNHANVVKACDVPEELNILIHDVPLLAMEYCSG

GDLRKLLNKPENCCGLKESQILSLLSDIGSGIRYLHENKIIHRDLKPENI

VLQDVGGKIIHKIIDLGYAKDVDQGSLCTSFVGTLQYLAPELFENKPYTA

TVDYWSFGTMVFECIAGYRPFLHHLQPFTWHEKIKKKDPKCIFACEEMSG

EVRFSSHLPQPNSLCSLIVEPMENWLQLMLNWDPQQRGGPVDLTLKQPRC

FVLMDHILNLKIVHILNMTSAKIISFLLPPDESLHSLQSRIERETGINTG

SQELLSETGISLDPRKPASQCVLDGVRGCDSYMVYLFDKSKTVYEGPFAS

RSLSDCVNYIYQDSKIQLPIIQLRKVWAEAVHYVSGLKEDYSRLFQGQRA

AMLSLLRYNANLTKMKNTLISASQQLKAKLEFFHKSIQLDLERYSEQMTY

GISSEKMLKAWKEMEEKAIHYAEVGVIGYLEDQIMSLHAEIMELQKSPYG

RRQGDLMESLEQRAIDLYKQLKHRPSDHSYSDSTEMVKIIVHTVQSQDRV
```

-continued

```
LKELFGHLSKLLGCKQKIIDLLPKVEVALSNIKEADNTVMFMQGKRQKEI

WHLLKIACTQSSARSLVGSSLEGAVTPQTSAWLPPTSAEHDHSLSCVVTP

QDGETSAQMIEENLNCLGHLSTIIHEANEEQGNSMMNLDWSWLTE.
```

An exemplary amino acid sequence for an IKKβ polypeptide is as follows:

```
                                    (SEQ ID NO: 6)
MSWSPSLTTQTCGAWEMKERLGTGGFGNVIRWHNQETGEQIAIKQCRQEL

SPRNRERWCLEIQIMRRLTHPNVVAARDVPEGMXNLAPNDLPLLAMEYCQ

GGDLRKYLNQFENCCGLREGAILTLLSDIASALRYLHENRIIHRDLKPEN

IVLQQGEQRLIHKIIDLGYAKELDQGSLCTSFVGTLQYLAPELLEQQKYT

VTVDYWSFGTLAFECITGFRPFLPNWQPVQWHSKVRQKSEVDIVVSEDLN

GTVKFSSSLPYPNNLNSVLAERLEKWLQLMLMWHPRQRGTDPTYGPNGCF

KALDDILNLKLVHILNMVTGTIHTYPVTEDESLQSLKARIQQDTGIPEED

QELLQEAGLALLPDKPATQCISDGKLNEGHTLDMDLVFLFDNSKITYETQ

ISPRPQPESVSCILQEPKRNLAFFQLRKVWGQVWHSIQTLKEDCNRLQQG

QRAAMMNLLRNNSCLSKMIQ4SMASMSQQLKAKLDFFKTSIQIDLEKYSE

QTEFGITSDKLLLAWREMEQAVELCGRENEVKLLVERMMALQTDIVDLQR

SPMGRKQGGTLDDLEEQARELYRRLREKPRDQRTEGDSQEMVRLLLQAIQ

SFEKKVRVIYTQLSKTVVCKQKALELLPKVEEVVSLMNEDEKTVVRLQEK

RQKELWNLLKIACSKVRGPVSGSPDSMNASRLSQPGQLMSQPSTASNSLP

EPAKKSEELVAEAHNLCTLLENAIQDTVREQDQSFTALDWSWLQTEEEEH

SCLEQAS.
```

An exemplary amino acid sequence for an IKKγ polypeptide is as follows:

```
                                    (SEQ ID NO: 8)
MNRHLWKSQLCEMVQPSGGPAADQDVLGEESPLGKPAMLHLPSEQGAPET

LQRCLEENQELRDAIRQSNQILRERCEELLHFQASQREEKEFLMCKFQEA

RKLVERLGLEKLDLKRQKEQALREVEHLKRCQQQMAEDKASVKAQVTSLL

GELQEAQSRLEAATKECQALEGRARAASEQARQLESEREALQQQHSVQVD

QLRMQGQSVEAALRMERQAASEEKRKLAQLQVAYHQLFQEYDNHIKSSVV

GSERKRGMQLEDLKQQLQQAEEALVAKQEVIDKLKEEAEQHKIVMETVPV

LKAQADIYKADFQAERQAREKLAEKKELLQEQLEQLQREYSKLKASCQES

ARIEDMRXRHVEVSQAPLPPAPAYLSSPLALPSQRRSPPEEPPDFCCPKC

QYQAPDMDTLQIHVMECIE.
```

Exemplary IKK-binding or MUC1-binding fragments of a MUC1 or IKK polypeptide, respectively, for use as test agents in the methods are described above.

The term "isolated" as applied to any of the above-listed polypeptide test agents refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a test agent is at least 80%, more preferably at least 90%, and most preferably at least 99%, by dry weight, the test agent. Since a polypeptide that is chemically synthesized is, by its nature, separated from the components that naturally accompany it, a synthetic polypeptide test agent is "isolated."

An isolated polypeptide test agent can be obtained, for example, by extraction from a natural source (e.g., from tissues); by expression of a recombinant nucleic acid encoding the polypeptide; or by chemical synthesis. A polypeptide test agent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the test agents can undergo modification, e.g., phosphorylation or glycosylation, by methods known in the art.

In methods of screening for compounds that inhibit or enhance binding of an isolated MUC1 test agent to an isolated IKK test agent, a MUC1 test agent is contacted with an IKK test agent in the presence of one or more concentrations of a test compound and binding between the two test agents in the presence and absence of the test compound is detected and/or measured. In such assays neither of the test agents need be detectably labeled. For example, by exploiting the phenomenon of surface plasmon resonance, the MUC1 test agent can be bound to a suitable solid substrate and an IKK test agent exposed to the substrate-bound MUC1 test agent in the presence and absence of the compound of interest. Binding of the IKK test agent to the MUC1 test agent on the solid substrate results in a change in the intensity of surface plasmon resonance that can be detected qualitatively or quantitatively by an appropriate instrument, e.g., a Biacore apparatus (Biacore International AB, Rapsgatan, Sweden). It will be appreciated that the experiment can be performed in reverse, i.e., with the IKK test agent bound to the solid substrate and the MUC1 test agent added to it in the presence of the test compound.

Moreover, assays to test for inhibition (or in some cases enhancement) of binding of MUC1 to an IKK can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the IKK test agent can be immobilized on a solid substrate such as a nylon or nitrocellulose membrane by, for example, "spotting" an aliquot of a sample containing the test agent onto a membrane or by blotting onto a membrane an electrophoretic gel on which the sample or an aliquot of the sample has been subjected to electrophoretic separation. Alternatively, the IKK test agent can be bound to a plastic substrate (e.g., the plastic bottom of an ELISA (enzyme-linked immunosorbent assay) plate well) using methods known in the art. The substrate-bound test agent is then exposed to the MUC1 test agent in the presence and absence of the test compound. After incubating the resulting mixture for a period of time and at temperature optimized for the system of interest, the presence and/or amount of MUC1 test agent bound to the IKK test on the solid substrate is then assayed using a detection antibody that binds to the MUC1 test agent and, where required, appropriate detectably labeled secondary antibodies or avidin. It will be appreciated that instead of binding the IKK test agent to the solid substrate, the MUC1 test agent can be bound to it. In this case binding of the IKK test agent to the substrate-bound MUC1 is tested by obvious adaptions of the method described above for substrate-bound IKK test agent.

The invention also features "sandwich" assays. In these sandwich assays, instead of immobilizing test agents on solid substrates by the methods described above, an appropriate test agent can be immobilized on the solid substrate by, prior to exposing the solid substrate to the test agent, conjugating a "capture" test agent-specific antibody (polyclonal or mAb) to the solid substrate by any of a variety of methods known in the art. The test agent is then bound to the solid substrate by virtue of its binding to the capture antibody conjugated to the solid substrate. The procedure is carried out in essentially the same manner described above for methods in which the appropriate test agent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}$I, $^{131}$I, $^{35}$S, $^{3}$H, $^{32}$P, or $^{14}$C), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

Candidate compounds can also be tested for their ability to inhibit binding of MUC1 to an IKK in cells. The cells can either naturally express an appropriate MUC1 test agent and/ or an IKK test agent of interest (i.e., the cells encode an endogenous MUC1 and/or IKK gene which can be expressed to yield a MUC1 and/or IKK polypeptide) or they can recombinantly express either or both test agents. The cells can be normal or malignant and of any histological type, e.g., without limitation, epithelial cells, fibroblasts, lymphoid cells, macrophages/monocytes, granulocytes, keratinocytes, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., a death receptor ligand such as TNF α) prior to or after exposure of the cells to the compound. Following incubation of cells expressing the test agents of interest in the absence or presence (optionally at various concentrations), physical association between the test agents can be determined microscopically using appropriately labeled antibodies specific for both test agents, e.g., by confocal microscopy. Alternatively, the cells can be lysed under non-dissociating conditions and the lysates tested for the presence of physically associated test agents. Such methods include adaptions of those described using isolated test agents. For example, an antibody specific for one of the two test agents (test agent 1) can be bound to a solid substrate (e.g., the bottom and sides of the well of a microtiter plate or a nylon membrane). After washing away unbound antibody, the solid substrate with bound antibody is contacted with the cell lysate. Any test agent 1 in the lysate, bound or not bound to the second test agent (test agent 2), will bind to the antibody specific for test agent 1 on the solid substrate. After washing away unbound lysate components, the presence of test agent 2 (bound via test agent 1 and the antibody specific for test agent 1 to the solid substrate) is tested for using a detectably labeled antibody (see above) specific for test agent 2. Alternatively, test agent 1 can be immunoprecipitated with an antibody specific for test agent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any test agent 2 on the membrane detected and/or measured with a detectably labeled antibody (see above) specific for test agent 2 by any of the above-described methods. It is understood that in the above-described assays, test agent 1 can be either the MUC1 test agent or the IKK test agent or vice versa. The test compounds can bind to one or both of the MUC1 and IKK test agents.

Since the interaction between MUC1 and an IKK controls downstream signaling events in the NF-κB pathway, the ability of a candidate compound to inhibit an interaction between MUC1 and an IKK can also be tested using a secondary indicator. For example, secondary indicators of inhibition of an interaction between MUC1 and an IKK include, but are not limited to, inhibition of the kinase activity of an IKK, inhibition of IκB phosphorylation by an IKK, and/or inhibition of NF-κB (see below).

In a preferred embodiment, screening assays (in vivo or in vitro) can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay.

Methods of Inhibiting Binding of MUC1 to an IKK

The disclosure features a method of inhibiting binding of MUC1 to an IKK in a cell. The method involves introducing into a cell a compound that inhibits the binding of an IKK to the MUC1 (e.g., to the MUC1 CD). Prior to introduction of the compound into the cell, the cell (or another cancer cell from the subject from which the cell to be treated was obtained) can optionally be tested for MUC1 expression or expression of an IKK. This can be done by testing for expression of either MUC1 or IKK protein or MUC1 or IKK mRNA by any of a wide variety of methods known in the art.

The compound can be one identified by any of the methods described above. Examples of appropriate compounds include functional fragments of MUC1 or the MUC1-CD (e.g., MUC1-CD, MUC1-CD(1-45), MUC1-CD(46-72), MUC1-CDSRM), or functional fragments of an IKK (e.g., IKKβ (1-456) or IKKγ (197-419)). Such compounds are described below under "Inhibition of an IKK."

Peptide inhibitory compounds can contain up to 50 (e.g., one, two, three, four, five, six, seven, eight, nine, ten, 12, 15, 18, 20, 25, 30, 35, 40, 45, or 50) MUC1 or IKK residues or unrelated residues (e.g., heterologous sequences) on either end or on both ends of the MUC1 or IKK inhibitory segments.

Any MUC1 or IKK peptides to be used as inhibitor compounds can optionally have any phosphorylation-susceptible amino acid residues phosphorylated.

Any MUC1 or IKK peptides to be used as inhibitor compounds can optionally have any glycosylation-susceptible amino acid residues glycosylated. Glycosylation can either be N- or O-linked glycosylation.

Any MUC1 or IKK peptides to be used as inhibitor compounds can optionally have any cysteines, cable of forming disulfide linkages, involved as one member of disulfide bonding pair. Disulfide bonds can be intramolecular or intermolecular. Intermolecular disulfide bonds can occur between two like MUC1 or IKK polypeptides (i.e., homodimers) or between a MUC1 or IKK polypeptide and an additional polypeptides (i.e., heterodimers).

MUC1 peptide fragments useful as inhibitory compounds (or other inhibitory compounds (e.g., IKK-specific antibodies or antibody fragments) that act by binding to an IKK) will have substantially no MUC1 agonist activity, i.e., they will substantially lack the effects of MUC1 described herein that result from binding of MUC1 CD to IKK proteins. Compounds having substantially no MUC1 agonist activity are those having less than 20% (e.g., less than: 10%; 5%; 2%; 1%; 0.5%; 0.2%; 0.1%; 0.01%; 0.001%; or 0.0001%) of the ability of MUC1 CD to enhance the activation of the NF-κB pathway.

Similarly IKK peptide fragment compounds will have substantially none of the NF-κB-enhancing activity of IKK polypeptides. Thus, peptide fragments of an IKK useful as inhibitory compounds will generally either lack all or part of their kinase domain (or at least portions of the kinase domain which confer activity) or contain one or more mutations that render the kinase domain inactive. Methods of designing, making, and testing such compounds for the appropriate binding-inhibitory activity are known to those in the art.

In addition, the inhibitory compounds can be antibodies, or antigen-binding antibody fragments, specific for MUC1 or an IKK. Such antibodies will generally bind to, or close to: (a) the region of MUC1 to which an IKK binds; (b) or the region on an IKK to which MUC1 binds. However, as indicated above, the compounds can also act allosterically and so they can also bind to the proteins at positions other than, and even remote from, the binding sites for MUC1 (on an IKK) and on an IKK (for MUC1). As used throughout the present application, the term "antibody" refers to a whole antibody (e.g., IgM, IgG, IgA, IgD, or IgE) molecule that is generated by any one of a variety of methods that are known in the art. The antibody can be made in or derived from any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the methods described herein are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12):1121-1123; Hudson et al. (1999) J. Immunol. Methods 23(1-2):177-189, the disclosures of both of which are incorporated herein by reference in their entirety] and intrabodies [Huston et al. (2001) Hum. Antibodies 10(3-4): 127-142; Wheeler et al. (2003) Mol. Ther. 8(3):355-366; Stocks (2004) Drug Discov. Today 9(22): 960-966, the disclosures of all of which are incorporated herein by reference in their entirety] can be used in the methods described herein.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, 1 *Current Protocols In Immunology*, Coligan et al., ed. 2.8, 2.10 (Wiley Interscience, 1991) the disclosure of which is incorporated herein by reference in their entirety. scFv fragments can be produced, for example, as described in U.S. Pat. No. 4,642, 334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225, 539; Jones et al. (1986) Nature 321, 552-25; Veroeyan et al. (1988) Science 239, 1534; and Beidler et al. (1988) J. Immunol. 141, 4053-60. The disclosures of all these articles and patent documents are incorporated herein by reference in their entirety.

Cells to which the methods described herein can be applied include generally any cell that expresses MUC1 mRNA or MUC1 protein (e.g., endogenous or exogenous MUC1 mRNA or protein). Such cells include normal cells, such as any normal epithelial cell, or a cancer cell, whose proliferation it is desired to inhibit. An appropriate cancer cell can be a breast cancer, lung cancer, colon cancer, pancreatic cancer, renal cancer, stomach cancer, liver cancer, thyroid cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods described herein can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The methods can be performed in vitro, in vivo, or ex vivo. In vitro application of appropriate compounds can be useful, for example, in basic scientific studies of tumor cell biology, e.g., studies on the mechanism of action of MUC1 and/or an IKK in promoting tumor cell growth, including survival. In addition, the compounds that are inhibitory can be used as "positive controls" in methods to identify additional compounds with inhibitory activity (see above). In such in vitro methods, cells expressing MUC1 and one or more of an IKK, can be incubated for various times with the inhibitory compound(s) at a variety of concentrations. Other incubation conditions known to those in art (e.g., temperature, or cell concentration) can also be varied. Inhibition of binding can be tested by methods such as those disclosed herein.

MUC1 expression (e.g., elevated MUC1 expression) is associated with many cancers. Since the interaction of MUC1 with IKK polypeptides promotes phosphorylation of IκBα, and the subsequent release of the growth- and cell-survival-promoting transcription factor NF-κB, it is thought that inhibitors which block such an interaction would be useful in treating cancers. Thus, any of the compounds described herein (e.g., compounds that inhibit binding between MUC1 and an IKK) or any other compounds that possess appropriate inhibitory activity are generally useful as cancer cell (e.g., breast cancer cell) survival-inhibiting and/or cell cycle-arresting therapeutics or prophylactics. They can be administered to mammalian subjects (e.g., human cancer patients) alone or in conjunction with other drugs, radiotherapies, or hormonal therapies (e.g., administration to a subject of erythropoietin). For example, the compounds can be administered in combination (e.g., before, after, simultaneously, alternating administration) with other chemotherapeutics including certain types of ionizing radiation, or agents such as cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, trastuzumab (e.g., Herceptin®), and an analog of any of the aforementioned. The compounds can also be administered to subjects that are genetically and/or due to, for example, physiological and/or environmental factors, susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke). The compounds can also be administered to patients with certain viral infections (e.g., an infection with a Hepatitis virus, a Papillomavirus, a Papovavirus, or an Adenovirus) that are known, by those of skill in the art, to cause cellular transformation. Compounds may also be administered to subjects or patients with other forms of inflammation (e.g., a colitis or a gastritis) associated with cellular transformation (e.g., the promotion of the development of a cancer). As used herein, a compound that is "therapeutic" is a compound that causes a complete abolishment of the symptoms of a disease or a decrease in the severity of the symptoms of the disease. "Prevention" means that symptoms of the disease (e.g., cancer) are essentially absent. As used herein, "prophylaxis" means complete prevention of the symptoms of a disease, a delay in onset of the symptoms of a disease, or a lessening in the severity of subsequently developed disease symptoms.

Inflammatory conditions such as autoimmune diseases are known to be associated with elevated cellular NF-κB activity. MUC1 is also expressed (e.g., elevated MUC1 expression) in certain lymphoid tissues. Since the interaction of MUC1 with IKK polypeptides promotes the activation of NF-κB, it is thought that inhibitors which block such an interaction would be useful in treating autoimmune disorders. Thus, any of the compounds described herein (e.g., compounds that inhibit binding between MUC1 and an IKK) or any other compounds that possess appropriate inhibitory activity are also generally useful as therapies for the treatment of an autoimmune disease. Inflammatory conditions treatable by the compounds include, for example, RA, lupus erythematosus, MS, IDDM, Myasthenia gravis, scleroderma, Sjogren's syndrome, Goodpasture's syndrome, or any others described herein. Compounds can be administered to subjects (e.g., human lupus patients) alone or in conjunction with other drugs (e.g., immunosuppressive drugs), radiotherapy, or hormonal therapies. The compounds can also be administered to subjects that are genetically and/or due to, for example, physiological and/or environmental factors, susceptible to an inflammatory disorder, e.g., subjects with a family history of inflammatory disorders (e.g., lupus erythematosus or Sjogren's syndrome), subjects with chronic inflammation or subject to chronic stress, or subjects that are exposed to natural or non-natural environmental conditions that promote inflammation (e.g., excessive exposure to microbial pathogens, or certain immunogens such as pollen, asbestos, or smoke (lung inflammations)).

Any of the compounds described herein, including compounds that inhibit binding between MUC1 and an IKK, are also generally useful as therapies for the treatment of an allogeneic immune response (e.g., a response to a foreign cell or tissue (e.g., organ transplant rejection)) in a patient such as graft-versus-host disease. A compound described herein can be administered to subjects (e.g., transplant patients) alone or in conjunction with other drugs, radiotherapy, or hormonal therapies.

When the treatment methods described herein are applied to subjects with cancer, an inflammatory disorder (e.g., an autoimmune disease or an allogenic immune response), prior to administration of a compound, the cancer cells or immune cells (e.g., T-cells, B cells, or antigen presenting cells (APCs) such as dendritic cells, macrophages, or monocytes) involved in the response can optionally be tested for MUC1 expression (MUC1 protein or MUC1 mRNA expression) by methods known in the art. In this way, subjects can be identified as having a MUC1-expressing cancer. Such methods can be performed in vitro on cancer cells obtained from a subject. Alternatively, in vivo imaging techniques using, for example, radiolabeled antibodies specific for MUC1 can be performed. In addition, body fluids (e.g., blood or urine) from subjects with cancer can be tested for elevated levels of MUC1 protein or MUC1 protein fragments (see, for example, Treon et al. (2000) Blood 96(9):3147-3153).

In Vivo Approaches. The disclosure features a method of treating a subject having, suspected of having, or is at risk of developing, a cancer, which includes the steps of: optionally identifying a subject as having, suspected of having, or at risk of developing, a cancer comprising one or more cancer cells expressing MUC1; and delivering to the subject a composition comprising a compound that inhibits the interaction between MUC1 and an IKK.

The disclosure features a method of treating a subject having, suspected of or is at risk of developing, an inflammatory condition, which includes the steps of identifying a subject as having, or at risk of developing, an inflammatory condition (such as an autoimmune disease), where the subject has a site of inflammation and the site of inflammation contains immune cells, one or more of which express MUC1, and delivering to the subject a compound that inhibits the interaction between MUC1 and an IKK.

The disclosure also provides a method of treating a subject having, or at risk of developing, an allogeneic immune response, including the steps of: optionally identifying a subject as having, or at risk of developing, an allogenic immune response, where the subject has a site of inflammation, and the site of inflammation comprises immune cells, one or more of which express MUC1, and delivering to the subject a compound that inhibits the binding of MUC1 to an IKK.

In one in vivo approach, a compound that inhibits binding of MUC1 to an IKK is administered to a subject (e.g., a human subject (e.g., a human patient)). Generally, the compound will be suspended in a pharmaceutically-acceptable carrier (e.g., physiological saline) and administered orally or injected intravenously, subcutaneously, intramuscularly, intrathecally, intraperitoneally, intrarectally, intravaginally, intranasally, intragastrically, intratracheally, or intrapulmonarily. They can also be delivered directly to tumor cells (or immune cells), e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479, the disclosure of which is incorporated herein by reference in its entirety]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells [see U.S. Pat. Nos. 5,565,334 and 5,874,415, the disclosures of which are incorporated herein by reference in their entirety]. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

Inflammation and certain viral infections (e.g., infection of a cell with Herpes viruses, Papillomaviruses, or Hepatitis viruses) can induce transformation of a non-cancerous cell to a cell featuring characteristics of a cancer cell. In these instances, where cells express MUC1, inhibition of the interaction between MUC1 and an IKK can be useful in preventing malignant transformation of an inflamed cell, a virally-infected cell, or a cell that is malignantly transformed (or is made more susceptible to transformation) by soluble factors produced by inflammatory or inflamed cells (e.g., T lymphocytes, macrophages, or monocytes) or virally infected cells.

Elevated MUC1 expression is observed in chronically inflamed tissues such as human colonic epithelium in inflammatory bowel disease (see, e.g., Beatty et al. (2007) J. Immunol. 179: 735-739). In rodent models of inflammatory bowel disease, elevated MUC1 expression was shown to promote the development of inflammatory bowel disease and the progression of the disease to colon cancer (i.e., the transformation of inflamed colon cells to colon cancer cells). Thus, the disclosure features a method for inhibiting inflammation-induced transformation of a cell. The method includes the steps of: identifying a subject as having, suspected of having, or at risk of developing an inflammatory disorder mediated by one or more immune cells expressing MUC1 and/or an IKK; and delivering to the subject a compound that inhibits the interaction between MUC1 and an IKK.

The disclosure also provides methods for inhibiting viral-induced transformation of cell, which includes the steps of: optionally identifying a subject as having one or more cells infected with a virus capable of transforming the one or more cells, where the one or more cells also express MUC1, and delivering to the subject a compound that inhibits the interaction between MUC1 and an IKK. The transforming virus can be, e.g., any of those described above.

Compounds useful in the method include any compound identified by any method described herein or any compound with appropriate inhibitory activity, and are described above. The compounds useful in the method can be administered to a subject (e.g., a human subject (e.g., a human patient)), by any of the methods described above.

Additional methods are detailed below under "Pharmaceutical Compositions and Methods of Treatment."

Ex Vivo Approaches. An ex vivo strategy can involve transfecting or transducing cells obtained from the subject with a polynucleotide encoding a polypeptide that inhibit binding of MUC1 to an IKK. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells or immune cells, preferably obtained from the subject (autologous) but potentially from an subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the patient, where they secrete the polypeptide.

The ex vivo methods include the steps of harvesting cells from a subject, culturing the cells, transducing them with an expression vector, and maintaining the cells under conditions suitable for expression of the polypeptide that inhibits binding of MUC1 to an IKK. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the patient.

Methods for Inhibiting an IKK

Any of the compounds described herein, those identified by the methods, or any other compound having the appropriate inhibitory activity, can be used to inhibit an IKK (e.g., IKKα, IKKβ, or IKKγ). As used herein, inhibition of an IKK is understood to be inhibition of protein or mRNA expression of an IKK; inhibition of proper subcellular localization of an IKK (e.g., mislocalization from the IKK complex); inhibition of IKK kinase activity (methods for which are described below in detail); or inhibition of IKK protein or IKK mRNA stability.

As described herein, the method of inhibiting an IKK can involve steps of: identifying a cell as expressing MUC1, and culturing the cell with a compound that inhibits the activity of an IKK. MUC1 expression is understood to include, but not limited to, MUC1 mRNA or MUC1 protein expression. Suitable methods of detecting the expression of MUC1 protein or MUC1 mRNA are well known to those of skill in the art, and are described herein. These methods can include, for example, SDS-polyacrylamide gel electrophoresis/western blotting techniques using antibodies specific for MUC1 (for detection of protein), or RT-PCR or northern blotting techniques for detection of mRNA expression. The cell can be any cell that expresses MUC1, including cells that express an endogenous MUC1 or a cell that expresses a recombinant or exogenous MUC1 mRNA or polypeptide. The cell can also be a prokaryotic cell (e.g., a bacterial cell) or eukaryotic (e.g., an insect cell, a plant cell, a mammalian cell (e.g., a mouse or human cell)).

In one embodiment, inhibition of the activity of an IKK (e.g., the kinase activity of an IKK) can be detected using both cell-based and cell-free assays. In an aspect of the disclosure where the kinase assay is a cell-free assay, the method for determining IKK inhibition can involve the following steps:

contacting, in the presence of a test compound, a composition containing an IKK protein and a substrate (e.g., IκBα);

measuring phosphorylation of the IKK substrate;

wherein decreased phosphorylation of the IKK substrate in the presence of a compound as compared to phosphorylation of the IKK substrate that occurs in the absence of the compound indicates that the compound inhibits phosphorylation of an IKK substrate by the IKK protein (i.e., inhibits an IKK). The substrate can include physiological substrates for an IKK (e.g., IκBα), or can include a host of generic substrates commonly used by those of ordinary skill in the art for kinase assays. Suitable generic substrates for kinase assays can include, for example, MBP, casein, polyserine, polythreonine, polytyrosine, or BSA.

Assays by which inhibition of the kinase activity of an IKK (i.e., the ability to phosphorylate an IKK substrate) can be determined generally involve the addition of a kinase enzyme (an IKK or catalytically active portion thereof) to a substrate (e.g., IκBα or suitable phosphorylated fragment thereof, or an IKK protein itself (autophosphorylation)) in the presence of ATP, and magnesium (e.g., MgCl, MgOAc) or manganese, in a pH-buffered, suitable aqueous medium (e.g., Tris-buffered saline, HEPES), at physiologic temperature (e.g., 37° C.) for a suitable amount of time (e.g., 30 minutes, 60 minutes, 120 minutes). Kinase reaction conditions are well known to those of ordinary skill in the art, as well as general reaction optimization methodologies. An IKK kinase or catalytically active portion thereof can be purified, recombinant enzyme (e.g., recombinantly expressed in a bacterial cell, a yeast cell, an insect cell, or a mammalian cell) or can be isolated from a natural host that naturally expresses an IKK (e.g., a eukaryote, a mammal, a human).

Determining the inhibition of IKK kinase activity by a compound, can be directly measured by adding to a kinase reaction, a source of ATP comprising a detectably-labeled gamma-phosphate moiety. The detectable label can be, for example, a radioisotope label (e.g., $^{33}$P or $^{32}$P). The effectiveness of a given test compound to inhibit IKK kinase activity towards an IKK substrate can thus be measured by detecting the amount of labeled gamma-phosphate incorporation into the substrate, in the presence of absence of the candidate compound. Determining the amount of labeled phosphate incorporated into a substrate can be accomplished through the use of instrumentation that detects or quantitates a signal produced by the detectable label (e.g., radioisotope decay) such as a phosphorimaging machine or appropriate commercially available autoradiographic film.

In a related embodiment, inhibition of the kinase activity of an IKK towards an IKK substrate can be determined by analyzing the rate of the physical passage of a substrate through a stationary phase matrix (e.g., High Performance Liquid Chromatography (HPLC) or Thin Layer Chromatography (TLC) methodology). Following the reaction, samples can be resuspended in an appropriate solvent (or liquid phase) and actively or passively passaged over a stationary phase matrix, which can retard (i.e., increase the retention time of) a modified substrate on the basis of physical properties (e.g., size, hydrophobicity or charge). Phosphorylation of the IKK substrate by IKK can be determined by measuring the retention time between the passage of the phosphorylated compared to non-phosphorylated substrate over the stationary phase matrix. For more details about HPLC methodology, see, for example, Nageswara-Rao et al. J. Pharm. Biomed. Anal. 2003 Oct. 15; 33(3):335-77). Alternatively, following the reaction step of the procedure, the mixture can be resuspended in Laemmli buffer and subjected to polyacrylamide gel electrophoresis (PAGE). PAGE-resolved proteins, separated by size can then be transferred to a filter membrane (e.g., nitrocellulose) and subjected to western blot techniques using antibodies specific to an IKK substrate protein (e.g., anti-phospho-IκBα, see Examples below). The extent of phosphorylation of an IKK substrate, in the presence of absence of the candidate compound, can be detected by comparing the relative position in the gel of the phosphorylated species of substrate with the non-phosphorylated species of substrate.

In another embodiment, inhibition of the kinase activity of an IKK towards a substrate can be determined by immunoassay. The above IKK kinase reaction is performed, followed by addition of a detection antibody that specifically recognizes a phosphorylated residue in a given IKK substrate (e.g, anti-phospho-IκBα antibodies) or on a specific amino acid side chain (e.g., anti-phosphoserine or anti-phosphothreonine antibodies). Extent of phosphorylation of a given IKK substrate by an IKK in the presence of a test compound as compared to the absence of a compound can be determined by comparing the amount of antibody bound to each substrate species.

For the purposes of detection, the immunoassay method above can be performed with an antibody that bears a detection moiety, (e.g., a fluorescent agent such a europium, terbium, green-fluorescent protein, fluorescent dyes). Within this embodiment, the IKK substrate can be conjugated to a solid-phase matrix directly (e.g., a multiwell assay plate, nitrocellulose, or agarose, sepharose, or magnetic beads) or it can be conjugated to one member of a specific binding pair (e.g., conjugated to biotin or streptavidin). Such conjugation allows the IKK substrate to be purified away from additional reaction components prior to contact with the detection antibody. One embodiment of this method of detection can be, for example, the commercially available DELFIA® system from Perkin Elmer®.

Alternatively, the immunoassay method may involve the use of two detection moieties. Such an embodiment takes advantage of fluorescence resonance energy transfer (FRET), which is the radiationless transfer of energy from donor molecule to acceptor molecule. The donor molecule is a dye or chromophore that initially absorbs the energy and the acceptor is the chromophore to which the energy is subsequently transferred (called a donor/acceptor pair). This resonance interaction occurs over greater than inter-atomic distances, without conversion to thermal energy and without any molecular collision. FRET relies on the distance-dependent transfer of energy from a donor molecule to an acceptor molecule, and due to its sensitivity to distance, is extremely useful in investigating protein-protein interactions and also enzymatic reactions.

In one instance, the IKK substrate molecule (e.g., IκBα or generic peptide substrate) may be conjugated to the energy acceptor molecule, and the anti-phospho-serine/threonine antibody may be conjugated to the energy donor molecule. In another instance, the IKK substrate may be conjugated to the energy donor molecule and the anti-phospho-serine/threonine antibody may be conjugated to the energy acceptor molecule. The IKK substrate may be bound directly to either FRET energy acceptor or donor or be conjugated first to a first member of a specific binding pair (e.g., biotin) with the FRET energy acceptor or donor conjugated to a second member of a specific binding pair. Inhibition of IKK kinase activity towards a IKK substrate by a test compound is determined by measuring the amount of FRET in following a reaction in the presence or absence of a test compound. In one embodiment of the method, the method is the LANCE® method commercially available from Perkin Elmer®.

In another embodiment, the inhibition of an IKK can be determined using a cell-based assay in which IKK biological activity of IKK kinase on its physiological substrates (e.g., IκBα) can be evaluated in the context of a test agent. This screening assay method can, for example, comprise:

identifying a cell as expressing MUC1; and
contacting the cell with a compound that inhibits an IKK.

Inhibition of the in vivo, biological activity (e.g., kinase activity) of an IKK can be measured by monitoring the phosphorylation state of endogenous, natural IKK substrates (e.g., IκBα). The phosphorylation state of these substrates can be measured in intact cells using antibody-mediated immunofluorescence or immunohistochemical techniques. The phosphorylation state of endogenous substrates can alternatively be measured by solubilizing the cells in Laemmli buffer and subjecting the solubilized extracts to SDS-PAGE, followed by western blotting with antibodies specific for phosphorylated residues in the IKK substrate proteins (e.g., an antibody that specifically recognizes a phosphorylated amino acid residue in IκBα). Alternatively, antibodies that recognized non-phosphorylated IKK substrates may be amenable for this assay as they can be used to detect changes in protein mobility consistent with protein modification (e.g., phosphorylation).

Compounds useful for inhibiting the activity of a IKK are known in the art and include, for example, MX781, PS1145, and anilinopyrimidine derivatives (U.S. Patent Publication No. 20060030576; Bayon et al. (2003) Mol. Cell. Biol. 23(3):

1061-74; Cilloni et al. (2006) Leukemia 20:61-67; and Yemelyanov et al. Oncogene 25(3):387-98; herein incorporated by reference in their entirety).

Inhibition of an IKK also includes inhibition of the expression of an IKK (e.g., inhibition of the expression of an IKK mRNA or protein). Compounds useful for inhibiting the expression of an IKK include an antisense oligonucleotide that hybridizes to an IKK mRNA transcript, or an IKK specific small interference RNA (siRNA). Antisense oligonucleotides hybridize to IKK transcripts and have the effect in the cell of inhibiting expression of IKK.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with a antisense compound is chosen. Thus, for example, for modulation of polyadenylation a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, a combination of the two, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

Also useful in the method of inhibiting the expression of an IKK are double-stranded small interference RNA (siRNA) homologous to IKK DNA, which can be used to reduce expression of IKK in a cell. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026. The disclosures of all these articles are incorporated herein by reference in their entirety.

The sense and anti-sense RNA strands of siRNA can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. Some of the nucleotides (e.g., the terminal (either terminus) one, two, three, or four nucleotides) can also be deoxyribonucleotides. The sense or anti-sense strand can also be produced biologically using an expression vector into which a target NF-κB sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to cells.

In addition to the example compounds described above, any of the compounds identified through any of the methods described herein, or any compound with appropriate inhibitory activity can be used as compounds to inhibit the activity of an IKK on endogenous physiological substrates (e.g., IκBα). Such compounds also include one or more of the MUC1 fragments including: (i) a fragment of the cytoplasmic domain (CD) of human MUC1 can containing or consisting of amino acids 1-45 (SEQ ID NO:3) of the human MUC1 CD (SEQ ID NO:2) (e.g., a polypeptide containing or consisting of amino acids 1-45 (SEQ ID NO:3) of MUC1-CD), herein referred to as MUC1-CD(1-45); (ii) a fragment of the CD of human MUC1 containing or consisting of amino acids 46-72 (SEQ ID NO:4) of the human MUC1 CD (SEQ ID NO:2) (e.g., a polypeptide containing or consisting of amino acids 46-72 (SEQ ID NO:4) of MUC1-CD); herein referred to as MUC1-CD (46-72); or (iii) a fragment of the CD of human MUC1 containing or consisting of amino acids 50-59 (SEQ ID NO: 13) of the human MUC1 CD (SEQ ID NO:2) (e.g., a polypeptide containing or consisting of amino acids 50-59 (SEQ ID NO:13) MUC11-CD(SEQ ID NO:2), herein referred to as MUC1-CDSRM (serine-rich motif)). Other useful inhibitory compounds include fragments of an IKK including: (i) a fragment of an IKK that contains or consists of all or part of amino acids 1-458 (SEQ ID NO:7) of human IKKβ (SEQ ID NO:6), herein referred to as IKKβ (1-458); or (ii) a fragment of an IKK including all or part of amino acids 197-419 (SEQ ID NO:9) of human IKKγ (SEQ ID NO:8), herein referred to as IKKγ (197-419). Methods of introducing exogenous polypeptides or substrates suitable for phosphorylation by an IKK into cells are known to one of ordinary skill in the art (e.g., attachment of antennaepedia or RGD-peptide sequences to the IKK substrate polypeptides (e.g., a IκBα polypeptides)) and described above.

In vivo Approaches. The disclosure also provides an in vivo method for inhibiting an IKK, which includes the steps of: optionally identifying a subject as having, suspected of having, or at risk of developing, a cancer containing one or more cells expressing MUC1, and delivering to the subject a compound that inhibits an IKK. Also featured is an in vivo method for inhibiting an IKK, which includes the steps of: optionally identifying a subject as having, suspected of having, or at risk of developing, an inflammatory disorder (such as an autoimmune disease) mediated by one or more immune cells expressing MUC1, and delivering to the subject a compound that inhibits an IKK. Compounds (for example, compounds that inhibit IKK kinase activity or IKK expression, see above) useful in the method include any compound identified by a method described herein or any compound with appropriate inhibitory activity. The compounds useful in the method can be administered to a subject (e.g., a human subject (e.g., a human patient)), by any of the methods described above. Additional methods are detailed below under "Pharmaceutical Compositions and Methods of Treatment."

Ex vivo Approaches. An ex vivo strategy can involve transfecting or transducing cells obtained from the subject (or from another subject) with a polynucleotide encoding a polypeptide that inhibits an IKK (e.g., IKKα, IKKβ, or IKKγ). The transfected or transduced cells are then administered to the subject. The cells can be any of a wide range of types including, without limitation, any of the cells described above. The ex vivo methods include the steps of harvesting cells from a subject, culturing the cells, transducing them with an expression vector, and maintaining the cells under conditions suitable for expression of the polypeptide that inhibits an IKK (e.g., IKKα, IKKβ, or IKKγ). These methods are known in the art of molecular biology and suitable methods are described above.

Methods for Inhibiting IκBα Phosphorylation

Any of the compounds described herein, those identified by the methods, or any of compound having the appropriate inhibitory activity, can be used to inhibit the phosphorylation of IκBα. Inhibition of the phosphorylation of IκBα is understood to include inhibition of any protein kinase capable of phosphorylating IκBα in vitro or in vivo. Examples of such kinases include, for example, IKKs (IKKα, IKKβ, IKKγ, see above), and Casein Kinase II (Barroga et al. (1995) Proc. Natl. Acad. Sci. USA 92:7637-7641).

As described herein, the method of inhibiting the phosphorylation of IκBα can involve steps of: identifying a subject as having, suspected of having, or at risk of developing, a cancer containing one or more cancer cells expressing MUC1, and delivering to the subject a compound that inhibits IκBα phosphorylation. MUC1 expression is understood to include, but not limited to, MUC1 mRNA or MUC1 protein expression and suitable methods of detecting the expression of MUC1 protein or MUC1 mRNA are provided above. The one or more cancer cells can be any cell that express MUC1, including a cell that expresses an endogenous MUC1 or a cell that expresses a recombinant or exogenous MUC1 mRNA or polypeptide. Though the subject can be any mammal (e.g., monkeys, baboons, or chimpanzees, horses, cattle, pigs, sheep, goats, dogs, cats, rabbits, guinea pigs, gerbils, hamsters, rats, and mice), preferably the subject is a human subject (e.g., a human patient).

Suitable compounds for use in the method of inhibiting IκBα phosphorylation include, but are not limited to, those described above under "Inhibition of an IKK." In addition, compounds such as staurosporin and 5,6-dichloro-1-β-D-ribofuranosylbenzimidazole are also useful in the method (Critchfield et al. (1997) Proc. Natl. Acad. Sci. USA 94:6110-6115). Suitable methods of delivery (e.g., administration) of the compounds are described below.

Methods (in vitro, in situ, and in vivo) of detecting inhibition of the phosphorylation of IκBα are well known to those of skill in the art and include, for example, western blotting or immunohistochemistry using antibodies specific for phosphorylated IκBα. Such methods are described above under "Inhibition of an IKK." Using these methods, a reduction in the amount of signal produced from a phosphorylated IκBα detection moiety (e.g., a detectably-labeled anti-phospho-IκBα antibody), as compared to the amount of signal produced in the absence indicates that a compound has inhibited the phosphorylation of IκBα.

In vivo Approaches. The disclosure also provides an in vivo method of inhibiting IκBα phosphorylation, which includes the steps of identifying a subject as having, suspected of having, or at risk of developing, a cancer containing one or more cancer cells expressing MUC1, and delivering to the subject a compound that inhibits the phosphorylation of IκBα. Also featured is an in vivo method of inhibiting IκBα phosphorylation, which includes the steps of identifying a subject as having, suspected of having, or at risk of developing, an inflammatory disorder mediated by one or more immune cells expressing MUC1, and delivering to the subject a compound that inhibits the phosphorylation of IκBα. Compounds (for example, compounds that inhibit IKK kinase activity, see above) useful in the method include any compound identified by any of the methods described herein or any compound with appropriate inhibitory activity. The compounds useful in the method can be administered to a subject (e.g., a human subject (e.g., a human patient)), by any of the methods described above. Additional methods are detailed below under "Pharmaceutical Compositions and Methods of Treatment."

Ex vivo Approaches. An ex vivo strategy can involve transfecting or transducing cells obtained from the subject (or from another subject) with a polynucleotide encoding a polypeptide that inhibits the phosphorylation of IκBα. The transfected or transduced cells are then administered to the subject. The cells can be any of a wide range of types including, without limitation, any of the cells described above. The ex vivo methods include the steps of harvesting cells from a subject, culturing the cells, transducing them with an expression vector, and maintaining the cells under conditions suitable for expression of the polypeptide that inhibits the phosphorylation of IκBα. These methods are known in the art of molecular biology and suitable methods are described above.

Methods for Inhibiting NF-κB

The present invention also features a method of inhibiting NF-κB. The method described herein for inhibiting NF-κB can involve:

identifying a cell as expressing MUC1; and culturing the cell with a compound that inhibits NF-κB.

Methods of identifying a cell as expressing MUC1 are described above in "Inhibition of an IKK." Also described above are cells embraced by the method of inhibition. "Inhibiting NF-κB" is any method of inhibiting the expression or physiologic action or function of NF-κB in a cell or in a cell-free system. For example, inhibiting can be inhibition of the expression of NF-κB in a cell or in an in vitro system. This can include inhibition of the transcription of the gene (i.e., the production of mRNA), or changes in the expression of the protein from the mRNA (e.g., the translation of the protein). "Inhibiting NF-κB" can also occur by affecting the stability of the NF-κB mRNA or protein. As used herein, an "NF-κB-inhibitor" is a compound that inhibits NF-κB by any method described herein.

Compounds or agents useful for inhibiting the stability of NF-κB mRNA include, for example, specific antisense or siRNA agents that target NF-κB mRNA, or agents that increase the degradation of the protein (e.g., a nucleic acid encoding IκBα, introduced and expressed in a cell) as described above for inhibiting an IKK.

Methods of detecting a change in expression (e.g., a reduction in the expression) of an NF-κB mRNA or NF-κB protein are well known to those of skill in the art. Suitable methods for detection of mRNAs include, for example, RT-PCR and northern blotting technologies. Methods suitable for the detection of changes in protein concentration can include, western blotting or enzyme-linked immunosorbent assay (ELISA) techniques using antibodies that are specific for NF-κB protein.

Inhibiting NF-κB can also include inhibiting NF-κB-mediated gene trans-activation activity (e.g., the transcription factor function of NF-κB). Methods of assessing NF-κB transactivation activity are also well known to those of skill in the art. Cell-based methods can involve monitoring the expression of NF-κB target genes (for example, Bcl-2, Bcl-$x_L$, c-IAP1, c-IAP2, MnSOD2, VEGF, androgen receptor, c-myc, IκBα, and p53). Assessing the inhibition of target gene expression, at the level of mRNA or protein, can be done using in situ or in vitro techniques, including, but not limited to, methods described above (e.g., immunofluorescence and western blot (for measuring protein) or RT-PCR and northern blotting techniques (for RNA)). Alternatively, detecting an inhibition of NF-κB activity can be done using an NF-κB driven reporter system. By this method, nucleic acid vectors are designed which encode a coding sequence for a reporter gene (e.g., luciferase, chloramphenicol acetyltransferase (CAT), or green fluorescent protein(GFP)) operably linked to an NF-κB responsive enhancer element (see, for example, the Example sections below; Zamora et al. (2004) J. Biol. Chem. 279(37):38415-38423; Jacque et al. (2005) Proc. Natl. Acad. Sci. USA 102(41):14635-14640). The vector can be introduced into a cell by any suitable transfection method. Ideally, a change in the expression of a reporter gene in the presence and absence of a test compound would be used to determine the effect of a compound on NF-κB activity. In related aspects, a stimulus, such as TNFα, could be co-administered to the cells to stimulate the activity of NF-κB, and activation of NF-κB would correspond to an increase in the amount of expression of the reporter gene from the reporter vector (Jacque et al. (2005) Proc. Natl. Acad. Sci. USA 102(41): 14635-14640). Conversely, inhibition of NF-κB-driven reporter expression (i.e., inhibition of NF-κB) would correspond to a reduction in the expression of a reporter gene from the reporter vector, and indicate that the test compound inhibits NF-κB activity. Methods of detecting an inhibition of NF-κB-driven reporter gene expression can also include RT-PCR or western blotting as described above. Preferably, the reporter gene encodes a polypeptide which is capable of giving a easily detectable signal, for example, fluorescence from a GFP moiety, or a detectable enzymatic activity present in CAT.

Detection can include lysis of the cells expressing the reporter gene, or in situ detection.

Compounds useful in inhibiting NF-κB activity are well known in the art and include, for example, 2-cyclopenten-1-one and its derivatives, imidazoline compounds, basiliolide compounds, bortezomib, and PS-1145 (see, for example, U.S. Patent Publication Nos. 20020137800 and 20030232998; Navarrete et al. (2006) J. Pharmacol. Exp. Ther. July 13; and Vodanovic-Jankovic et al. (2006) Blood 107(2):827-34; all included herein by reference in their entirety).

Inhibiting NF-κB can also include inhibition of physiologic localization of NF-κB (i.e., inhibition of nuclear translocation of NF-κB). Methods of detecting the subcellular localization of NF-κB are well known to those of ordinary skill in the art (see, for example, the Example section below), and often include (but do not necessarily require) the administration of a cytokine (e.g., TNFα) or other NF-κB stimulating agent (e.g., LPS) to activate NF-κB and promote its nuclear localization. A test compound can thus be co-administered with the NF-κB stimulator to assess the effect of the test compound on the activation of NF-κB. Thus, more nuclear localization of NF-κB in the absence of a test compound as compared to the nuclear localization in the presence of the test compound indicates that the test compound inhibits the nuclear localization of NF-κB. Nuclear localization of NF-κB can be detected, for example, by cell fractionation (i.e., detecting the amount of NF-κB in a cytosolic versus a nuclear extract prepared from the same source of cells) and immunoblotting or ELISA (see, Examples below). Alternatively, localization of NF-κB can be done in situ, generally by methods including, but not limited to: (i) fixing the cells; (ii) treatment of the fixed cells with detectably-labeled antibodies specific to NF-κB; and (iii) detecting the signal produced by the detectable label using any of a number of methods known to those in the art, including fluorescence-assisted cell sorting (FACS) and confocal microscopy (see, Lin et al. (1995) J. Biol. Chem. 270(24):14255-14258; Tsukahara et al. (1999) J. Virol. 73(10):7981-7987). The detectable label can be conjugated to the first antibody (the primary antibody which specifically recognizes NF-κB) or on a secondary antibody which is capable of binding to the first antibody. Alternatively, the first antibody can be conjugated to the first member of a binding pair (i.e., strepavidin or biotin) and the second member of the binding pair can be linked to the detectable moiety. The detectable moiety can include radiolabels (e.g., $^{125}$I, $^{35}$S, $^{33}$P, or $^{32}$P), fluorescent labels (e.g., texas red, fluorescein), a luminescent moiety (e.g., a lanthanide), or a one or more members of a FRET pair.

In vivo Approaches. The disclosure also provides an in vivo method of inhibiting NF-κB, which includes the steps of identifying a subject as having, suspected of having, or at risk of developing, a cancer containing one or more cancer cells expressing MUC1, and delivering to the subject a compound that inhibits NF-κB. Compounds (for example, compounds that inhibit NF-κB, see above) useful in the method include any compound identified by any of the methods described herein or any compound with appropriate inhibitory activity. The compounds useful in the method can be administered to a subject (e.g., a human subject (e.g., a human patient)), by any of the methods described above. Additional methods are detailed below under "Pharmaceutical Compositions and Methods of Treatment."

Ex vivo Approaches. An ex vivo strategy can involve transfecting or transducing cells obtained from the subject (or from another subject) with a polynucleotide encoding a polypeptide that inhibits NF-κB. The transfected or transduced cells are then administered to the subject. The cells can be any of a wide range of types including, without limitation, any of the cells described above. The ex vivo methods include the steps of harvesting cells from a subject, culturing the cells, transducing them with an expression vector, and maintaining the cells under conditions suitable for expression of the polypeptide that inhibits NF-κB. These methods are known in the art of molecular biology and suitable methods are described above.

Methods of Designing and Producing Inhibitory Compounds

The disclosure also relates to using MUC1 test agents and/or IKK test agents to predict or design compounds that can interact with MUC1 and/or an IKK and potentially thereby inhibit the ability of MUC1 to promote the NF-κB signaling pathway. One of skill in the art would know how to use standard molecular modeling or other techniques to identify small molecules that would bind to "appropriate sites" on MUC1 and/or an IKK. One such example is provided in Broughton (1997) Curr. Opin. Chem. Biol. 1, 392-398. Generally, an "appropriate site" on a MUC1 or an IKK is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction in a conformational change in the molecule) in inhibition of the binding of the molecule to another molecule By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to the region of MUC1 that interacts with an IKK (i.e., the cytoplasmic domain of MUC1) or the region of an IKK that binds to MUC1 (i.e., the 197-419 amino acid region of IKKγ) typically are also computer-based, and involve the use of a computer having a program capable of generating an atomic model. Computer programs that use X-ray crystallography data are particularly useful for designing such compounds. Programs such as RasMol, for example, can be used to generate a three dimensional model of, e.g., the region of MUC1 that interacts with an IKK or the region of an IKK that binds to MUC1 and/or determine the structures involved in MUC1-IKK binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The methods can also be implemented by means of a computer-readable storage medium, configured with a computer program, where the storage medium so configured causes a computer to operate in a specific and predefined manner to perform the functions described herein.

For example, the computer-requiring steps in a method of designing an immunogenic compound can involve:

(a) inputting into an input device, e.g., through a keyboard, a diskette, or a tape, data (e.g. atomic coordinates) that define the three-dimensional (3-D) structure of a first molecule (e.g., MUC1 or a part of MUC1) that binds to a second molecule (e.g., an IKK or a part thereof) or a molecular complex (e.g., MUC1, or a part thereof, bound to an IKK, or a part thereof, or MUC1 bound to a macromolecular IKK complex), e.g., a region of MUC1 that interacts with an IKK (i.e., the cytoplasmic domain of MUC1), the region of an IKK that binds to MUC1 (i.e., the carboxy-terminal portion of IKKγ or the amino-terminal portion of IKKβ), or all or a part (e.g., the cytoplasmic domain) of MUC1 bound to all or a part of an IKK; and (b) determining, using a processor, the 3-D structure (e.g., an atomic model) of: (i) the site on the first molecule involved in binding to the second molecule; or (ii) one or more sites on the molecular components of molecular complex of interaction between molecular components of the molecular complex.

From the information obtained in this way, one skilled in the art will be able to design and make inhibitory compounds (e.g., peptides, non-peptide small molecules, aptamers (e.g., nucleic acid aptamers) with the appropriate 3-D structure (see "Methods of Making Inhibitory Compounds and Proteins" below).

Moreover, if computer-usable 3-D data (e.g., x-ray crystallographic or nuclear magnetic resonance (NMR) data) for a candidate compound are available, the following computer-based steps can be performed in conjunction with computer-based steps (a) and (b) described above:

(c) inputting into an input device, e.g., through a keyboard, a diskette, or a tape, data (e.g. atomic coordinates) that define the three-dimensional (3-D) structure of a candidate compound;

(d) determining, using a processor, the 3-D structure (e.g., an atomic model) of the candidate compound;

(e) determining, using the processor, whether the candidate compound binds to the site on the first molecule or the one or more sites on the molecular components of the molecular complex; and (f) identifying the candidate compound as compound that inhibits the interaction between the first and second molecule or the between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1, the cytoplasmic domain of MUC1, an IKK, or a MUC1-interacting fragment of an IKK) stored in a data storage system.

Compounds useful in any of the methods described herein also may be interactively designed from structural information of the compounds described herein using other structure-based design/modeling techniques (see, e.g., Jackson (1997) *Seminars in Oncology* 24:L164-172; and Jones et al. (1996) *J. Med. Chem.* 39:904-917). Compounds and polypeptides also can be identified by, for example, identifying candidate compounds by computer modeling as fitting spatially and preferentially (i.e., with high affinity) into the appropriate acceptor sites on MUC1 or an IKK.

Candidate compounds identified as described above can then be tested in standard cellular or cell-free binding or binding inhibition assays familiar to those skilled in the art. Exemplary assays are described herein.

A candidate compound whose presence requires at least 2-fold (e.g., 4-fold, 6-fold, 10-fold, 100-fold, 1000-fold, 10,000 fold, or 100,000-fold) more of a given MUC1 test agent to achieve a defined arbitrary level of binding to a fixed amount of an IKK test agent than is achieved in the absence of the compound can be useful for inhibiting the interaction between MUC1 and the relevant IKK, and thus can be useful as a cancer therapeutic or prophylactic agent. Alternatively, a candidate compound whose presence requires at least 2-fold (e.g., 2-fold, 4-fold, 6-fold, 10-fold, 100-fold, 1000-fold, 10,000 fold, or 100,000-fold) more of a given IKK test agent to achieve a defined arbitrary level of binding to a fixed amount of a MUC1 test agent than is achieved in the absence of the compound can be useful for inhibiting the interaction between MUC1 and the relevant IKK, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this disclosure [e.g., Cohen et al. (1990) J. Med. Chem. 33: 883-894; Navia et al (1992) Current Opinions in Structural Biology, 2, pp. 202-210, the disclosures of which are incorporated herein by reference in its entirety]. All these methods produce data that are amenable to computer analysis. Other spectroscopic methods that can also be useful in the methods described herein, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991) Advances in Protein Chemistry, 41:1-36]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M Hepes, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) J. Biol. Chem., 251:6300-6306], an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to $-220°$ C. to $-50°$ C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer.

Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. application Ser. No. 10/486,278, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) BioTechniques, 29:1278-1294].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenbom et al. (1990) Anal. Chem. 62(1):2-15; and Wider (2000), supra., the disclosures of all of which are incorporated herein by reference in their entirety Any available method can be used to construct a 3-D model of a region of MUC1 and/or an IKK of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.
Compounds Compounds identified in any of the methods described herein, or any compound with appropriate activity useful in any of the methods described herein can include various chemical classes, though typically small organic molecules having a molecular weight in the range of 50 to 2,500 daltons. These compounds can comprise functional groups necessary for structural interaction with proteins (e.g., hydrogen bonding), and typically include at least an amine, carbonyl, hydroxyl, or carboxyl group, and preferably at least two of the functional chemical groups. These compounds often comprise cyclical carbon or heterocyclic structures and/or aromatic or polyaromatic structures (e.g., purine core) substituted with one or more of the above functional groups.

In alternative embodiments, compounds can also include biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, and polynucleotide analogs.

Of particular interest as small molecule compounds are nucleic acid aptamers which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) [see, for example, Zhang et al. (2004) Arch. Immunol. Ther. Exp. 52:307-315, the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see Zhang et al. (2004) and Brody et al. [(2000) Reviews in Molecular Biotechnology 74:5-13, the disclosure of which is incorporated herein by reference in its entirety].

Compounds can be identified from a number of potential sources, including: chemical libraries, natural product libraries, and combinatorial libraries comprised of random peptides, oligonucleotides, or organic molecules. Chemical libraries consist of random chemical structures, some of which are analogs of known compounds or analogs or compounds that have been identified as "hits" or "leads" in other drug discovery screens, while others are derived from natural products, and still others arise from non-directed synthetic organic chemistry. Natural product libraries re collections of microorganisms, animals, plants, or marine organisms which are used to create mixtures for screening by: (1) fermentation and extraction of broths from soik, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Bioechnol. 8:701-707 (1997). Identification of test compounds through the use of the various libraries herein permits subsequent modification of the test compound "hit" or "lead" to optimize the capacity of the "hit" or "lead" to inhibit the interaction between MUC1 and an IKK.

The compounds identified above can be synthesized by any chemical or biological method. The compounds identified above can also be pure, or may be in a heterologous composition (e.g., a pharmaceutical composition), and can be prepared in an assay-, physiologic-, or pharmaceutically-acceptable diluent or carrier (see Pharmaceutical Compositions and Methods of Treatment below). This composition can also contain additional compounds or constituents which do not bind to or inhibit the interaction between MUC1 and an IKK, or inhibit NF-κB, IκBα phosphorylation, or an IKK in a cell that expresses MUC1.
Pharmaceutical Compositions and Methods of Treatment The present disclosure also provides for pharmaceutical compositions comprising a therapeutically effective amount of a compound, or a pharmaceutically acceptable salt thereof together with a pharmaceutically acceptable carrier, diluent, or excipient therefor. A compound that has been screened by a method described herein and determined, for example, to (a) inhibit the interaction between MUC1 and an IKK, (b) inhibit the phosphorylation of IκBα, (c) inhibit an IKK or NF-κB, or (d) inhibit the growth of a cancer cell (e.g., a colon cancer cell, a breast cancer cell, a prostate cancer cell, a lung cancer cell, a lymphoma), can be considered a candidate compound. A candidate compound that has been screened, e.g., in an in vivo model of cancer or inflammation and determined to have a desirable effect on the disorder, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients to form pharmaceutical compositions.

Any of the compounds described herein can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A compound can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

The dose administered to a subject, in the context of the methods described herein should be sufficient to affect a beneficial therapeutic response in the subject over time. The term "subject" refers to a member of the class Mammalia. Examples of mammals include, without limitation, humans, primates, chimpanzees, rodents, mice, rats, rabbits, horses, livestock, dogs, cats, sheep, and cows. In certain embodiments, the "subject" is a human.

The dose will be determined by the efficacy of the particular compound employed and the condition of the subject, as well as the body weight or surface area of the subject to be treated. The size of the dose also will be determined by the existence, nature, and extent of any adverse side effects that accompany the administration of a particular compound in a particular subject. In determining the effective amount of the compound to be administered in the treatment or prophylaxis of the disease being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject. Many different administration methods are known to those of skill in the art.

For administration, compounds can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

Toxicity and therapeutic efficacy of such compounds can be determined known pharmaceutical procedures in cell cultures or experimental animals (animal models of cancer, e.g., colon, breast, prostate, or lung cancer models, or animal models of autoimmune disease, e.g., arthritis or lupus erythematosus). For example, the efficacy or toxicity of a compound to, e.g., inhibit an interaction between MUC1 and an IKK in vivo, can be tested using a rodent model of inflammatory bowel disease as described in Beatty et al. (supra; the disclosure of which is incorporated by reference in its entirety). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For a compound used as described herein (e.g., for treating an infection or cancer in a subject), the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Compounds that inhibit the growth of a cell, (i.e., a mammalian cell, a human cancer cell) can be any of the compounds described herein.

As defined herein, a therapeutically effective amount of a compound (i.e., an effective dosage) includes milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the inhibition of the cell growth (i.e., inhibition of the growth of a cancer cell). When one or more of these small molecules is to be administered to an animal (e.g., a human) to treat an infection or a cancer, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated. One in the art will also appreciate that certain additional factors may influence the dosage and timing required to effectively treat a subject, including but not limited to the severity of the disease or disorder, previous treatments, and other diseases present. Moreover, treatment of a subject with a therapeutically effective amount of a protein, polypeptide, or antibody can include a single treatment or can include a series of treatments.

The pharmaceutical compositions can be included in a container, pack, or dispenser together with instructions for administration.

The following examples are intended to illustrate, not limit, the invention.

EXAMPLES

Example 1

Materials and Methods

Cell culture. Human HCT116 colon carcinoma cells, HeLa cervical carcinoma cells and MCF-7 breast cancer cells were grown in Dulbecco's modified Eagle's medium with 10% heat-inactivated fetal bovine serum, 100 units/ml penicillin, 100 mg/ml streptomycin and 2 mM L-glutamine. Human ZR-75-1 breast cancer cells were grown in RPMI1640 medium containing 10% heat-inactivated fetal bovine serum, antibiotics and L-glutamine. Human MCF-10A breast epithelial cells were grown in mammary epithelial cell growth media (MEGM; Cambrex Corp.).

Subcellular fractionation. Nuclear and cytosolic fractions were prepared as described in Kharbanda et al. (1996) Cancer Res. 56:3617-3621.

Immunoprecipitation and immunoblotting. Lysates from subconfluent cells were prepared as described in Ren et al. (2004) Cancer Cell 5:163-175. Soluble proteins were incubated with anti-IKKβ (Cell Signaling Technology) or anti-IKKγ (Santa Cruz Biotechnology) for 2 h at 4° C. Immune complexes and cell lysates were subjected to immunoblotting with anti-MUC1-C (Ab5; Neomarkers), anti-β-actin (Sigma), anti-NF-κB p65 (Santa Cruz Biotechnology), anti-lamin B (Calbiochem), anti-Bcl-$x_L$ (Santa Cruz Biotechnology), anti-phospho-IκBα (Cell Signaling Technology), anti-IκBα (Santa Cruz Biotechnology), anti-IKKβ (Cell Signaling Technology), anti-IKKγ (Santa Cruz Biotechnology) and anti-phospho-IKKβ (Cell Signaling Technology). The immune complexes were detected with horseradish peroxidase-conjugated secondary (anti-IgG) antibodies (Amersham Biosciences) and enhanced chemiluminescence (ECL; Amersham Biosciences). For immunodepletion studies, cell lysates were incubated with increasing amounts of anti-MUC1-C for 2 hours at 4° C. MUC1-C immunocomplexes were precipitated with protein G beads. The immune complexes and the immunodepleted supernatant were subjected to immunoblotting.

Luciferase assays. Cells were transfected with wild-type or mutant pNF-κB-Luc (Ashburner et al. (2001) Mol. Cell. Biol. 21:7065-7077) and SV-40-*Renilla*-Luc (Promega) in the presence of LipofectAMINE (Invitrogen, Carlsbad, Calif.). After 48 hour, cells were lysed in passive lysis buffer. Lysates were analyzed for firefly and *Renilla* luciferase activities using the dual luciferase assay kit (Promega).

Pulse-chase analysis. Cells were cultured in methionine-free medium containing 200 mCi/ml [$^{35}$S]-labeled methionine (Perkin-Elmer Life Sciences) for 1 hour, washed and then chased in the presence of complete medium. Lysates were prepared from the cells and IκBα was immunoprecipitated using anti-IκBα antibodies. Anti-IκBα immunoprecipitates were subjected to SDS-PAGE and autoradiography. Intensity of the signals was determined by densitometric scanning.

RT-PCR. Total cellular RNA was extracted with the High Pure RNA Isolation kit (Roche). IκBα-specific (5'-AGTCCT-GCACCACCCCGCACC-3' (SEQ ID NO: 11) and 3'-TCAT-AACGTCAGACGCTGGCCTC-5' (SEQ ID NO:12)) and β-actin-specific (Li et al. (2003) Cancer Biol. Ther. 2:187-193) primers were used for reverse transcription and amplification (SuperScript One-Step RT-PCR with Platinum Taq; Invitrogen). Amplified fragments were analyzed by electrophoresis in 2% agarose gels.

In vitro binding assays. Purified GST-MUC1-CD (glutathione s-transferase fused to the MUC1-CD polypeptide) was cleaved with thrombin to remove the GST moiety. GST, GST-IKKβ (DiDonato et al. (1997) Nature 388:548-554), GST-IKKβ (1-458), GST-IKKβ (458-756), GST-IKKγ (Prajapati et al. (2002) J. Biol. Chem. 277:24331-24339), GST-IKKγ (1-196) or GST-IKKγ (197-419) were then incubated with the MUC1-CD for 1 hour at 25° C. In other experiments, GST, GST-MUC1-CD, GST-MUC1-CD(1-45) or GST-MUC1-CD(46-72) were incubated with purified IKKβ or IKKγ. Adsorbates to glutathione-conjugated beads were analyzed by immunoblotting.

Protein gel filtration chromatography. HeLa/vector and HeLa/MUC1 cells were lysed in 50 mM Tris-HCl, pH 7.5, 150 mM NaCl, 1 mM sodium vanadate, 1 mM PMSF, 1 mM DTT, 10 mM sodium fluoride, 10 mCi/ml aprotinin and 10 mCi/ml leupeptin for 15 minutes at 4° C. The lysates were sedimented at 14,000×g for 15 minutes to remove the insoluble fraction. Soluble protein (500 mg) was injected into a Sephacryl S-200 HR column and separated by Fast Protein Liquid Chromatography (FPLC) using the lysis buffer. Thirty 4-ml fractions were collected and 40 ml aliquots were subjected to immunoblot analysis.

In vitro kinase assays. IKK complexes were immunoprecipitated with anti-IKKβ antibodies. The precipitates were incubated in 50 mM HEPES (pH 7.4), 10 mM $MgCl_2$, 10 mM $MnCl_2$, 2 mM dithiothreitol, 0.1 mM sodium vanadate, 10 mM ATP, 0.4 mCi/ml [$^{32}$P]ATP (NEN Life Science Products) and 0.1 mg/ml purified GST-IκBα (1-54) for 30 minutes at 30° C. The reaction products were analyzed by SDS-PAGE and autoradiography.

Example 2

MUC1 Induces Activation of NF-κB p65

Figure 2:
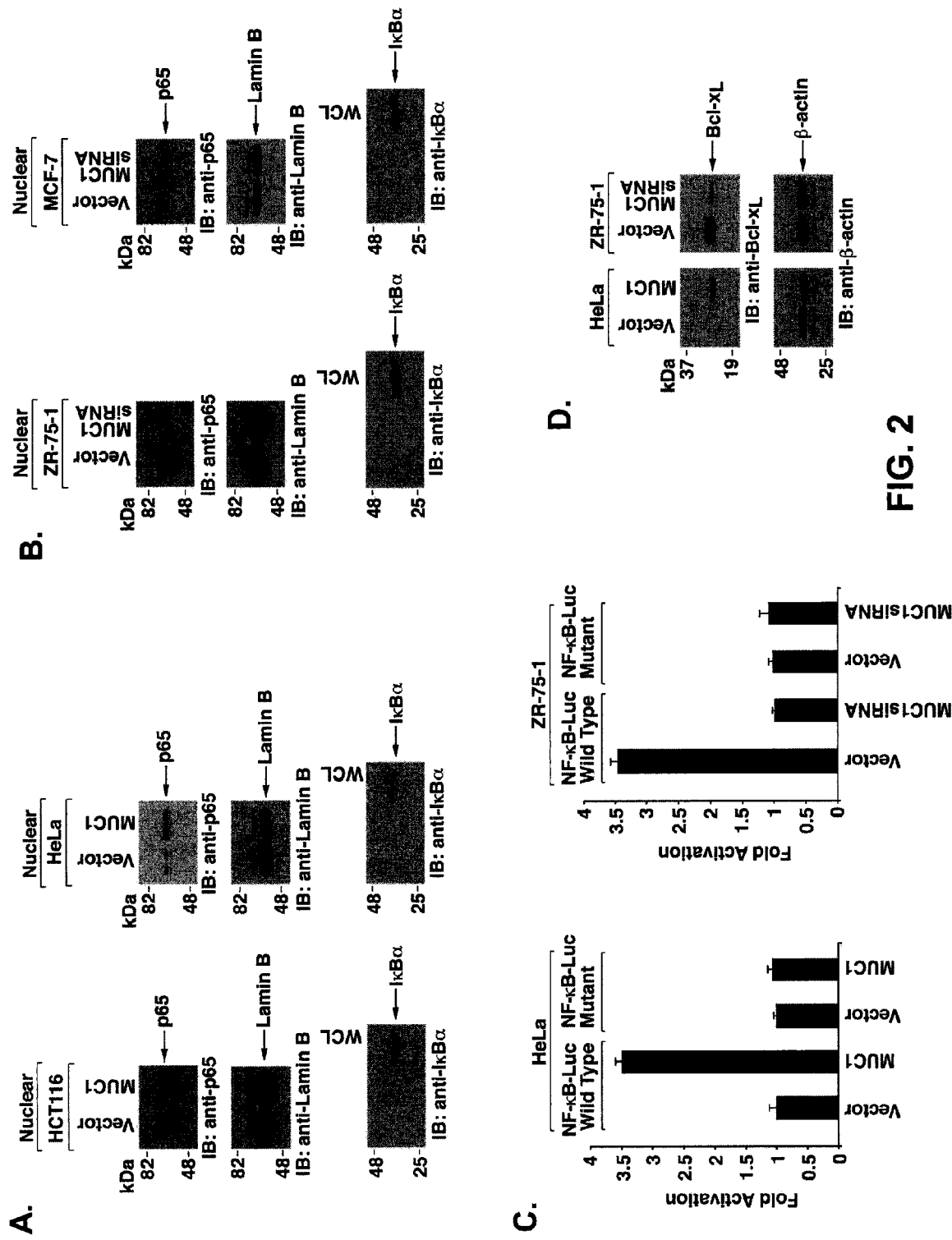
FIG. 2A is a series of photographs of immunoblots showing the amounts of nuclear NF-κB protein. Left panel: nuclear lysates were prepared from HeLa cells stably transfected either with a vector encoding MUC1 (HeLa/MUC1) or an empty vector (HeLa/Vector). Right panel: nuclear lysates were prepared from HCT116 cells stably transfected with a vector encoding MUC1 (HCT116/MUC1) or an empty vector (HCT116/Vector). In both panels, p65 protein was detected using an anti-p65 antibody and expression of lamin, as a control, was detected with an anti-lamin antibody. As a further control for quality of fractionation, expression of IκBα was also determined (bottom panels) by immunoblotting using an anti-IκBα antibody (absent in the nuclear fraction, but present in whole cell lysate (WCL)). The molecular weights of proteins (as indicated on the left of the photographs) are expressed as kilodaltons (kDa).
FIG. 2B is a series of photographs of immunoblots showing the amount of nuclear NF-κB protein. Left panel: nuclear lysates were prepared from ZR-75-1 cells stably transfected either with a vector encoding a MUC1-specific siRNA (ZR-75-1/MUC1siRNA) or an empty vector (ZR-75-1/Vector). Right panel: nuclear lysates were prepared from MCF7 cells stably transfected either with a vector encoding a MUC1-specific siRNA(MCF7/MUC1siRNA) or an empty vector (MCF7/Vector). For both panels, p65 protein was detected by western blotting using an anti-p65 antibody and expression of lamin, as a control, was detected with an anti-lamin antibody. As a further control for quality of fractionation, expression of IκBα was also determined (bottom panels) by western blotting using an anti-IκBα antibody (absent in the nuclear fraction, but present in whole cell lysate (WCL)). The molecular weights of proteins (as indicated on the left of the photographs) are expressed as kilodaltons (kDa).
FIG. 2C is a pair of bar graphs depicting the fold-activation in expression of a luciferase reporter driven by an NF-κB promoter. Left graph: HeLa cells were transfected with a pNF-κB-Luc reporter plasmid or a pNF-κB-luc reporter plasmid containing a mutant NF-κB binding site. Right graph: ZR-75-1 cells were transfected with a pNF-κB-Luc reporter plasmid or a pNF-κB-luc reporter plasmid containing a mutant NF-κB binding site. For both graphs, as a control, the SV40-*Renilla*-Luc plasmid was used. Luciferase activity was measured at 48 h after transfection. The results are expressed as the fold activation (mean±SD of 3 separate experiments) compared to that obtained in HeLa/vector (left) or ZR-75-1/MUC1siRNA (right) cells (each assigned a value of 1). The molecular weights of proteins (as indicated on the left of the photographs) are expressed as kilodaltons (kDa).
FIG. 2D is a series of photographs of immunoblots showing Bcl-$x_L$ expression. Whole cell lysates were prepared from HeLa/Vector and HeLa/MUC1 cells (left panel), or ZR-75-1/Vector and ZR-75-1/MUC1siRNA cells (right panel), and were immunoblotted using antibodies against Bcl-$x_L$ and β-actin as indicated. The molecular weights of proteins (as indicated on the left of the photographs) are expressed as kilodaltons (kDa).

Nuclear localization of NF-κB p65 was studied in HCT116 colon cancer cells that were stably transfected with an empty vector or a vector (i.e., HCT116/vector cells) containing a MUC1 coding sequence (i.e., HCT116/MUC1 cells), as described in Ren et al. (2004) Cancer Cell 5:163-175, and shown in FIG. 1. As shown in FIG. 1A, levels of nuclear p65 were decreased in HCT116/vector cells compared to that in HCT116/MUC1 cells. Immunoblot analysis of the nuclear lysates obtained from the HCT116/vector and HCT116/MUC1 cells, with antibodies against nuclear lamin B (used as a control) and cytosolic IκBα confirmed equal loading of the lanes and a lack of cytoplasmic contamination (see FIG. 1A, left panel). Nuclear localization of NF-κB p65 was also studied in HeLa cervical carcinoma cells that were stably transfected with an empty vector or a vector (i.e., HeLa/vector cells) containing a MUC1 coding sequence (i.e., HeLa/MUC1 cells). As shown in FIG. 2A (right panel), immunoblot analysis revealed that the levels of nuclear p65 were decreased in HeLa/vector cells compared to that in HeLa/MUC1 cells, similar to the results obtained with the stable HCT116 cells (see also FIG. 1). Human ZR-75-1 breast cancer cells, that express endogenous MUC1, were stably transfected with an empty vector (ZR-75-1/vector cells) or a vector encoding a MUC1siRNA (ZR-75-1/MUC1siRNA cells), as described in Ren et al. (2004) Cancer Cell 5:163-175, and depicted in FIG. 1. As shown in FIG. 2B (left panel), nuclear p65 was detectable constitutively in ZR-75-1/vector cells and was decreased by silencing with MUC1 siRNA. Analysis of separately isolated ZR-75-1/MUC1siRNA clones demonstrated similar decreases in nuclear p65. NF-κB is constitutively activated in human MCF-7 breast cancer cells (FIG. 2B, right panel). Moreover, silencing MUC1 in MCF-7 cells, as shown in FIG. 1, decreased nuclear NF-κB p65 (see FIG. 2B, right panel). In concert with these results, MUC1 expression was associated with a decrease in cytosolic NF-κB p65 levels in HCT116, HeLa, ZR-75-1 and MCF-7 cells. To determine if MUC1-induced targeting of NF-κB p65 to the nucleus is associated with activation of the NF-κB p65 transcription function, HeLa/vector and HeLa/MUC1 cells were transfected with a construct containing an NF-κB binding site (e.g., a NF-κB promoter) upstream to the luciferase reporter gene (pNF-κB-Luc). MUC1 expression was associated with activation of pNF-κB-Luc (FIG. 2C, left panel). In contrast, MUC1 had no effect on activation of a pNF-κB-Luc construct that contained a mutated NF-κB p65 binding site (FIG. 2C, left panel). Silencing MUC1 in ZR-75-1 cells also resulted in a decreased transcription of the luciferase from the NF-κB reporter gene (FIG. 1C, right panel). The Bcl-$x_L$ gene is activated by NF-κB (see, for example, Chen et al. (2000) Mol. Cell. Biol. 20:2687-2695. Immunoblot analysis of lysates prepared from HeLa/MUC1 and HeLa/vector cells showed that Bcl-$x_L$ expression is higher in HeLa/MUC1, as compared to HeLa/vector, cells (FIG. 2D, left panel). In addition, silencing MUC1 in ZR-75-1 cells decreased Bcl-$x_L$ expression (FIG. 2D, right panel). These findings indicate that MUC1 targets NF-κB p65 to the nucleus and thereby activates NF-κB p65-mediated transcription.

Example 3

MUC1 Induces IκBα Phosphorylation and Degradation

Figure 3:
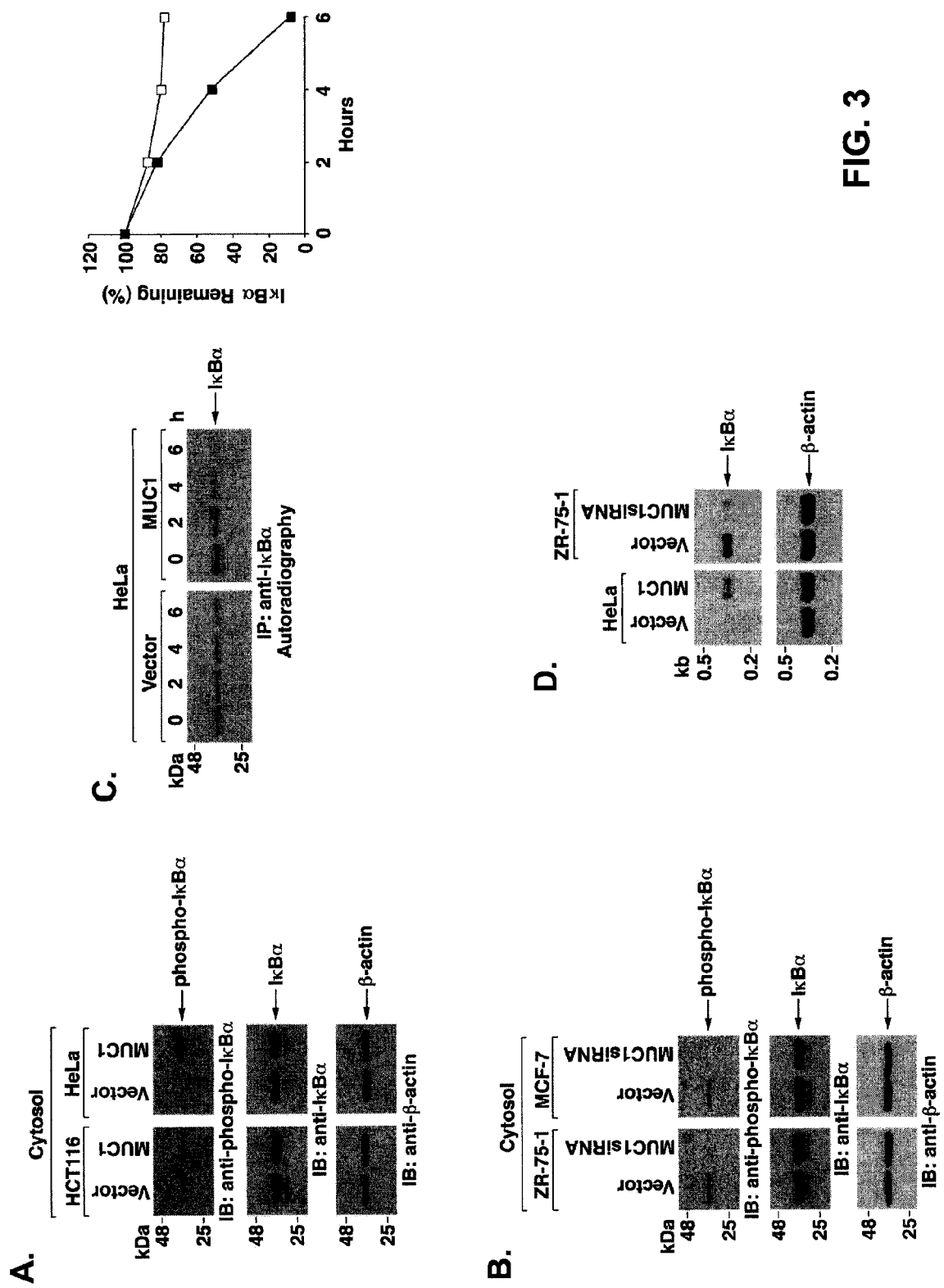
FIG. 3A is a series of photographs of immunoblots showing the amount of phosphorylated IκBα in cytosols. Cytosolic fractions were prepared from HCT116/Vector and HCT116/MUC1 cells (left panel), or HeLa/Vector and HeLa/MUC1 cells (right panel), and phospho-IκBα was determined by western blotting using anti-phospho-IκBα antibodies. As loading controls, total IκBα and β-actin were also probed using antibodies specific for each protein. The molecular weights of proteins (as indicated on the left of the photographs) are expressed as kilodaltons (kDa).
FIG. 3B is a series of photographs of immunoblots showing the amount of phosphorylated IκBα in cytosols. Left panel: cytosolic fractions were prepared from ZR-75-1/Vector and ZR-75-1/MUC1siRNA cells, and total phospho-IκBα protein was determined by immunoblotting using an antibody specific for phospho-IκBα. Right panel: cytosolic fractions were prepared from MCF-7/Vector and MCF-7/MUC1siRNA cells, and total phospho-IκBα protein was determined by immunoblotting using an antibody specific for phospho-IκBα. As loading controls, total IκBα and β-actin protein levels were determined by immunoblotting using antibodies specific for each protein. The molecular weights of proteins (as indicated on the left of the photographs) are expressed as kilodaltons (kDa).
FIG. 3C is a pair of photographs of autoradiograms and a graph. HeLa/vector and HeLa/MUC1 cells were pulsed with [$^{35}$S]-methionine and chased for the indicated times. Anti-IκBα immunoprecipitates from equal amounts of lysate were subjected to SDS-polyacrylamide gel electrophoresis (PAGE) and autoradiography (left). Intensity of the IκBα signals was determined by scanning densitometry and is expressed as the percentage IκBα remaining compared to that obtained at 0 h (right). Similar results were obtained in two separate experiments. The molecular weights of proteins (as indicated on the left of the photographs) are expressed as kilodaltons (kDa). The graph at the right of the figure is a plot of the amount of IκBα remaining in the HeLa/vector (open squares) or HeLa/MUC1 cells (closed squares) following the pulse-chase experiment described above. The percentage values depicted in the graph were determined by quantitation of the signal intensity of the bands in the left audioradiograms.
FIG. 3D is a series of photographs of immunoblots showing the amount of IκBα protein. Left panel: total cell lysates were prepared from stable HeLa cell lines (HeLa/Vector and HeLa/MUC1) and IκBα levels were determined by immunoblotting using antibodies specific for IκBα. Right panel: total cell lysates were prepared from stable ZR-75-1 cell lines (ZR-75-1/Vector and ZR-75-1/MUC1siRNA), and IκBα protein levels were determined by immunoblotting using antibodies specific for IκBα. As a loading control, total β-actin protein was determined by immunoblotting using antibodies specific for β-actin protein. The molecular weights of proteins (as indicated on the left of the photographs) are expressed as kilodaltons (kDa).

NF-κB p65 is released from IκBα and targeted to the nucleus in response to phosphorylation of IκBα by the IκB kinase (IKK) complex. To determine if MUC1 affects IκBα phosphorylation, cytosolic lysates from HCT116 cells were immunoblotted with an anti-phospho-IκBα antibody. As shown in FIG. 3A (left panel), phospho-IκBα levels were significantly higher in HCT116/MUC1, as compared to HCT116/vector, cells. Phosphorylation of IκBα was also higher in HeLa cells that express MUC1 (FIG. 3A, right panel). Consistent with these results, silencing MUC1 in ZR-75-1 and MCF-7 cells decreased IκBα phosphorylation (FIG. 3B). Phosphorylated IκBα is targeted for ubiquitination and proteosomal degradation. To assess the stability of IκBα in the presence and absence of MUC1, the aforementioned HeLa/vector and HeLa MUC1 cells were pulsed with $^{35}$S-methionine and chased for 0 to 6 hours with un-labeled methionine. As depicted in FIG. 3C, analysis of lysates prepared from these cells showed that IκBα was more stable in the absence of exogenous MUC1 expression (i.e., a half-life of greater than 6 hours for HeLa/Vector), than in the presence of exogenous of MUC1 (i.e., half-life of ~4 hours). Under similar experimental conditions as described using ZR-75-1/vector and ZR-75-1/MUC1 cells, IκBα was also demonstrated to be less stable in the presence of exogenous MUC1. These results indicated that MUC1-induced increases in IκBα phosphorylation are associated with increases in IκBα degradation.

The IκBα gene is activated following translocation of NF-κB p65 to the nucleus, such that degradation of IκBα is accompanied by increases in IκBα transcription. Consistent with this autoregulatory loop, RT-PCR analysis demonstrated that MUC1-induced increases in nuclear NF-κB p65 are associated with upregulation of IκBα mRNA levels (FIG. 3D). These findings support a model where MUC1 contributes to IκBα degradation and thereby subsequent activation of NF-κB p65 and IκBα gene transcription.

Example 4

MUC1-C Binds to IKKβ and IKKγ in Cells and In Vitro

Figure 4:
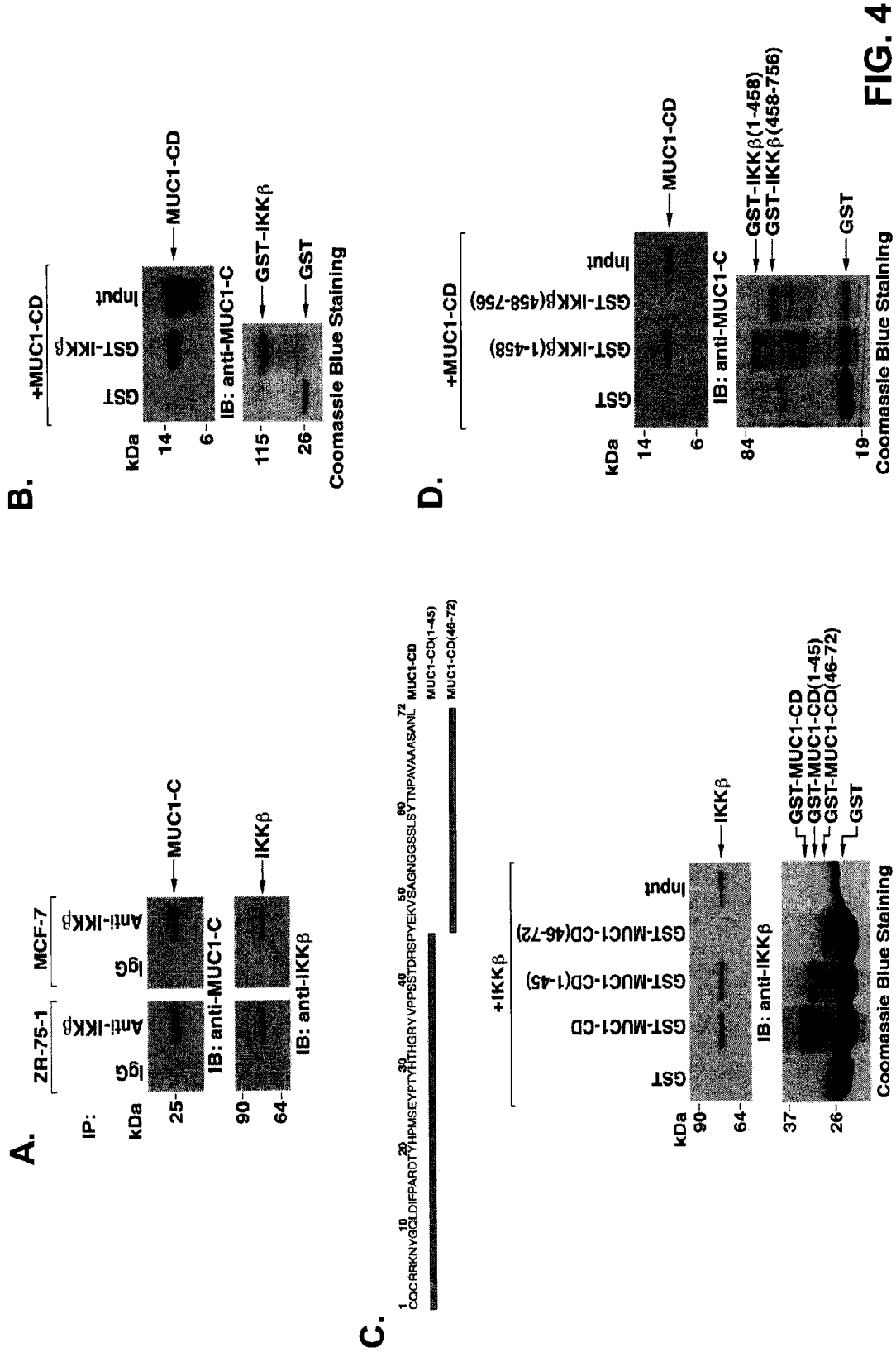
FIG. 4A is a series of photographs of immunoblots. Lysates were prepared from either ZR-75-1 cells (left) or MCF-7 cells (right) and subjected to immunoprecipitation (IP) with a control IgG antibody or an antibody specific for IKKβ. Associated MUC1-C protein was determined by immunoblotting (IB) using an antibody specific for MUC1-C. As a control, the amount of IKKβ immunoprecipitated was confirmed in each case by immunoblotting with an antibody specific for IKKβ. The molecular weights of proteins (as indicated on the left of the photographs) are expressed as kilodaltons (kDa).
FIG. 4B is a pair of photographs of immunoblots. Recombinantly expressed, purified GST- and GST-IKKβ proteins bound to glutathione-agarose beads were incubated with purified MUC1-CD protein. The precipitates were immunoblotted (IB) with anti-MUC1-C antibodies. Input of the GST and GST-IKKβ proteins was assessed by Coomassie blue staining. The molecular weights of proteins (as indicated on the left of the photographs) are expressed as kilodaltons (kDa).
FIG. 4C (top panel) is a schematic diagram of the amino acid sequence of (i) the MUC1-cytoplasmic domain (MUC1-CD) [amino acids 1-72; SEQ ID NO:2]; (ii) the MUC1-CD fragment [amino acids 1-45; SEQ ID NO:3]; and (iii) the MUC-CD fragment [amino acids 46-72; SEQ ID NO:4].
FIG. 4D is a pair of photographs of immunoblots. GST and the indicated GST-IKKβ fusion proteins bound to glutathione beads were incubated with MUC1-CD. The precipitates were immunoblotted with anti-MUC1-C antibody. The molecular weights of proteins (as indicated on the left of the photographs) are expressed as kilodaltons (kDa).

IKKβ is necessary and sufficient for phosphorylation of IκBα in the classical NF-κB pathway. To determine if endogenous MUC1 interacts with the IKK complex, lysates were prepared from ZR-75-1 and MCF-7 cells, IKKβ was immunoprecipitated from each of these lysates using anti-IKKβ antibodies, and immunoprecipitates were analyzed for the presence of MUC1-C by western blotting. As shown in FIG. 4A, MUC1-C associates with IKKβ in vivo. In vitro studies using recombinant, purified GST-IKKβ and the MUC1 cytoplasmic domain (MUC1-CD), further demonstrated that these proteins interact directly (FIG. 4B). This interaction was confirmed in reciprocal GST-pull down experiments using recombinant, purified MUC1 tagged with the GST moiety (i.e., GST-MUC1-CD) and untagged IKKβ (FIG. 4C). Studies with MUC1-CD(1-45) and MUC1-CD(46-72) fragments demonstrated that MUC1-CD amino acids 1-45 confers the ability to bind to IKKβ (FIG. 4C). Studies with IKKβ (1-458) and IKKβ (458-756) further demonstrated that MUC1 binds directly with the IKKβ N-terminal region (FIG. 4D).

Figure 5:
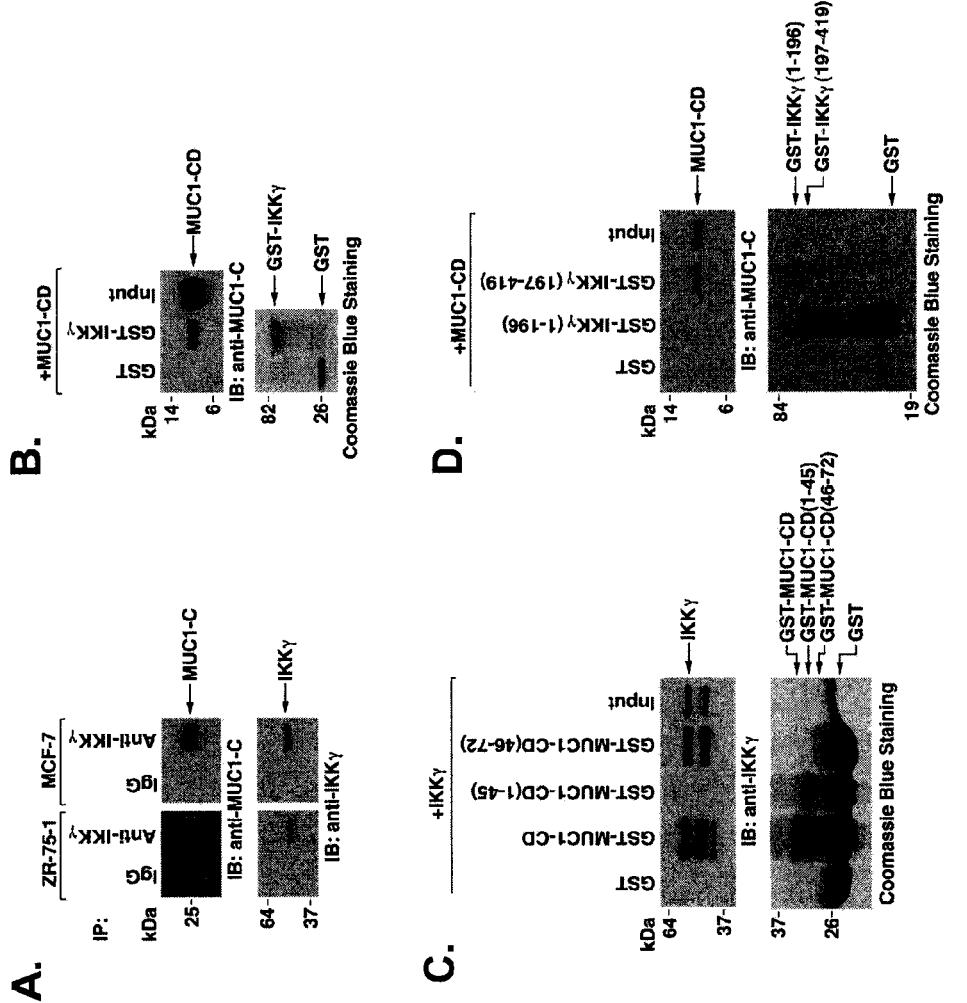
FIG. 5A is a pair of photographs of immunoblots showing MUC1 association with IKKγ. Lysates from ZR-75-1 cells (left) or MCF-7 cells (right) were subjected to immunoprecipitation (IP) with a control IgG or antibodies specific to IKKγ. The precipitates were immunoblotted (IB) with the anti-MUC1-CD antibodies and IKKγ antibodies as a loading control. The molecular weights of proteins (as indicated on the left of the photographs) are expressed as kilodaltons (kDa).
FIG. 5B is a pair of photographs of immunoblots showing an interaction between MUC1-CD and IKKγ. GST- and GST-IKKγ bound to glutathione beads were incubated with purified MUC1-CD. The precipitates were immunoblotted (IB) with anti-MUC1-C antibodies. Commassie blue staining of the gel was performed to confirm that equal amounts of GST- and GST-IKKγ were used in the experiment. The molecular weights of proteins (as indicated on the left of the photographs) are expressed as kilodaltons (kDa).
FIG. 5C is a pair of photographs of immunoblots. GST- and the indicated GST-MUC1-CD fusion proteins or fragments bound to glutathione beads were incubated with purified IKKγ. The precipitates were immunoblotted (IB) with anti-IKKγ antibody. Commassie blue staining of the gel was performed to confirm that equal amounts of GST- and GST-MUC1 proteins were used in the experiment. The molecular weights of proteins (as indicated on the left of the photographs) are expressed as kilodaltons (kDa).
FIG. 5D is a pair of photographs of immunoblots. GST and the indicated GST-IKKγ fusion proteins bound to glutathione beads were incubated with MUC1-CD. The precipitates were immunoblotted (IB) with anti-MUC1-C antibody. Commassie blue staining of the gel was performed to confirm that equal amounts of GST- and GST-IKKγ proteins were used in the experiment. The molecular weights of proteins (as indicated on the left of the photographs) are expressed as kilodaltons (kDa).
FIG. 5E is a diagram showing a model of the MUC1-IKK complex. Potential binding of MUC1-CD, IKKβ and IKKγ is depicted in a trimolecular complex. Also indicated are the regions of the three proteins determined to interact. "C" indicates the carboxy-terminus of a depicted protein and "N" indicates the amino-terminus of a depicted protein.
Figure 6:
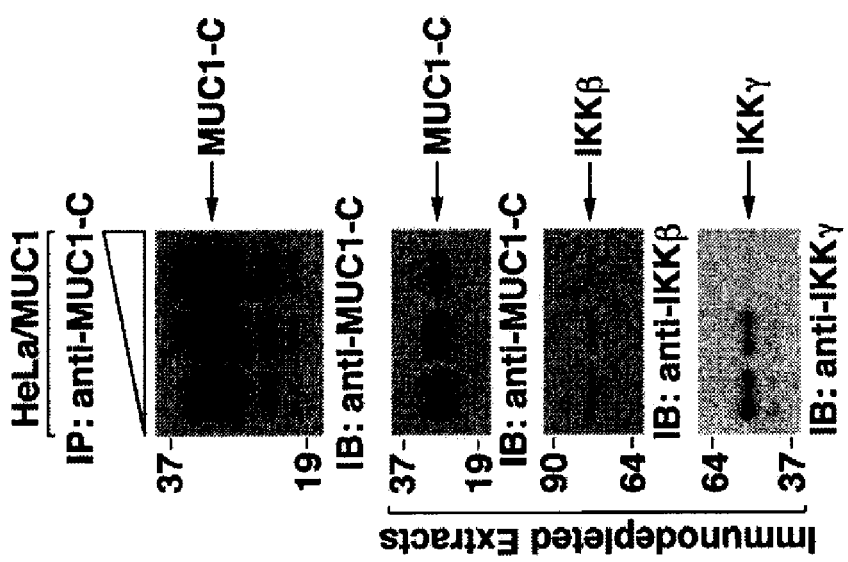
FIG. 6 is a series of photographs of immunoblots. Lysates from HeLa/MUC1 cells were immunoprecipitated with increasing amounts (from left to right) of anti-MUC1-C antibody. The immunoprecipitates (IP) were immunoblotted (IB) with anti-MUC1-C antibodies (upper panel). The MUC1-C immunodepleted lysates were also immunoblotted with antibodies specific for MUC1-C, IKKβ, and IKKγ (middle and lower panels). The molecular weights of proteins (as indicated on the left of the photographs) are expressed as kilodaltons (kDa).

The IKKβ C-terminal region associates with the N-terminal region of IKKγ (see, for example, May et al. (2000) Science 289:1550-1554). Consistent with the formation of IKKβ-IKKγ complexes and binding of MUC1 to IKKβ, we found that MUC1-C coprecipitates with IKKγ (FIG. 5A). Moreover, as shown in FIG. 5B, in vitro interaction studies (i.e., GST-pull downs) using purified, recombinant GST-IKKγ demonstrated that MUC1-CD binds to purified IKKγ. However, in contrast to the interaction with IKKβ, MUC1-CD(46-72), but not MUC1-CD(1-45), binds to IKKγ (FIG. 5C). Moreover, in vitro GST-pull down experiments using GST-IKKγ demonstrated that the MUC1-CD binds to the C-terminal region (197-419) of IKKγ (FIG. 5D). To further assess binding of MUC1-C to IKKβ and IKKγ in vivo, MUC1-C was immunodepleted from HeLa/MUC1 cell lysates by immunoprecipitation with increasing amounts of anti-MUC1-C antibody (FIG. 6). As depicted in FIG. 6, immunoblot analysis of the immunoprecipitated lysates demonstrated that depletion of MUC1-C is associated with decreases in IKKβ and IKKγ. While the disclosure is not limited by any particular mode of action, these findings support a model where MUC1 binds directly to IKKβ and IKKγ, and potentially to both proteins in IKKβ-IKKγ complexes (FIG. 5E).

Example 5

MUC1-C Associates with the IKK Complex and Induces IKKβ Activity

Figure 7:
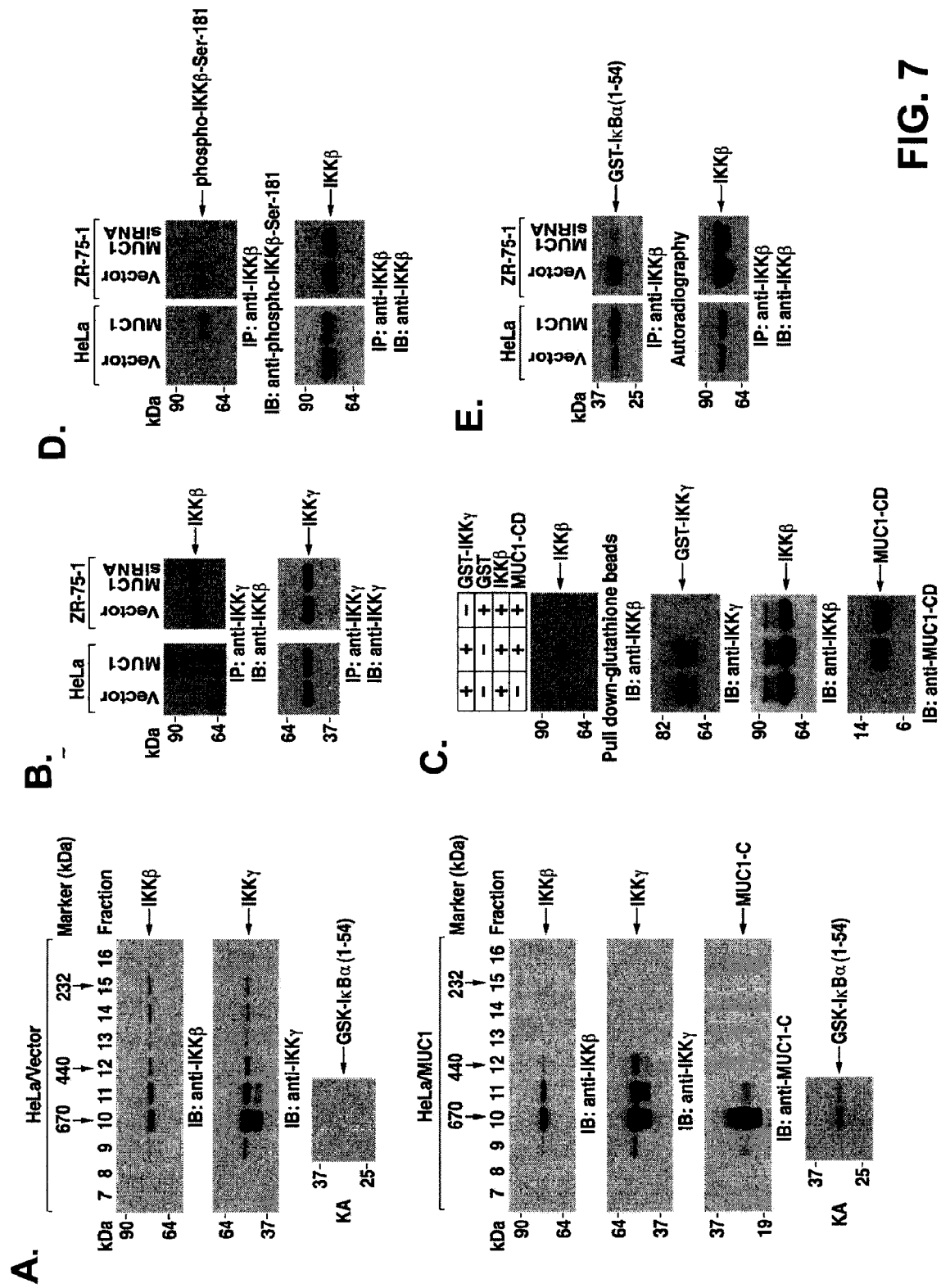
FIG. 7A is a series of photographs of immunoblots. HeLa/vector (top panel) and HeLa/MUC1 (bottom panel) cell lysates were passed over a Sephacryl S-200 HR column, and the protein complexes separated by size (kDa). Selected column fractions were analyzed by immunoblotting with antibodies specific for IKKβ and IKKγ. Size standards (Markers) are indicated above each of the immunoblot panels. The fractions were also incubated with GST-IκBα(1-54) and [γ-$^{32}$P] ATP in kinase assays (KA). The reaction products were analyzed by SDS-PAGE and autoradiography. The molecular weights of proteins (as indicated on the left of the photographs) are expressed as kilodaltons (kDa).
FIG. 7B is a series of photographs of immunoblots. Left panel: lysates were prepared from HeLa/Vector and HeLa/MUC1 cells and subjected to immunoprecipitation using anti-IKKγ antibodies. Right panel: lysates were prepared from ZR-75-1/Vector and ZR-75-1/MUC1siRNA cells and subjected to immunoprecipitation using anti-IKKγ antibodies. Anti-IKKγ immunoprecipitates from the indicated cells were immunoblotted with anti-IKKβ and IKKγ antibodies where indicated. The molecular weights of proteins (as indicated on the left of the photographs) are expressed as kilodaltons (kDa).
FIG. 7C is a series of photographs of immunoblots. GST- or GST-IKKγ bound to glutathione beads was incubated with IKKβ in the absence and presence of MUC1-CD protein. The precipitates were immunoblotted (IB) with anti-IKKβ (upper panel). Input amounts of the various proteins were assessed by immunoblotting with the indicated antibodies (lower 3 panels). The molecular weights of proteins (as indicated on the left of the photographs) are expressed as kilodaltons (kDa).
FIG. 7D is a series of photographs of immunoblots. Lysates were prepared from HeLa/Vector and HeLa/MUC1 cells (left panel), or ZR-75-1/Vector and ZR-75-1/MUC1siRNA cells (right panel) and subjected to immunoprecipitation using anti-IKKβ antibodies. Precipitates from the indicated cells were immunoblotted with anti-phospho-IKKβ-Ser-181 and anti-IKKβ antibodies. The molecular weights of proteins (as indicated on the left of the photographs) are expressed as kilodaltons (kDa).
FIG. 7E is a series of photographs of immunoblots. Lysates were prepared from HeLa/Vector and HeLa/MUC1 cells (left panel), or ZR-75-1/Vector and ZR-75-1/MUC1siRNA cells (right panel), and anti-IKKβ precipitates from the indicated cells were incubated with GST-IκBα(1-54) and [γ-$^{32}$P]ATP. The reaction products were analyzed by SDS-PAGE and autoradiography (upper panels). The precipitates were also immunoblotted with anti-IKKβ (lower panels). The molecular weights of proteins (as indicated on the left of the photographs) are expressed as kilodaltons (kDa).
Figure 8:
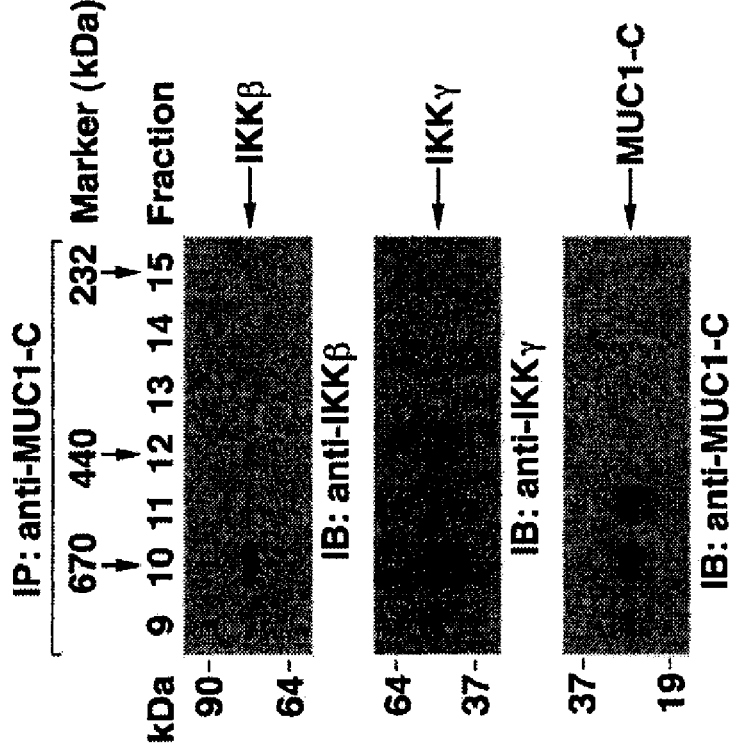
FIG. 8 is a series of photographs of immunoblots showing gel filtration chromatography of MUC1-C, IKKβ and IKKγ complexes. Lysates from HeLa/MUC1 cells were precipitated with anti-MUC1-C and protein G beads. The precipitates were incubated with MUC1-C peptide (NeoMarkers) to release the complexes and the supernatant fraction was separated in a Sephacryl S-200 HR column. The column fractions were immunoblotted with the indicated antibodies. Size standards (in kDa, indicated as "Marker") for the column are displayed above the immunoblot. The molecular weights of proteins (as indicated on the left of the photographs) are expressed as kilodaltons (kDa).
Figure 11:
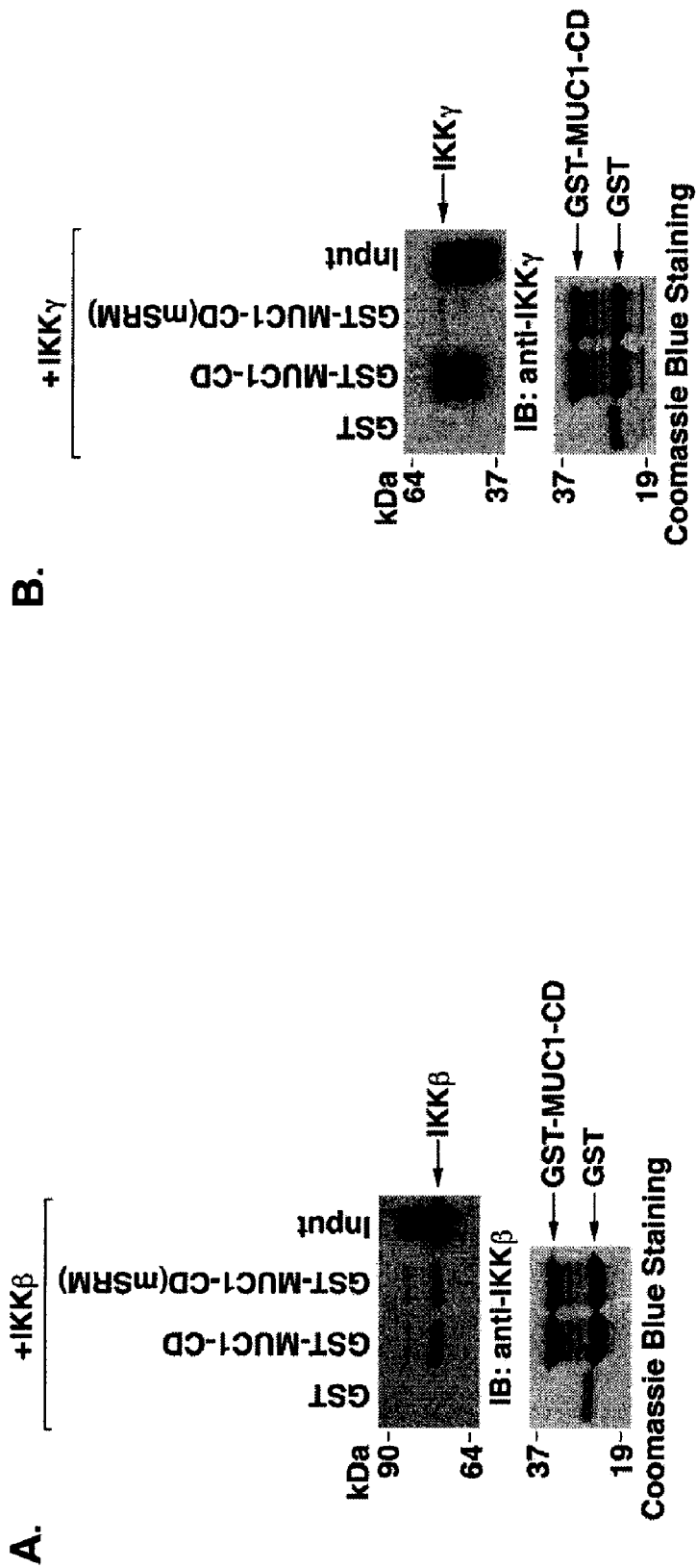
FIG. 11A is a pair of photographs of an immunoblot and Coomassie-blue stained gel. GST and the indicated GST-MUC1-CD fusion proteins (MUC1-CD and MUC1-CD (mSRM)) bound to glutathione beads were incubated with IKKβ. The precipitates were immunoblotted (IB) with an anti-IKKβ antibody. Commassie blue staining of the gel was performed to confirm that equal amounts of GST- and GST-MUC1-CD proteins were used in the experiment. The molecular weights of proteins (as indicated on the left of the photographs) are expressed as kilodaltons (kDa).
FIG. 11B is a pair of photographs of an immunoblot and Coomassie blue stained gel. GST and the indicated GST-MUC1-CD fusion proteins (MUC1-CD and MUC1-CD (mSRM)) bound to glutathione beads were incubated with IKKγ. The precipitates were immunoblotted (IB) with an anti-IKKγ antibody. Commassie blue staining of the gel was performed to confirm that equal amounts of GST- and GST-MUC1-CD proteins were used in the experiment. The molecular weights of proteins (as indicated on the left of the photographs) are expressed as kilodaltons (kDa).
Figure 12:
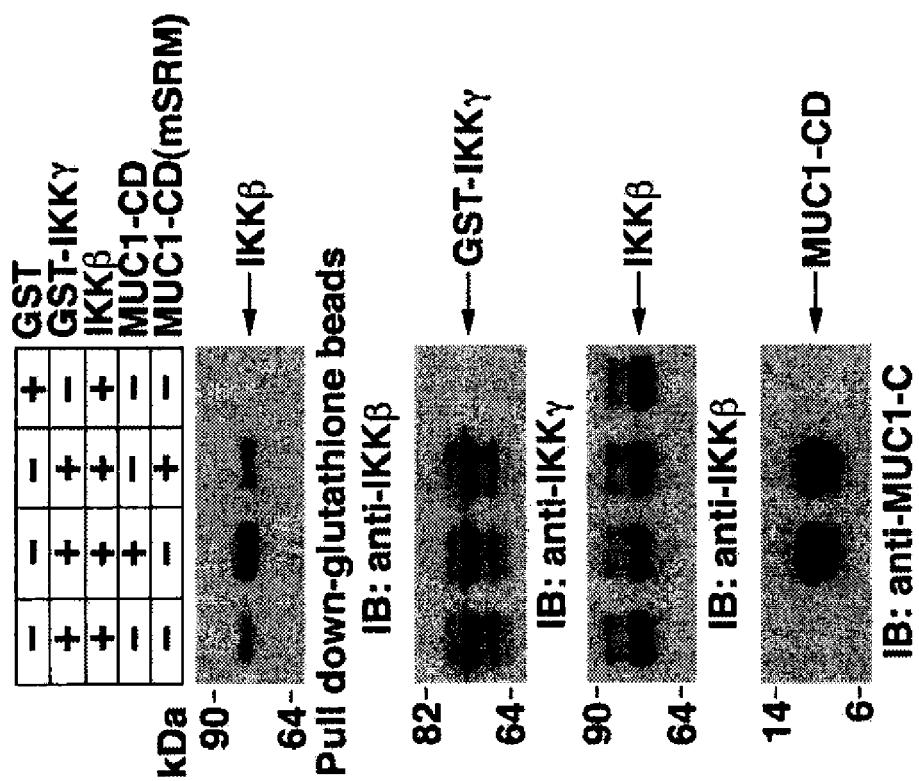
FIG. 12 is a series of photographs of immunoblots. GST, and GST-IKKγ fusion proteins bound to glutathione beads were incubated with MUC1-CD, MUC1-CD(mSRM), or IKKβ proteins as indicated. The GST-pull down precipitates were immunoblotted (IB) with antibodies specific for IKKγ (top panel), IKKβ (middle panel), or MUC1 (bottom panel) as indicated. The molecular weights of proteins (as indicated on the left of the photographs) are expressed as kilodaltons (kDa).
Figure 13:
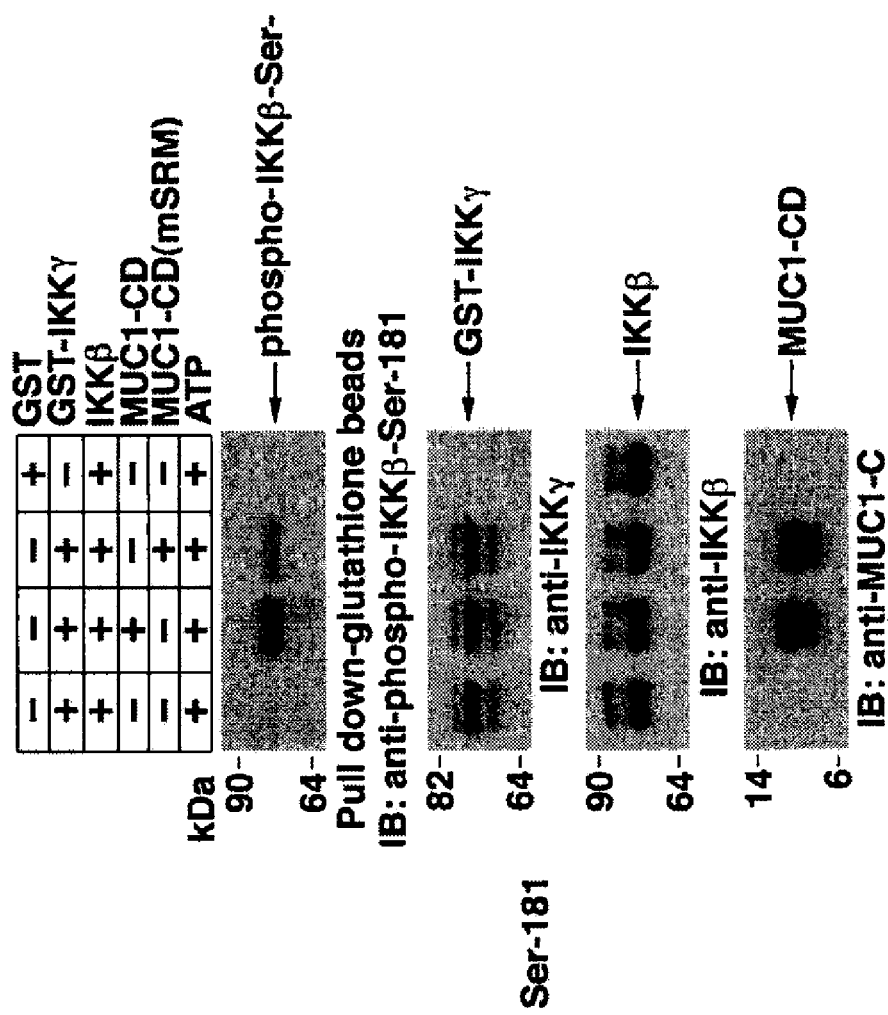
FIG. 13 is a series of photographs of immunoblots. GST, and GST-IKKγ fusion proteins bound to glutathione beads were incubated with MUC1-CD, MUC1-CD(mSRM), or IKKβ proteins as indicated. The GST-pull down precipitates were immunoblotted (IB) with antibodies specific for (from top to bottom) phosphor-IKKβ-Ser-181 (first panel), IKKγ (second panel), IKKβ (third panel), or MUC1 (fourth panel) as indicated. The molecular weights of proteins (as indicated on the left of the photographs) are expressed as kilodaltons (kDa).

IKKβ and IKKγ localize intracellularly to a large ~700 kDa multiprotein IKK complex in the absence of signals that activate the classical NF-κB pathway (see, for example, Hayden et al. (2004) Genes Dev. 18:2195-2224). To determine whether MUC1-C associates with the multiprotein IKK complex, lysates from HeLa/vector and HeLa/MUC1 cells were subjected to gel filtration chromatography, followed by immunoblotting the fractions with antibodies to both IKKβ and IKKγ. As depicted in FIG. 7A, analysis of HeLa/vector cells showed that IKKβ and IKKγ are detectable in a prominent ~700 kDa pool (fractions 10-12), and also in a pool of ~300 kDa (fractions 13 and 14) (see FIG. 7A). Analysis of HeLa/MUC1 cells showed that IKKβ and IKKγ are detectable in fractions 10-12, but not in fractions 13 and 14 (see FIG. 7A). In addition, MUC1-C was found largely in fraction 10, consistent with binding to the large ~700 kDa complex (FIG. 7A). Notably, the ~700 kDa IKKβ/IKKγ complexes exhibited little if any kinase activity (FIG. 7A). By contrast, as depicted in FIG. 7A, analysis of these complexes from HeLa/MUC1 cells demonstrated constitutive activation. The HeLa/MUC1 lysates were also immunoprecipitated using anti-MUC1-C antibodies, and the precipitates were subjected to gel filtration chromatography. Immunoblot analysis of the resulting fractions confirmed that MUC1-C associates with the large IKKβ-IKKγ complexes (see FIG. 8). IKKγ binds directly to IKKβ and is required for IKKβ activation (see, for example, Rothwarf et al. (1998) Nature 395:297-300; and Makris et al. (2002) Mol. Cell. Biol. 22:6573-6581). To determine if MUC1 affects binding of IKKβ to IKKγ, anti-IKKγ precipitates from HeLa cells were immunoblotted with anti-IKKγ antibodies. As shown in FIG. 7B (left panel), MUC1 expression was associated with increased binding of IKKβ to IKKγ. Further analysis of ZR-75-1 cells also demonstrated that the silencing of MUC1 expression decreases the interaction between IKKβ and IKKγ (FIG. 7B, right). Moreover, in vitro incubation of purified IKKβ and IKKγ in the presence and absence of purified MUC1 protein, demonstrated that MUC1-CD increases the interaction between IKKβ and IKKγ (FIG. 7C). MUC1-CD(1-45) binds to IKKβ and MUC1-CD (46-72), which contains a serine-rich SAGNGGSSLS motif (SRM; amino acids 50-59) (SEQ ID NO:13), binds to IKKγ. Mutation of the SRM to AAGNGGAAAA (mSRM) (SEQ ID NO: 14) had no effect on the interaction between MUC1-CD and IKKβ (FIG. 11A), but attenuated binding to IKKγ (FIG. 11B). Compared with MUC1-CD, we found that MUC1-CD (mSRM) is substantially less effective in inducing the association of IKKβ and IKKγ (FIG. 12), indicating that this response is dependent on binding of both IKKs to MUC1-CD. Phosphorylation of IKKβ on Ser-181 in the activation loop, potentially through a trans-autophosphorylation mechanism, is required for induction of IKKβ activity (see, for example, Delhase et al. (1999) 284:309-313; and Inohara et al. (2000) J. Biol. Chem. 275:27823-27831). Immunoblot analysis with an antibody against phospho-Ser-181, showed that IKKβ is phosphorylated on Ser-181 by a MUC1-dependent mechanism in HeLa (FIG. 7D, left panel) and ZR-75-1 (FIG. 7D, right panel) cells. Consistent with these results, analysis of IκBα phosphorylation using IKKβ proteins (anti-IKK immunoprecipitates) prepared from HeLa and ZR-75-1 cell lysates, further demonstrated that MUC1 stimulates the IKKβ kinase function (FIG. 7E). Analysis of anti-IKKβ precipitates from HeLa and ZR-75-1 cells for phosphorylation of IκBα further demonstrated that MUC1 stimulates the IKKβ kinase function. In vitro incubation of IKKβ and IKKγ with ATP was associated with phosphorylation of IKKγ on Ser-181 (FIG. 13). The extent of IKKβ phosphorylation was increased significantly by adding MUC1-CD to the reaction (FIG. 13). Moreover, this effect of MUC1-CD was attenuated by mutation of the SRM (FIG. 13).

Example 6

MUC1-C Cytoplasmic Domain Activates IKKβ/NF-κB p65 Signaling

Figure 9:
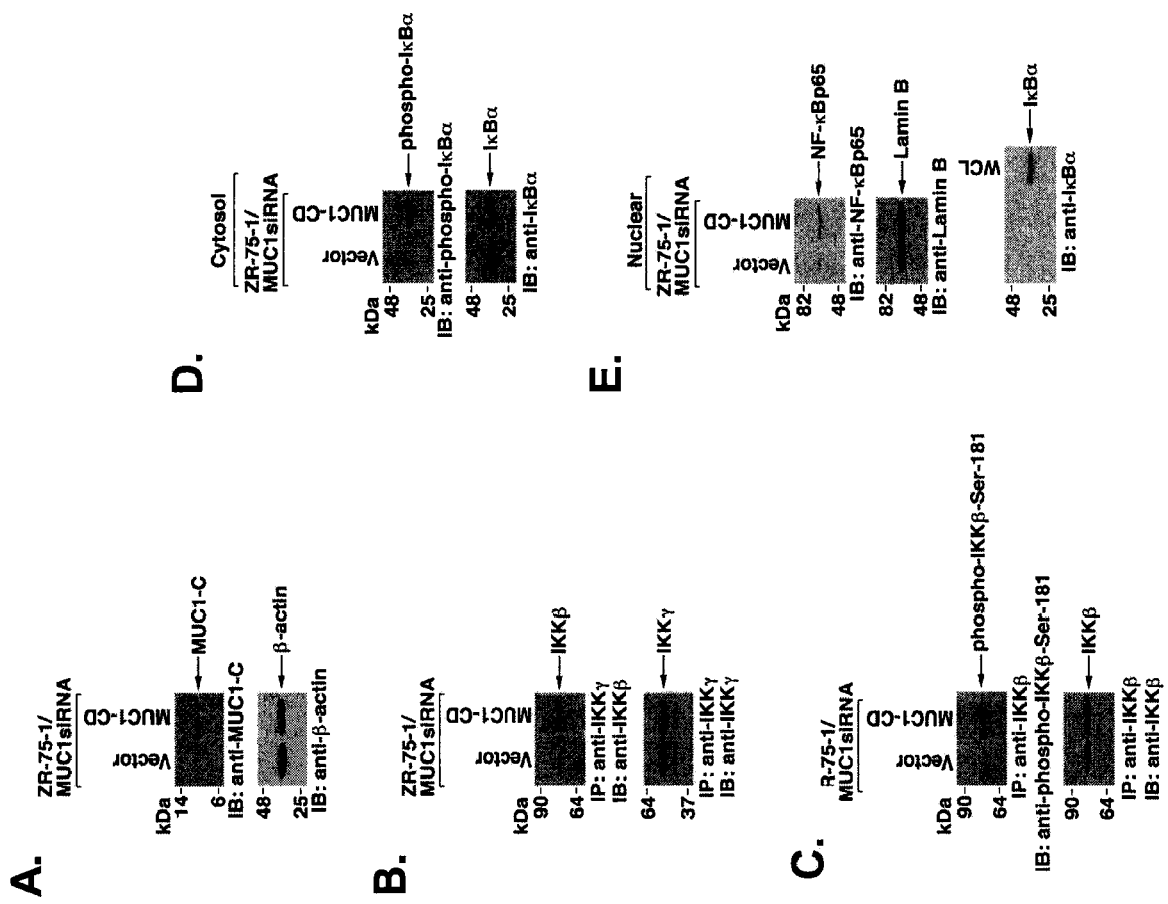
FIG. 9A is a pair of photographs of immunoblots. ZR-75-1/MUC1siRNA cells were transfected with the empty pIRES-puro2 vector or a pIRES-puro2-Flag-MUC1-CD vector. Lysates were prepared from the cells and subjected to SDS-PAGE and immunoblotting using antibodies specific to MUC1-C or β-actin as a control. The molecular weights of proteins (as indicated on the left of the photographs) are expressed as kilodaltons (kDa).
FIG. 9B is a pair of photographs of immunoblots. ZR-75-1/MUC1siRNA cells were transfected with the empty pIRES-puro2 vector or a pIRES-puro2-Flag-MUC1-CD vector. Lysates were prepared from the cells and subjected to immunoprecipitation using antibodies specific to IKKγ. Immunoprecipitates were immunoblotted using antibodies specific for IKKβ or IKKγ as indicated. The molecular weights of proteins (as indicated on the left of the photographs) are expressed as kilodaltons (kDa).
FIG. 9C is a pair of photographs of immunoblots. ZR-75-1/MUC1siRNA cells were transfected with the empty pIRES-puro2 vector or a pIRES-puro2-Flag-MUC1-CD vector. Lysates were prepared from the cells and subjected to immunoprecipitation using antibodies specific for IKKβ. Immunoprecipitates were immunoblotted using antibodies specific for phospho-IKKβ-ser-181 or IKKβ as indicated. The molecular weights of proteins (as indicated on the left of the photographs) are expressed as kilodaltons (kDa).
FIG. 9D is a pair of photographs of immunoblots. Cytosolic fractions were prepared from ZR-75-1/MUC1siRNA cells transfected with the empty pIRES-puro2 vector or a pIRES-puro2-Flag-MUC1-CD vector. Lysates were immunoblotted with anti-phospho-IκBα and anti-IκBα antibodies where indicated. The molecular weights of proteins (as indicated on the left of the photographs) are expressed as kilodaltons (kDa).
FIG. 9E is a photograph of an immunoblot. Nuclear fractions were prepared from ZR-75-1/MUC1siRNA cells transfected with the empty pIRES-puro2 vector or a pIRES-puro2-Flag-MUC1-CD vector and subjected to immunoblotting with antibodies specific for NF-κB or lamin B as a control. As a further control for the quality of nuclear fractionation, immunoblotting for IκBα was performed using antibodies specific for IκBα. The molecular weights of proteins (as indicated on the left of the photographs) are expressed as kilodaltons (kDa).

To determine if the association between the MUC1 cytoplasmic domain and the IKKβ-IKKγ complex is sufficient to activate the NF-κB p65 pathway, we transfected ZR-75-1/MUC1siRNA cells with a vector that allows expression of a Flag-tagged MUC1-CD polypeptide. The MUC1 siRNA used to silence endogenous MUC1 in the ZR-75-1 cells targets the extracellular region of MUC1-C and not the cytoplasmic domain (Ren et al. (2004) Cancer Cell 5:163-175). As seen in FIG. 9B, compared to ZR-75-1/MUC1siRNA cells transfected with the empty vector, expression of MUC1-CD in the ZR-75-1/MUC1siRNA cells was associated with increases in IKKβ-IKKγ complex formation. Expression of MUC1-CD was also associated with increased phosphorylation of IKKβ on Ser-181 and of IκBα (see FIGS. 9C and 9D). Moreover, as shown in FIG. 9E, MUC1-CD expression in ZR-75-1/MUC1siRNA cells increased targeting of NF-κB p65 to the nucleus. These findings indicate that MUC1-CD is sufficient to activate the classical IKKβ/NF-κB p65 pathway.

Example 7

MUC1-C Activates IKKβ/NF-κB p65 Signaling in the Response of Nontransformed MCF-10A Cells to TNFα

Figure 10:
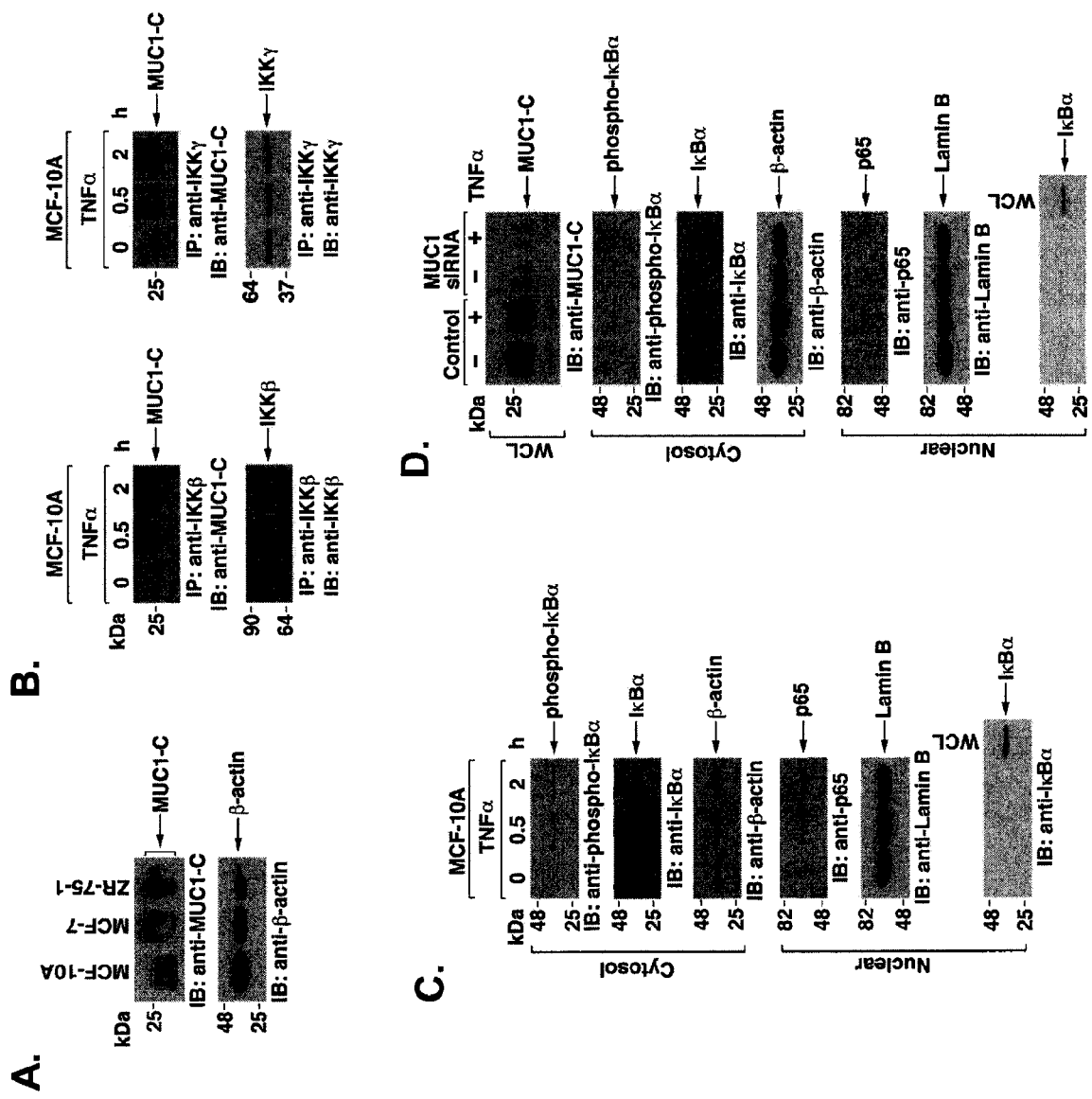
FIG. 10A is a pair of photographs of immunoblots. Lysates were prepared from MCF-10A, MCF-7, and ZR-75-1 cells and subjected to immunoblotting with anti-MUC1-C and anti-β-actin antibodies. The molecular weights of proteins (as indicated on the left of the photographs) are expressed as kilodaltons (kDa).
FIG. 10B is a pair of photographs of immunoblots. Lysates from MCF-10A cells left untreated (0) or stimulated with 20 ng/ml TNFα for the indicated times (0.5, or 2 hours) were immunoprecipitated with anti-IKKβ (left) or anti-IKKγ (right). The immunoprecipitates were immunoblotted with antibodies specific to MUC1-C, and either IKKβ (left panel) or IKKγ (right panel) as loading controls. The molecular weights of proteins (as indicated on the left of the photographs) are expressed as kilodaltons (kDa).
FIG. 10C is a series of photographs of immunoblots. MCF-10A cells were left untreated (0) or stimulated with 20 ng/ml TNFα for the indicated times. Cytosolic and nuclear fractions of the cells were prepared and subjected to immunoblotting with the indicated antibodies. The molecular weights of proteins (as indicated on the left of the photographs) are expressed as kilodaltons (kDa).
FIG. 10D is a series of photographs of immunoblots. MCF-10A cells were transfected with a MUC1 siRNA pool (MUC1siRNA) (Dharmacon) or a control siRNA pool (Control) to silence MUC1 expression and then treated with 20 ng/ml TNFα for 30 min. Total cell lysates, cytosolic fractions and nuclear fractions were immunoblotted with the indicated antibodies. The molecular weights of proteins (as indicated on the left of the photographs) are expressed as kilodaltons (kDa).

The binding of MUC1-C to the IKKβ-IKKγ complex could represent a physiologic response in nontransformed cells that is constitutively activated by the overexpression of MUC1 in carcinoma cells. To address this possibility, studies were performed on the nontransformed mammary epithelial cell line, MCF-10A (see, for example, Soule et al. (1990) Cancer Res. 50:6075-6086; and Muthuswamy et al. (2001) Nat. Cell. Biol. 3:785-792), which expresses MUC1, but at levels lower than that found in MCF-7 cells and ZR-75-1 cells (FIG. 10A). As shown in FIG. 10B, very little if any binding of MUC1-C to IKKβ or IKKγ was detected by these methods in the MCF-10A cells. IKKβ and IKKγ are responsible for signaling to NF-κB in the response to tumor necrosis factor a (TNFα) and other proinflammatory cytokines. Significantly, stimulation of the MCF-10A cells with TNFα was associated with increased binding of MUC1-C to IKKβ and IKKγ (FIG. 10B). By contrast, TNFα had no apparent effect on binding of MUC1-C to IKKβ or IKKγ in MCF-7 cells. As depicted in FIG. 10C, treatment of MCF-10A cells with TNFα was also associated with phosphorylation and degradation of IκBα (cytosolic fractions), and targeting of NF-κB p65 to the nucleus (nuclear fractions). Next, MUC1 was transiently silenced in the MCF-10A cells to determine if it contributes to TNFα-induced activation of NF-κB p65 (FIG. 10D). The results shown in FIG. 10D demonstrate that silencing MUC1 attenuates phosphorylation of IκBα and nuclear targeting of NF-κB p65 in the response to TNFα stimulation. These findings indicate that MUC1 plays a physiologic role in activation of the IKKβ/NF-κB p65 pathway.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the present invention.

What is claimed is:

1. A method of treating a subject having a cancer, the method comprising:
   (a) identifying a subject as having a cancer comprising one or more cancer cells expressing MUC1; and
   (b) administering to the subject a composition comprising an isolated MUC1 peptide fragment that inhibits the interaction between MUC1 and an IKK, wherein said MUC1 peptide fragment (i) comprises SEQ ID NO:3 or SEQ ID NO:4 and is up to 50 residues in length, or (ii) consists of SEQ ID NO:13.

2. The method of claim 1, wherein the IKK is IKK-alpha, IKK-beta or IKK-gamma.

3. The method of claim 1, wherein the isolated MUC1 peptide fragment comprises a fragment of the MUC 1 cytosolic domain, wherein the fragment comprises SEQ ID NO:3.

4. The method of claim 1, wherein the isolated MUC1 peptide fragment comprises a fragment of the MUC1 cytosolic domain, wherein the fragment comprises SEQ ID NO:4.

5. The method of claim 1, wherein the cancer cell is from a cancer selected from the group consisting of: lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer.

6. The method of claim 1, further comprising delivering one or more additional anti-cancer therapies.

7. The method of claim 6, wherein the one or more additional anti-cancer therapies comprises one or more chemotherapeutic agents, one or more forms of ionizing radiation, or one or more forms of hormonal therapy.

8. The method of claim 1, wherein the subject is a human.

9. The method of claim 1, wherein the subject is a human.

10. The method of claim 1, wherein the isolated MUC1 peptide fragment consists of SEQ ID NO:13.

* * * * *

UNITED STATES PATENT AND TRADEMARK OFFICE
CERTIFICATE OF CORRECTION

PATENT NO. : 8,129,345 B2
APPLICATION NO. : 11/781148
DATED : March 6, 2012
INVENTOR(S) : Donald W. Kufe Page 1 of 1

It is certified that error appears in the above-identified patent and that said Letters Patent is hereby corrected as shown below:

In column 1, lines 14-18, delete paragraph and insert
--This invention was made with government support under Grant Number CA97098 awarded by the National Cancer Institute of the National Institutes of Health and Grant Number BC022158 awarded by the U.S. Army. The government has certain rights in the invention.-- therefor.

Signed and Sealed this
Twenty-fourth Day of April, 2012

David J. Kappos
*Director of the United States Patent and Trademark Office*